United States Patent [19]

Fujita et al.

[11] 4,336,322
[45] Jun. 22, 1982

[54] COLOR PHOTOGRAPHIC LIGHT-SENSITIVE MATERIAL

[75] Inventors: Shinsaku Fujita; Koichi Koyama; Yoshio Inagaki; Kokichi Waki, all of Minami-ashigara, Japan

[73] Assignee: Fuji Photo Film Co., Ltd., Kanagawa, Japan

[21] Appl. No.: 170,261

[22] Filed: Jul. 18, 1980

[30] Foreign Application Priority Data

Jul. 18, 1979 [JP] Japan .................................. 54-91187
Nov. 13, 1979 [JP] Japan ................................. 54-146654
Nov. 13, 1979 [JP] Japan ................................. 54-146655
Nov. 14, 1979 [JP] Japan ................................. 54-148237
Nov. 19, 1979 [JP] Japan ................................. 54-149777

[51] Int. Cl.$^3$ .................... G03C 1/40; G03C 5/54; G03C 1/10
[52] U.S. Cl. .................... 430/242; 430/559; 430/562; 430/380; 430/390; 430/218; 430/223
[58] Field of Search .............. 430/223, 559, 562, 552, 430/543, 242, 380, 390

[56] References Cited

U.S. PATENT DOCUMENTS 4,053,428 10/1977 Koyama .............................. 430/223
4,149,892 4/1979 Deguchi et al. .................... 430/223
4,152,153 5/1979 Fleckenstein et al. .............. 430/223

*Primary Examiner*—Richard L. Schilling
*Assistant Examiner*—John L. Goodrow
*Attorney, Agent, or Firm*—Sughrue, Mion, Zinn, Macpeak & Seas

[57] ABSTRACT

A color photographic light-sensitive material is described containing a dye-releasing redox compound having the following formula:

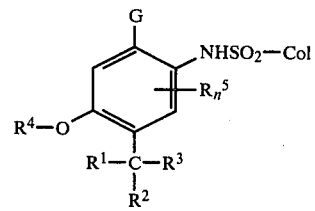

wherein G represents a hydroxy group or a group providing a hydroxy group by hydrolysis;

Col represents a dye or a dye precursor;

$R^1$ and $R^2$, which may be the same or different, each represents an alkyl group or an aromatic group, and $R^1$ and $R^2$ together can form a ring;

$R^3$ represents hydrogen, an alkyl group or an aromatic group;

$R^4$ can represent an alkyl group or an aromatic group;

$R^5$ can represent an alkyl group, an alkoxy group, an alkylthio group, an arylthio group, a halogen atom or an acylamino group;

n is 0, 1 or 2; and $R^4$ and an $R^5$ together can form a heterocyclic ring, $R^1$ and $R^4$ together can form a heterocyclic ring, $R^1$ and an $R^5$ together can form a ring, $R^1$, $R^2$ and $R^3$ together can form an adamantyl ring, and the total number of carbon atoms of $R^1$, $R^2$, $R^3$, $R^4$ and $R_n^5$ is more than 7.

23 Claims, No Drawings

COLOR PHOTOGRAPHIC LIGHT-SENSITIVE MATERIAL

BACKGROUND OF THE INVENTION

1. Field of the Invention

This invention relates to a color light-sensitive material and a process for the formation of a dye image by use of the color light-sensitive material. More particularly it is concerned with a color light-sensitive material which contains a compound capable of releasing a diffusible dye (or dye precursor) by redox reaction (hereinafter referred to as "DRR compound"), and a process for forming a dye image by using the color light-sensitive material.

2. Description of the Prior Art

Japanese Patent Application (OPI) No. 33826/73 (the term "OPI" as used herein refers to a "published unexamined Japanese patent application") discloses a color diffusion transfer dye image-forming method utilizing a DRR compound. DRR compounds as referred to herein are p-sulfonamidophenols or p-sulfonamidonaphthols wherein the dye portion and the nondiffusing phenol or naphthol portion are bound at the p-position through the sulfonamido group. On exposing such a compound in the presence of a light-sensitive silver halide emulsion and then developing the emulsion, the compound is oxidized corresponding to the amount of silver halide developed. This oxidized product decomposes by the action of an alkali processing liquid into a diffusible dye portion containing a sulfonamide group and a nondiffusing benzoquinone or naphthoquinone. It is further described that the diffusible dye so formed is transferred to an image-receiving layer.

However, the inventors' experiments have revealed that the p-sulfonamidophenol as described above fails to provide a transfer density as high as is desirable. Furthermore, the p-sulfonamidophenol, even if it is subjected to a desilvering processing after the release of dye, leaves p-naphthoquinone in a light-sensitive layer, forming yellow stains therein and therefore color images remaining in the light-sensitive layer cannot be utilized as a negative or positive image.

Japanese Patent Application (OPI) No. 113624/76 discloses a DRR compound, viz., an o-sulfonamidophenol substituted by an alkoxyl group at the 4-position. While this compound is very superior in capabilities to conventional, it has been desired to further improve dye-releasing capability.

Additionally, in Japanese Patent Application (OPI) No. 149328/78, a DRR compound comprising o-sulfonamidophenol having an alkoxyl group at the 3-position and a methyl group at the 4-position is described. With respect to this compound also, it has been desired to further improve the dye-releasing capability.

Examples of magenta DRR compounds are described in Japanese Patent Application (OPI) Nos. 115528/75, 114424/74, U.S. Patents 3,932,380, 3,931,144, etc. However, the use of such magenta DRR compounds give rise to the technical problem that the transferred image lacks the desired stability, for example, (1) the light-resistance is insufficient, (2) the fading of color images even when stored in a dark place ("dark fading") is undesirably great, (3) the hue of the color image is easy to change with pH, and (4) the dye portion is insufficiently transferred.

With regard to the dark fading of a transferred color image, for example, it is known in the art that where polymer acids as described in U.S. Pat. No. 3,362,819 (e.g., polyacrylic acid, a copolymer of acrylic acid and butyl acrylate, etc.) are used in a neutralizing layer, the remaining monomers (e.g., acrylic acid, butyl acrylate, etc.) accelerate the dark fading of transferred color images. Subsequent studies have revealed that among such residual monomers, butyl acrylate monomer, in particular, greatly accelerates the dark fading of the magenta image obtained by the prior art method, as described, for example, in U.S. Pat. No. 3,932,380.

However, in producing such polymer acids for use in the neutralizing layer, it is technically very difficult to reduce or remove the residual monomers to such an extent that they exert no influence on the fastness of images. Therefore, it has been desired to develop DRR compounds capable of releasing dye compounds which substantially do not react with such monomers.

SUMMARY OF THE INVENTION

An object of this invention is to provide a light-sensitive material containing a novel DRR compound.

Another object of this invention is to provide a light-sensitive material containing a novel DRR compound which, when used in diffusion transfer, provides a high transfer density.

A further object of this invention is to provide a light-sensitive material containing a novel DRR compound which, after the release of dye, provides a remaining dye image showing reduced yellow stain.

Still another object of this invention is to provide a light-sensitive material containing a novel DRR compound which has good dye-releasing efficiency.

A further object of this invention is to provide a DRR compound which provides a stable dye image.

Another object of this invention is to provide a DRR compound releasing a dye which is good in the hue of the dye portion (i.e., an advantage for color reproduction).

It has now been found that the above objects can be attained by using a DRR compound represented by formula (I):

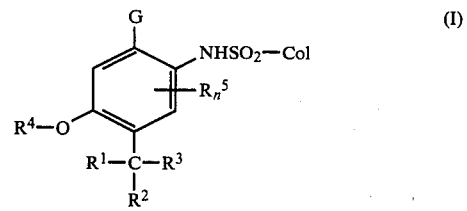

(I)

wherein G represents a hydroxy group or a group providing a hydroxy group by hydrolysis;

Col represents a dye or a dye precursor;

$R^1$ and $R^2$, which may be the same or different, each represents an alkyl group or an aromatic group, and $R^1$ and $R^2$ together can form a ring;

$R^3$ represents hydrogen, an alkyl group or an aromatic group;

$R^4$ can represent an alkyl group or an aromatic group;

$R^5$ can represent an alkyl group, an alkoxy group, an alkylthio group, an arylthio group, a halogen atom or an acylamino group;

n is 0, 1 or 2 and when n is 2, the two $R^5$s can be different from each other; and $R^4$ and an $R^5$ together can form a heterocyclic ring, $R^1$ and $R^4$ together can form a heterocyclic ring, $R^1$ and an $R^5$ together can form a ring, $R^1$, $R^2$ and $R^3$ together can form an adamantyl ring, and the total number of carbon atoms contained in $R^1$, $R^2$, $R^3$, $R^4$ and $R^5_n$ is more than 7.

DETAILED DESCRIPTION OF THE INVENTION

Examples of those groups providing a hydroxy group by hydrolysis, which are represented by G in formula (I), are a group represented by the formula: RCOO— wherein R represents an alkyl group having from 1 to 39, preferably from 1 to 7 and more preferably from 1 to 3 carbon atoms, e.g., acetoxyl and propionyloxy; or an aromatic group having from 6 to 39, preferably from 6 to 14 and more preferably from 6 to 8 carbon atoms, e.g., benzoyloxy and substituted benzoyloxy.

The term "dye" or "dye precursor", which is represented by Col in formula (I), includes not only "dye per se" but also a linking group existing between the genuine dye portion and —NHSO$_2$—.

Examples of such dyes are azo dye, azomethine dye, indoaniline dye, indophenol dye, triphenylmethane dye, anthraquinone dye, indigo dye and metal complex salts thereof. In addition, examples of dye precursors providing the dyes as described above by hydrolysis are those containing an acylated auxochrome as described, for example, in Japanese Patent Application (OPI) No. 125818/73, U.S. Pat. Nos. 3,222,196, 3,307,947, etc. In particular, the latter dyes are useful in allowing the absorption of dye to be within the short wavelength region temporarily during the exposure for the purpose of preventing desensitization due to light absorption, which can take place when a redox compound is mixed with a light-sensitive emulsion and coated. Alternatively, for the same purpose, those dyes can be employed which when transferred onto a mordant provide hues which are different from those which they provide in an emulsion layer.

The Col portion can also contain a group or groups, such as carboxyl and sulfonamide, which provide water-solubility.

Yellow dye portions are described in Japanese Patent Application (OPI) Nos. 7727/77, 1493289/78, 114930/76, *Research Disclosure*, No. 17630 (1978), U.S. Pat. No. 4,013,633, etc.; magenta dye portions, in West German Patent Application (OLS) No. 2,847,371, Japanese Patent Application (OPI) Nos. 23628/78, 106727/77, 65034/79, 161332/79, 4028/80, 36804/80, Japanese Patent Application No. 42848/79, U.S. Pat. Nos. 3,954,476, 3,931,144, 3,932,308, etc.; and cyan dye portions, in U.S. Pat. Nos. 3,942,987, 3,929,760, 4,013,635, Japanese Patent Application (OPI) Nos. 149328/78, 8827/77, 47823/78, 143323/78, etc.

Examples of alkyl groups represented by $R^1$, $R^2$, $R^3$ or $R^4$ contain from 1 to 40, and preferably from 1 to 24, carbon atoms, and may be straight, branched or cyclic and furthermore may be substituted, for example, by alkoxy, cyano, hydroxy, halogen, phenoxy, substituted phenoxy, acylamino or the like. Preferred examples of such alkyl groups are a straight alkyl group such as methyl, ethyl, propyl, butyl, pentyl, hexyl, heptyl, undecyl, pentadecyl, heptadecyl, etc., and a branched alkyl group such as isopropyl, isobutyl, tert-butyl, tert-amyl, neopentyl, etc.

Aromatic groups represented by $R^1$, $R^2$, $R^3$ and $R^4$ include a phenyl group, a substituted phenyl group, a naphthyl group, a substituted naphthyl group and the like. Examples of substituents for the substituted phenyl or naphthyl group are an alkoxy group, a cyano group, a hydroxy group, a nitro group, an alkyl group, etc. Where $R^1$ and $R^2$ combine together to form a ring, it is desirable that they form a ring having from 5 to 40, and preferably from 5 to 12, members with a saturated ring being particularly preferred.

With regard to the alkyl group, the alkoxy group and the alkylthio group which can be represented by $R^5$, the alkyl portion may, e.g., contain from 1 to 40, and preferably contains from 1 to 24 carbon atoms, and may be straight, branched or cyclic; furthermore, it may be substituted, for example, by alkoxy, cyano, hydroxy, halogen, phenoxy, substituted phenoxy, acylamino, or the like.

Preferred examples of the alkyl group represented by $R^5$ are the same as described for $R^1$.

Preferred examples of the arylthio group represented by $R^5$ are a phenylthio group, a substituted phenylthio group and a heterocyclic thio group.

Representative examples of the acylamino group represented by $R^5$ are an alkyl—CONH—group and a substituted or unsubstituted phenyl—CONH—group.

Examples of substituents for the substituted phenylthio group or substituted phenyl—CONH—group represented by $R^5$ are the same as described for the substituted aryl group represented by $R^1$ or $R^2$.

Heterocyclic thio groups represented by $R^5$ include those generally known as a development inhibiting agent-releasing group.

The halogen of $R^5$ can be, e.g., fluorine, chlorine and bromine.

$R^4$ and $R^5$ together, $R^1$ and $R^4$ together, and $R^1$ and $R^5$ together may form a ring, with a 5- or 6-membered ring being preferred. The ring formed by $R^1$ and $R^5$ may be a heterocyclic ring containing as a hetero atom O, N or the like. It is noted that the formation of an aromatic hydrocarbon condensed ring is not preferred in that color stains may be formed in the remaining areas.

In order to prevent the DRR compound from diffusing, or flowing before reaction, by the action of an alkali used in the development of the light-sensitive material, it is required that the DRR compound contains a ballast group. While the size of the number of carbon atoms required for the ballast group varies depending upon the conditions employed, for example, the processing time and the concentration of alkali and the number and type of the water-soluble group contained in the Col portion, at least the total number of carbon atoms in $R^1$, $R^2$, $R^3$, $R^4$ and $R^5_n$ is required to be 7 or more. A number of carbon atoms which is much greater than necessary is not desirable from the points of solubility and absorptivity but theoretically there is no upper limit in the number of carbon atoms. In general, the total number of carbon atoms in $R^1$, $R^2$, $R^3$, $R^4$, and $R^5_n$ is from 7 to 80, and preferably is from 13 to 40.

*Research Disclosure*, No. 13024 (1975) shows 6-sulfonamidophenols, of which 2-sulfonamidophenol having an alkyl group at the 5-position is said to have almost no developing activity and therefore not to release any dye. On the other hand, the DRR compound of this invention has the $R^4O$—group at the 5-position of phenol and the secondary or tertiary alkyl or aralkyl group, i.e., the $R^1R^2R^3C$—group at the 4-position, which brings about significant differences in photographic capabilities. In comparison with the compounds disclosed in Japanese Patent Application (OPI) Nos. 113624/76 and 149328/78, the DRR compound of this invention is superior in that the steric hindrance of the secondary or tertiary alkyl group ($R^1R^2R^3C-$) prevents side reaction (e.g., ipso reaction, that is, a reaction caused at the position of the carbon atom having an aromatic substituent, as described in S. R. Hartshorn, *Chemical Society Review*, vol. 3, pp 167-192 (1974)) during not only the oxidation reaction but also the hydrolysis of the oxidized product of the present DRR compound, increasing the dye-releasing efficiency. Therefore, the oxidized product of the present DRR compound efficiently releases the diffusible dye.

This high dye-releasing efficiency of the present DRR compound enable obtainment of a dye image of a desired density even though using it in a smaller amount than for the conventional compounds. This, furthermore, permits the reduction in the amount of a binder to be used in combination with the DRR compound and it is, therefore, possible to reduce the thickness of the layer. Additionally, this reduction in the thickness of the layer increases the transfer speed of the released dye.

The DRR compound of this invention produces o-quinoneimide by the redox reaction in the development and the o-quinoneimide releases the sulfonamide portion by hydrolysis. It is believed that since the o-benzoquinone resulting from the release of the sulfonamide portion shows absorptions only in much shorter wavelength region as compared with the conventional naphthoquinones, this causes the stains remaining after the release of dye to be reduced.

Preferred compounds of this invention are represented by the following formula (II):

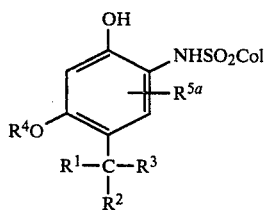

wherein $R^{5a}$ is hydrogen or the same as defined for $R^5$ and $R^1$, $R^2$, $R^3$, $R^4$ and Col are the same as defined in formula (I), more preferably $R^1$ and $R^2$ may be the same or different and each represents an alkyl group or an aromatic group, or $R^1$ and $R^2$ may combine together to form a saturated hydrocarbon ring; $R^3$ represents a hydrogen atom, an alkyl group or an aromatic group or $R^1$, $R^2$ and $R^3$ combine together to form an adamantyl group; $R^4$ represents an aryloxyalkyl or unsubstituted alkyl group, these groups having the total number of carbon atoms of 1 to 24 being particularly preferred; and $R^{5a}$ represents a hydrogen atom, an alkyl or alkoxy group, these groups having the total number of carbon atoms of 1 to 24 being particularly preferred, furthermore preferably $R^3$ is an alkyl group or an aryl group and $R^1$ and $R^2$ may be the same of different and each represents an alkyl group or an aromatic group.

Preferred and specific examples of

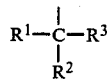

are a t-butyl group, a cyclohexyl group, an adamantyl group, a t-amyl group, a 1-ethyl-1-methylpentyl group, a t-hexyl group, a t-octyl group and a

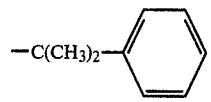

group.

The compounds represented by formula (I) can generally be produced by the condensation of sulfonyl halide of azo dye having the formula (III) as shown below and o-aminophenol derivatives having the formula (IV) as shown below.

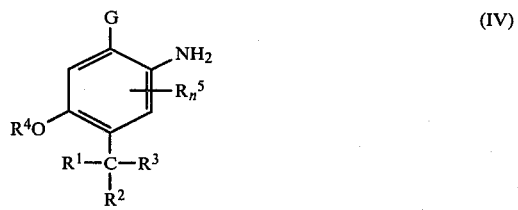

wherein X is a halogen atom and the other symbols are the same as defined in formula (I).

Cyan DRR compounds having a group represented by formula C-(I) as the "Col" have been found to be especially suitable for use in this invention.

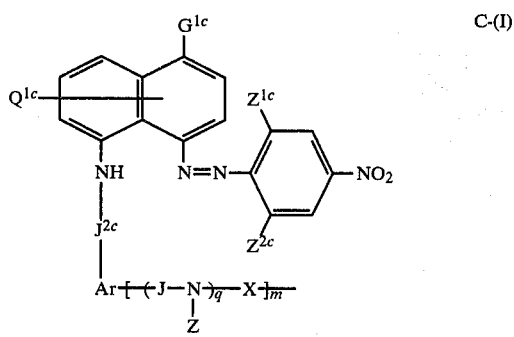

$Q^{1c}$ is bound to one of the rings of the naphthol nucleus and represents hydrogen, a halogen atom, or a sulfamoyl group represented by the formula: $-SO_2-NY^{3c}Y^{4c}$ (wherein $Y^{3c}$ represents a hydrogen atom, an alkyl group or a substituted alkyl group, $Y^{4c}$ represents a hydrogen atom or $Y^{4ac}$ (wherein $Y^{4ac}$ represents an alkyl group, a substituted alkyl group, an aralkyl group or an aryl group), and $Y^{3c}$ and $Y^{4c}$ may be bound together directly or through an oxygen atom to form a ring), $-SO_2Y^{5c}$ (wherein $Y^{5c}$ represents an alkyl group, a substituted alkyl group or a benzyl group), a carboxyl group, $-COOY^{6c}$ (wherein $Y^{6c}$ represents an alkyl group, a substituted alkyl group, a phenyl group or a substituted phenyl group), or $-CONY^{3c}Y^{4c}$ (wherein $Y^{3c}$ and $Y^{4c}$ are the same as defined above);

$J^{2c}$ represents $-SO_2-$ or $-CO-$;

Ar represents a phenylene group or a substituted phenylene group;

$Z^{1c}$ represents a halogen atom, a cyano group, a nitro group, a trifluoromethyl group, an alkyl group, an alkoxy group, a carboxyl group, a carboxylic acid ester group represented by $-COOY^{6c}$ (wherein $Y^{6c}$ is the same as defined above), a fluorosulfonyl group, a phenoxysulfonyl group, a substituted phenoxysulfonyl group, a sulfamoyl group represented by $-SO_2NY^{3c}Y^{4c}$ (wherein $Y^{3c}$ and $Y^{4c}$ are the same as defined above), a carbamoyl group represented by $-CONY^{3c}Y^{4c}$ (wherein $Y^{3c}$ and $Y^{4c}$ are the same as defined above), an alkylsulfonyl group, a substituted alkylsulfonyl group, a phenylsulfonyl group or a substituted phenylsulfonyl group;

$Z^{2c}$ represents a hydrogen atom, a halogen atom, a nitro group, a cyano group or a trifluoromethyl group;

J represents $-SO_2-$ or $-CO-$;

Z represents a hydrogen atom, an alkyl group or a substituted alkyl group;

X represents a divalent bonding residue represented by the formula: $-A_1-(L)_l-(A_2)_p-$ (wherein $A_1$ and $A_2$ are, the same or different, an alkylene group or an arylene group, L is a divalent residue selected from oxy, carbonyl, carboxyamido, carbamoyl, sulfinyl, sulfonamido, sulfamoyl or sulfonyl, and l and p are each 0 or 1);

m and q each represents 0 or 1; and $G^{1c}$ represents a hydroxy group or a group providing a hydroxy group by hydrolysis, Representative examples of $G^{1c}$ are the same as listed for G.

Where $Q^{1c}$ is a sulfamoyl group represented by the formula: $-SO_2NY^{3c}Y^{4c}$, $Y^{3c}$ is preferably a hydrogen atom, an alkyl group containing from 1 to 8 carbon atoms, and more preferably from 1 to 4 carbon atoms, or a substituted alkyl group, the alkyl residue of which contains from 1 to 8 carbon atoms, and preferably from 1 to 4 carbon atoms; $Y^{4c}$ is preferably hydrogen, an alkyl group containing from 1 to 8 carbon atoms, and more preferably from 1 to 4 carbon atoms, a substituted alkyl group, the alkyl residue which contains from 1 to 8 carbon atoms, and more preferably from 1 to 4 carbon atoms, a benzyl group, a phenyl group or a substituted phenyl group containing 6 to 9 carbon atoms; and $Y^{3c}$ and $Y^{4c}$ may be bound together directly or through oxygen to form a 5- or 6-membered ring. Of these compounds, those wherein $Y^{3c}$ and $Y^{4c}$ are both hydrogen or hydrogen and alkyl containing from 1 to 4 carbon atoms are particularly preferred on the grounds that they are inexpensive, easily available in the market (i.e., DRR compounds can be produced at low cost since the starting material is cheap, hereinafter the same), and excellent in transferability.

The same considerations apply to the group $-CONY^{3c}Y^{4c}$.

The group $-SO_2Y^{5c}$, $Y^{5c}$ is preferably an alkyl group containing from 1 to 8 carbon atoms, a substituted alkyl group, the alkyl portion of which contains from 1 to 8 carbon atoms, or a benzyl group. In particular, an alkyl group containing from 1 to 4 carbon atoms and a benzyl group are preferred because of low cost, easy availability and excellent transferability.

Preferred examples of $Y^{6c}$ in $-COOY^{6c}$ are an alkyl group containing from 1 to 8 carbon atoms, preferably from 1 to 4 carbon atoms, a substituted alkyl group which has an alkyl residue containing from 1 to 8 carbon atoms, and preferably from 1 to 4 carbon atoms, a phenyl group, a substituted phenyl group containing from 6 to 9 carbon atoms, etc.

Examples of substituents for the substituted alkyl group in $Y^{3c}$ to $Y^{6c}$ are a cyano group, an alkoxy group, a hydroxyl group, a carboxyl group, a sulfo group, etc. Examples of substituents for the substituted phenyl group in $Y^{6c}$ are a hydroxyl group, a halogen atom, a carboxy group, a sulfo group, a sulfamoyl group, etc.

Substituents for the substituted phenyl group represented by Ar include a carboxyl group, a halogen atom, an alkyl group containing from 1 to 4 carbon atoms and an alkoxy group containing from 1 to 4 carbon atoms.

The alkyl group in $Z^{1c}$ may be straight or branched, preferably contains from 1 to 8 carbon atoms, and more preferably contains from 1 to 4 carbon atoms. The alkoxy group represented by $Z^{1c}$ may be straight or branched and preferably contains from 1 to 8 carbon atoms, and more preferably from 1 to 4 carbon atoms. Preferred examples of the groups $-SO_2NY^{3c}Y^{4c}$ and $-CONY^{3c}Y^{4c}$ represented by $Z^{1c}$ are the same as listed for $Q^{1c}$. The alkylsulfonyl group in $Z^{1c}$ may be straight or branched and preferably contains from 1 to 8 carbon atoms, more preferably from 1 to 4 carbon atoms.

The alkylene group represented by $A_1$ and $A_2$ includes a straight or branched alkylene group containing from 1 to 8 carbon atoms, and preferably from 1 to 4 carbon atoms. Examples of the arylene group represented by $A_1$ and $A_2$ are an m- or p-phenylene group and an m- or p-phenylene group substituted by a halogen atom, an alkoxy group containing from 1 to 8 carbon atoms, and preferably from 1 to 4 carbon atoms, a cyano group, a nitro group, an alkyl group containing from 1 to 8 carbon atoms, and preferably from 1 to 4 carbon atoms, a carboxy group, a sulfo group, $-O-Y^{1a}-O-Y^{2a}$ (wherein $Y^{1a}$ is an alkylene group containing 2 or more carbon atoms and $Y^{2a}$ is an alkyl group or a substituted alkyl group) or the like.

Preferred cyan DRR compounds having a group of formula (C-(I) are those as described in the abovementioned formula (II).

In more preferred embodiments, the cyan DRR compounds of this invention are those having a group represented by the following formula C-(II) as the "Col".

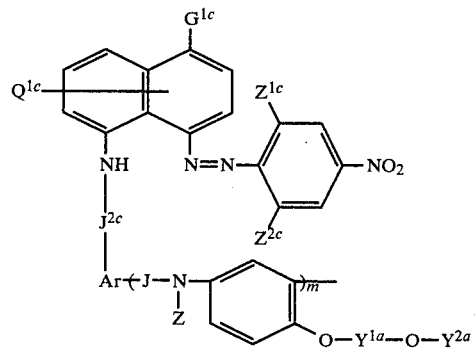

C-(II)

wherein $G^{1c}$, $Q^{1c}$, $Z^{1c}$, $Z^{2c}$, J, $J^{2c}$, Ar, Z, $Y^{1a}$, $Y^{2a}$, and m are the same as defined in formula C-(I).

The alkylene group containing 2 or more carbon atoms which is represented by $Y^{s\ 1a}$, may be straight or branched, and preferably contains from 2 to 8 carbon atoms, excluding a branched alkylene group which forms an acetal bond. Preferred examples of $Y^{1a}$ are a straight alkylene group represented by $-(CH_2)_{p'}-$ (wherein $p'$ is an integer of from 2 to 4) and a branched alkylene group containing from 3 to 4 carbon atoms, represented by —CH(CH₃)CH₂—, —CH₂—CH₂—CH(CH₃)— or the like. Those forming an acetal bond are excluded. The case where $Y^{1a}$ is —CH₂CH₂— is particularly preferred, due to the easy availability of the starting material. It is not preferred that $Y^{1a}$ be a methylene group, since it forms an acetal bond, e.g., —O—CH₂—O—$Y^{2a}$ which is chemically unstable, particularly under acidic conditions, and decomposes in the course of the synthesis thereof. For the same reason as above, it is not preferred that the two oxygen atoms in the group —O—$Y^{1a}$—O—$Y^{2a}$ be bound to the same carbon in $Y^{1a}$, since this can result in the formation of an acetal bond.

The alkyl group represented by $Y^{2a}$ may be straight or branched and preferably contains from 1 to 8 carbon atoms. $Y^{2a}$ is preferably an unsubstituted alkyl group from the point of the synthesis. Particularly preferred examples are straight or branched alkyl groups containing from 1 to 4 carbon atoms, such as methyl, ethyl, n-propyl, isopropyl and n-butyl. Examples of substituents for the substituted alkyl group are an alkoxy group, e.g., methoxy and ethoxy and a dialkylamino group, e.g., diethylamino.

Representative examples of the cyan DRR compounds of this invention are shown below:

Compound C-1

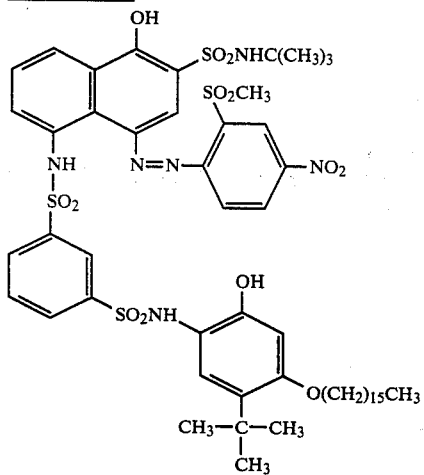

Compound C-2

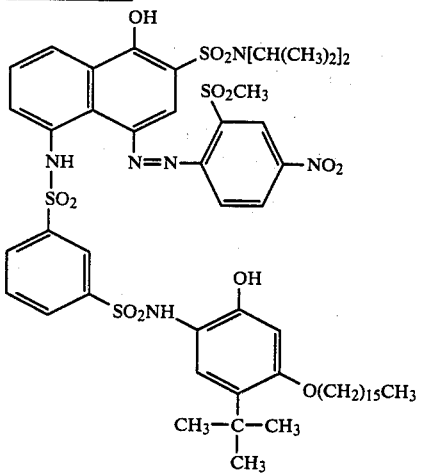

Compound C-3

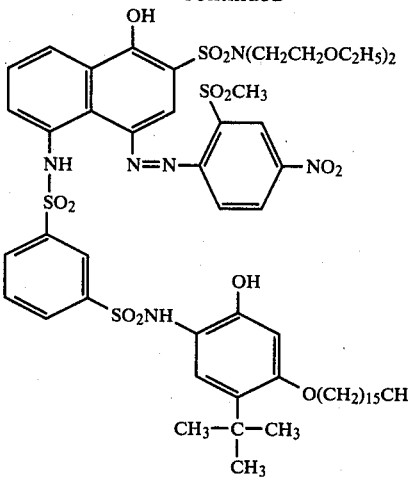

Compound C-4

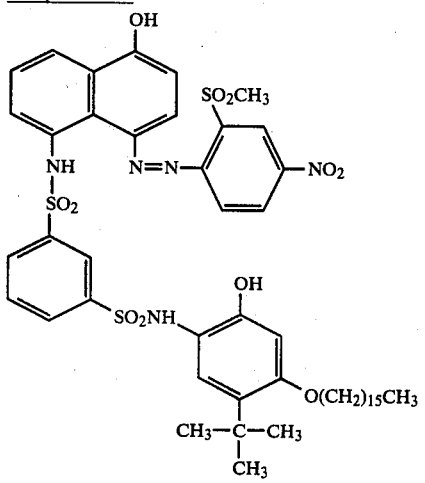

Compound C-5

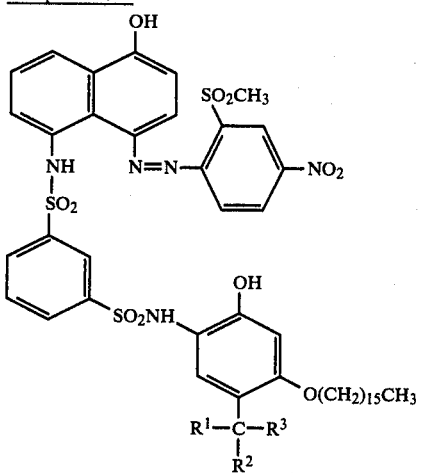

wherein $R^1 = R^2 = CH_3$ and $R^3 = C_6H_5$.

Compound C-6

In the formula of Compound C-5, $R^1 = R^2 = CH_3$ and $R^3 = C_2H_5$.

Compound C-7

In the formula of Compound C-5, $R^1 = R^2 = CH_3$ and $R^3 = CH_2—C(CH_3)_3$.

Compound C-8

In the formula of Compound C-5, $R^1=CH_3$, $R^2=C_2H_5$ and $R^3=C_4H_9\text{—}n$.

Compound C-9

In the formula of Compound C-5, $R^1=R^2=CH_3$ and $R^3=H$.

Compound C-10

In the formula of Compound C-5, $R^1+R^2=-(CH_2)_5-$ and $R^3=H$.

Compound C-13

In the formula of Compound C-11, $R^1=R^2=CH_3$ and $R^3=-(CH_2)-C(CH_3)_3$.

Compound C-14

In the formula of Compound C-11, $R^1=CH_3$, $R^2=C_2H_5$ and $R^3=C_4H_9\text{—n}$.

Compound C-15

In the formula of Compound C-11, $R^1=R^2-CH_3$ and $R^3=H$.

Compound C-11

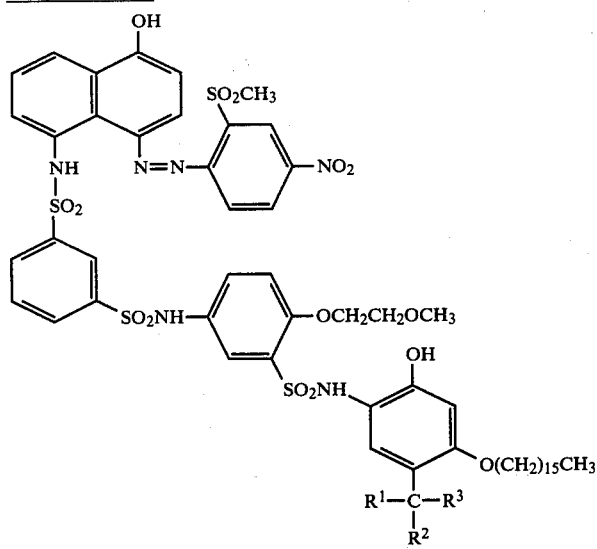

wherein $R^1=R^2=R^3=CH_3$.

Compound C-12

In the formula of Compound C-11, $R^1=R^2=CH_3$ and $R^3=C_2H_5$.

Compound C-16

In the formula of Compound C-11, $R^1+R^2=-(CH_2)_5-$ and $R^3=H$.

Compound C-17

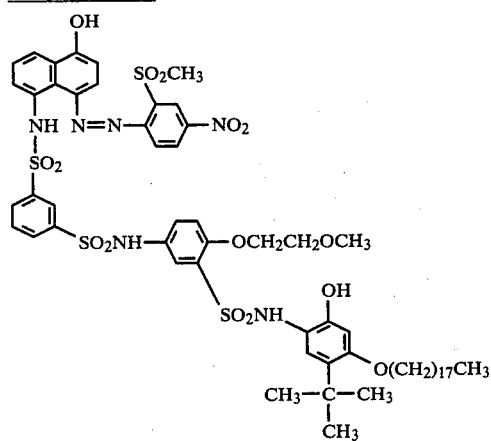

Compound C-18

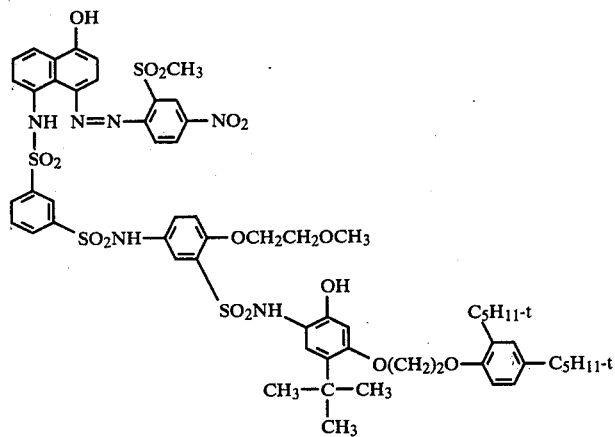

Compound C-19

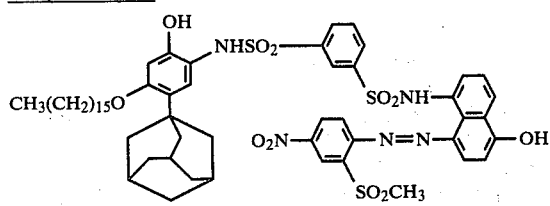

Compound C-20

-continued

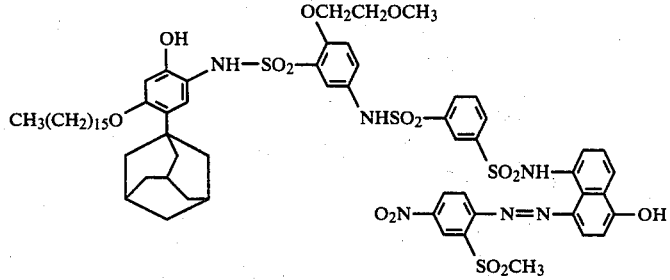

Compound C-21

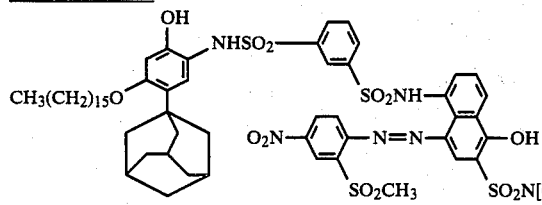

Compound C-22

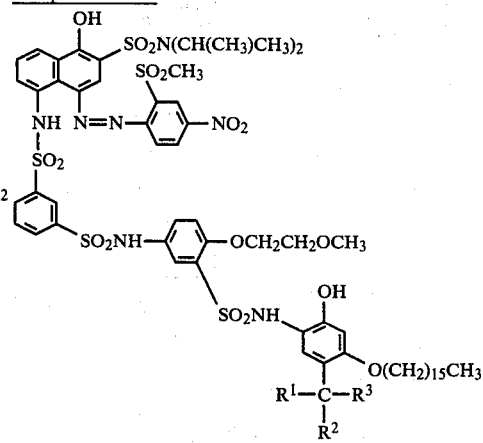

wherein $R^1=R^2=R^3=CH_3$

The cyan DRR compounds of this invention can generally be synthesized by the condensation of sulfonyl halide of azo dye having the formula C-(V) as shown below, and o-aminophenol derivatives containing various organic ballast groups, having the formula C-(VI) as shown below.

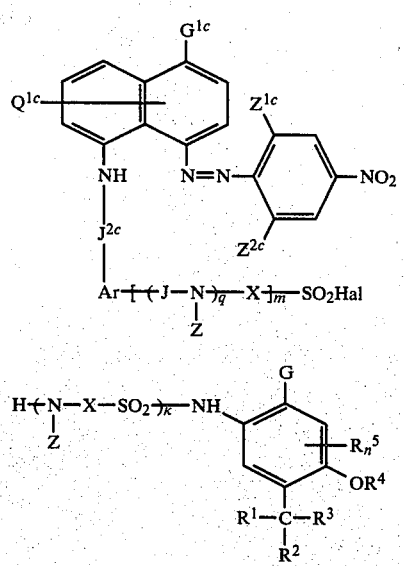

C-(V)

C-(VI)

wherein Hal is a halogen atom; where m is 0, k is 1 or 0 and where m is 1, k is 0; and the other symbols are the same as defined in Formulae (I) and C-(I).

The above condensation reaction is desirably carried out in the presence of a basic substance. Examples of such basic substances are hydroxides of alkali metals or alkaline earth metals, such as sodium hydroxide, potassium hydroxide, barium hydroxide, calcium hydroxide, etc., aliphatic amines, such as triethylamine, etc., aromatic amines, such as N,N-diethylaniline, etc., heteroaromatic amines, such as pyridine, quinoline, α-, β- or γ-picoline, lutidine, collidine, 4-(N,N-dimethylamino)pyridine, etc., and heterocyclic bases, such as 1,5-diazabicyclo[4,3,0]-nonene-5,1,8-diazabicyclo[5,4,0]undecene-7, etc. When Hal is chlorine, that is, formula C-(V) is a sulfonyl chloride, the heteroaromatic amines (preferably pyridine) are excellent.

Typical pathways for the synthesis of the amines represented by formula C-(VI) are shown below.

Pathway I

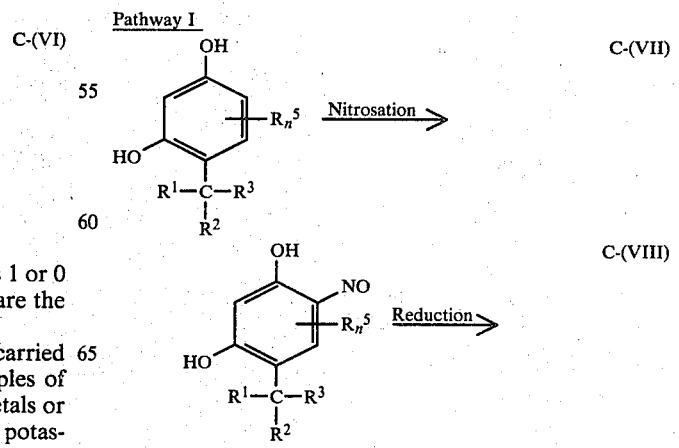

-continued

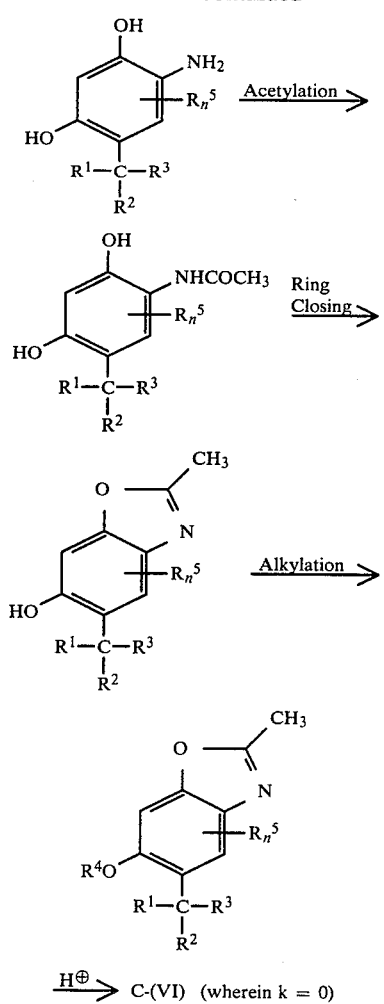

Pathway II

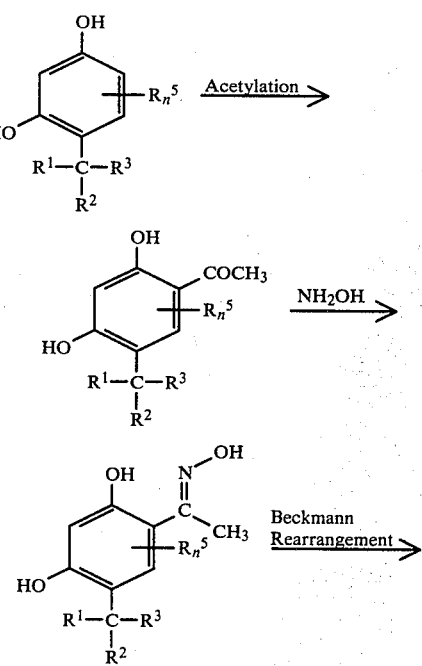

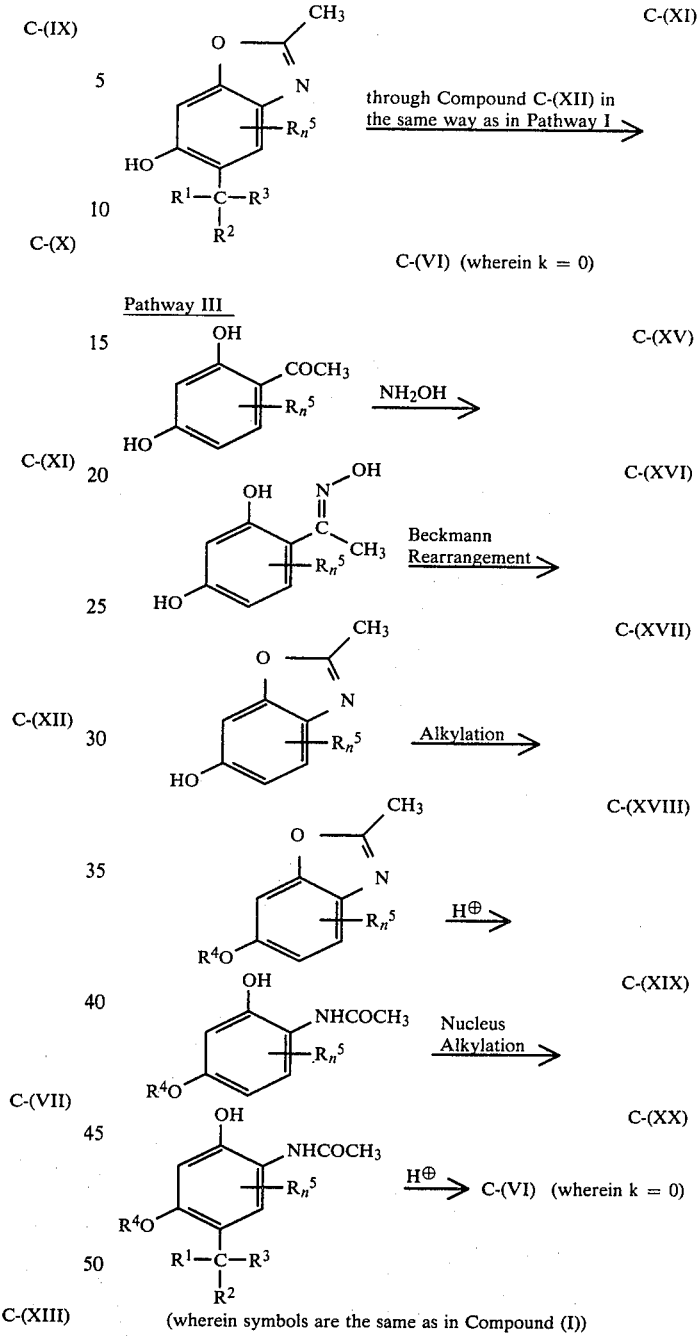

(wherein symbols are the same as in Compound (I))

Pathway I will be explained first.

The resorcinol of formula C-(VII) is converted in the corresponding nitroso compound, which is in turn reduced and acetylated to obtain Compound C-(X). For these reaction steps, operations as described in W. M. McLamore, *J. Amer. Chem. Soc.*, Vol. 73, pp. 2225 to 2230 (1951) referring to the reaction of 4-cyclohexyl-resorcinol to 2-acetamido-4-cyclohexylresorcinol can be utilized.

The formation of the oxazole ring can be carried out by processing Compound C-(X) in the presence of an acid catalyst, such as p-toluenesulfonic acid. This formation can be conducted by reference to the description in Japanese Patent Application (OPI) No. 153923/77.

In the o-alkylation of Compound C-(XI), oxazole derivative, R⁴-Hal (wherein Hal is a halogen atom) is usually used and as a dehydrogen halogenation agent, a basic substance, e.g., sodium alkoxide, potassium carbonate, etc., is employed. This alkylation reaction can be carried out by reference to the description in Japanese Patent Application (OPI) No. 153923/77. The oxazole ring of Compound C-(XII) is opened and then the deacetylation is carried out to obtain Compound C-(VI).

The reaction of Compound C-(XII) to Compound C-(VI) can usually be carried out in a single step by processing with a strong acid without isolating the acetamido substance.

In Pathway II, the resorcinol derivative is acetylated at the nucleus thereof (for example, by use of BF³-acetic acid) and then reacted with hydroxylamine to obtain Compound C-(XIV), an oxime. By blowing through a hydrochloric acid in acetic acid or reacting with phosphorus oxychloric acid or phosphorus pentachloride, the Beckmann rearrangement and the formation of oxazole can be achieved at the same time. The thus-obtained Compound C-(XI) is converted in Compound C-(VI) by the same method as used in Pathway I.

In Pathway III, the 2,5-dihydroxyacetophenone derivative is reacted with hydroxylamine to provide Compound C-(XVI), an oxime. In this step, while those compounds obtained by replacing the acetyl group by other ketone radicals can be used as the starting material, the compound having the acetyl group is preferably used because of ease of synthesis. As is the case with Compound C-(XIV) in Pathway II, the Beckmann rearrangement and the formation of oxazole are carried out at the same time. In obtaining Compound C-(XVIII) by the o-alkylation of the above formed oxazole, Compound C-(XVII), R⁴-Hal (wherein Hal is a halogen atom), is used and as a dehydrogen halogenation, a basic substance, e.g., sodium alkoxide or potassium carbonate is employed. The step of the o-alkylation can be carried out by reference to the description in Japanese Patent Application (OPI) No. 153923/77.

Thereafter, Compound C-(XVIII) is treated with diluted hydrochloric acid to open the oxazole ring and Compound C-(XIX) is thus obtained. By alkylating Compound C-(XIX) at the nucleus thereof with olefin (or alcohol or alkyl halide) in the presence of a catalyst, Compound C-(XX) is obtained.

As the olefin for use in the above alkylation, those represented by the formula: R¹R³C=R²ᵃ (wherein R¹ and R³ are the same as defined in Formula (I) and R²ᵃ is a group which gives R² by protonation) are used. For example, the use of isobutene as the olefin permits the introduction of a tert-butyl group. Alcohols which can be used in the alkylation include those represented by the formula: R¹R²R³C—OH (wherein R¹, R² and R³ are the same as defined in Formula (I)). Alkyl halides which can be used in the alkylation include those represented by the formula R¹R²R³C—Hal (wherein R¹, R² and R³ are the same as defined in formula (I)).

Catalysts which can be used in the alkylation include Bronsted acids such as sulfuric acid, phosphoric acid, etc.; Lewis acids such as aluminum chloride, boron trifluoride, zinc chloride, iron chloride, titanium chloride, antimony pentachloride, etc.; solid catalysts such as clay minerals, e.g., acid clay, bentonite, kaolin, etc., and silica alumina based catalysts; solid acids, i.e., solidified acids produced by deposition of sulfuric acid, phosphoric acid or the like on kieselguhr or quartz; and ion exchange resins such as Amberlite IR-120 (H), Amberlite IR-112 (H), Amberlyst 15, etc. The details of these catalysts and other examples are described in Kozo Tanabe & Tsuneichi Takeshita, *San Enki Syokubai (Acid and Basic Catalysts)*, pp. 23–224, Sangyo Tosho, Tokyo (1966).

With regard to the reaction conditions under which the alkylation is carried out, G. A. Olah, *Friedel-Crafts and Related Reactions*, Vol. II, Alkylation and Related Reaction, Interscience Publishers, New York (1964), R. N. Roberts, *Chem. and Eng. News*, p. 112 (Jan. 25, 1965), etc., can be referred to. With regard to the formation of oxime and the Beckmann rearrangement, *Organic Reactions*, Vol. 11, pp. 1–156, John Wiley & Sons, New York (1960) can be referred to.

The compound wherein k=1 in formula C-(VIII) can be produced as follows: (1) Compound C-(VI) (wherein k=0) and NO₂—X—SO₂Hal (wherein X is the same as in formula C-(I) and Hal is a halogen atom) are condensed and, thereafter, the nitro group is reduced, or (2) Compound C-(VI) (wherein k=0) and AcN(Z)—X—SO₂Hal (wherein X is the same as defined in formula C-(I) and Hal is a halogen atom) are condensed and, thereafter, the deacetylation is carried out.

The above pathway (1) will be explained in greater detail by way of illustration.

The condensation of NO₂—X—SO₂Hal and Compound C-(VI) (wherein k=0) can be carried out under the same conditions as explained for the condensation of Compounds C-(V) and C-(VI). Typical methods which can be employed for the reduction of the nitro group of the condensed product to obtain Compound C-(VI) include a reduction using iron powder, an addition of catalytic hydrogen by using Raney nickel catalyst or a palladium-carbon catalyst, and a hydrazine reduction using a Raney nickel catalyst, a palladium-carbon catalyst or an active carbon catalyst. In addition, methods of reducing a nitro group to form an amino group are described, for example, in R. B. Wagner & H. D. Zook, *Synthetic Organic Chemistry*, Chapter 24, pp. 654–657, John Wiley, New York (1953) and S. R. Sandler & W. Karo, *Organic Functional Group Preparations*, Chapter 13, pp. 339–345, Academic Press, London (1968). These methods are also useful in the synthesis of the compounds of this invention.

The synthesis of NO₂—X—SO₂Cl can be carried out by reference to the descriptions in Japanese Patent Application (OPI) Nos. 22779/76, 149328/78, etc. For example, it can be synthesized as follows:

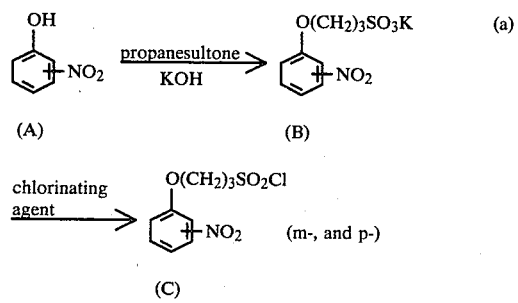

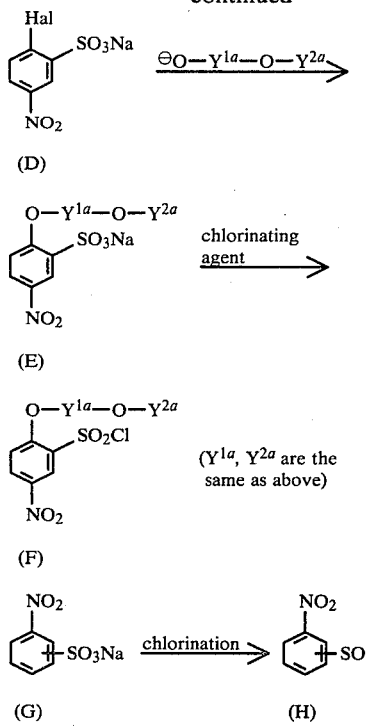

(D)

(E)

(F) ($Y^{1a}$, $Y^{2a}$ are the same as above)

(G) (H) (m- and p-)

The step (b) will be explained in greater detail by way of illustration.

As the method of synthesizing Compound (E) from Compound (D), a method in which an alkoxide represented by the formula: $Y^{2a}$—O—$Y^{1a}$—ONa (wherein $Y^{1a}$ and $Y^{2a}$ are the same as defined in formula C-(II)) can be employed. This alkoxide can be obtained by treating an alcohol having the formula: $Y^{2a}$—O—$Y^{1a}$—OH with metallic sodium or sodium hydride. While $Y^{2a}$—O—$Y^{1a}$—ONa may be isolated by distilling off the excess $Y^{2a}$—O—$Y^{1a}$—OH and used, it is usually preferred that the solution of $Y^{2a}$—O—$Y^{1a}$—ONa in $Y^{2a}$—O—$Y^{1a}$—OH is used as is.

The amount of $Y^{2a}$—O—$Y^{1a}$—ONa being used per mol of the compound of formula (D) is from about 1 mol to about 50 mols, preferably from about 1 mole to about 10 mols and more preferably from about 1 mol to about 3 mols.

The reaction temperature is from about −20° C. to about 150° C., preferably from 0° C. to about 100° C., and more preferably from 30° C. to 85° C., to inhibit side reactions.

Another method of synthesizing Compound (E) is to treat Compound (D) with sodium hydroxide or potassium hydroxide in $Y^{2a}$—O—$Y^{1a}$—OH in the presence of manganese dioxide. In this method, sodium hydroxide is preferably used. One mol of Compound (D) and about 10 g to about 1 kg (preferably from about 10 g to about 500 g, and especially preferably from about 30 g to about 100 g) of manganese dioxide are suspended in about 100 ml to about 50 l (preferably from about 300 ml to 5 l, and especially preferably from about 400 ml to about 2 l) of $Y^{2a}$—O—$Y^{1a}$—OH and treated with from about 1 mol to 50 mols (preferably from about 1 mol to 10 mols, and especially preferably from about 1 mol to 3 mols) of sodium hydroxide. The reaction temperature is about 0° C. to 150° C. (preferably 0° C. to 100° C., and especially preferably 30° C. to 85° C.).

Another method of synthesizing Compound (E) is to treat Compound (D) with sodium hydroxide or potassium hydroxide in $Y^{2a}$—O—$Y^{1a}$—OH in the presence of sodium silicate ($Na_2O \cdot nSiO_2$, where n is from about 1 to 5, and preferably from about 1 to 3). In this method, sodium hydroxide is preferably used. One mol of Compound (D) and about 10 g to about 1,000 g (preferably about 10 g to about 500 g, and more preferably about 30 g to about 100 g) of sodium silicate are suspended in about 100 ml to about 50 l (preferably about 300 ml to about 5 l, and more preferably from about 400 ml to about 2 l) of $Y^{2a}$—O—$Y^{1a}$—OH and treated with from about 1 mol to about 5 mols (preferably from about 1 mol to about 10 mols, and more preferably from about 1 mol to about 3 mols) of sodium hydroxide. The reaction temperature is from about 0° C. to 150° C., preferably about 0° C. to 100° C., and more preferably from about 30° C. to 85° C.

The reaction solution obtained by one of the above three methods is filtered to remove insoluble products, and the filtrate is then poured in a non- or poor solvent, e.g., alcohols such as isopropyl alcohol, n-butanol and the like; aromatic hydrocarbons such as toluene; and esters such as ethyl acetate to crystallize Compound (E). If necessary, additional purification processing steps, such as recrystallization, may be applied.

Preferred chlorinating agents for use in the conversion of Compound (E) to Compound (F) include phosphorus oxychloride, thionyl chloride, phosphorus pentachloride and chlorosulfonic acid. This reaction is desirably carried out in the presence of N,N-dimethylacetamide, N,N-dimethylformamide, N-methylpyrrolidone or the like.

The sulfonyl halide of azo dye represented by the formula C-(V) can be synthesized as follows:

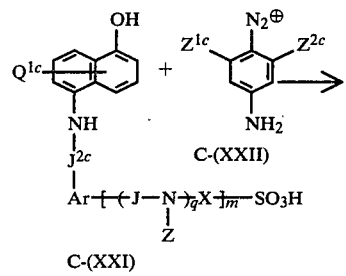

C-(XXI)

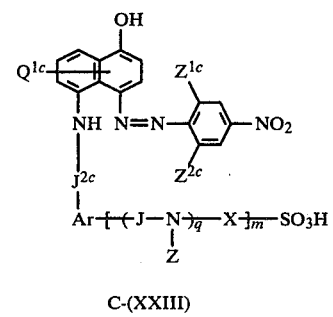

C-(XXIII)

$$\xrightarrow{\text{halogenating agent}} \text{C-(V)}$$

(Symbols are same as in formula C-(I).)

The synthesis of Compound C-(V) is described in Japanese Patent Application (OPI) No. 87343/78 and in U.S. Pat. Nos. 4,013,635 and 3,942,987.

PREPARATION EXAMPLE 1

Synthesis of 6-Hydroxy-2-methylbenzoxazole (formation of oxazole ring by Beckmann rearrangement)

A mixture of 306 g of 2,4-dihydroxyacetophenone, 164 g of hydroxyamine hydrochloric acid salt, 328 g of sodium acetate, 1,000 ml of ethanol and 500 ml of water was refluxed for 4 hours. The reaction solution was poured into 10 l of water to precipitate crystals and these crystals were collected by filtration. 314 g of 4-dihydroxyacetophenoneoxime was obtained.

The thus-obtained oxime in an amount of 30 g was dissolved in 400 ml of acetic acid. While the acetic acid solution was heated at 120° C. to 140° C. with stirring, a hydrogen chloride gas was blown through the acetic acid solution for 2 hours.

The acetic acid solution was cooled to precipitate crystals, and the crystals were collected by filtration and washed with water. 17 g of 6-hydroxy-2-methylbenzoxazole was obtained.

PREPARATION EXAMPLE 2

Synthesis of 6-Hexadecyloxy-2-methylbenzoxazole (o-alkylation)

A mixture of 18.0 g of 6-hydroxy-2-methylbenzoxazole obtained in Preparation Example 1, 36.6 g of 1-bromohexadecane, 24.0 g of potassium carbonate and 120 ml of N,N-dimethylformamide was stirred at 90° C. for 4.5 hours. The reaction solution was filtered to remove solids and the filtrate was poured into 500 ml of methanol to precipitate crystals. These crystals were collected by filtration. 45.0 g of 6-hexadecyloxy-2-methylbenzoxazole was obtained.

PREPARATION EXAMPLE 3

Synthesis of 2-Acetylamino-5-hexadecyloxyphenol (opening of oxazole ring)

A mixture of 111 g of 6-hexadecyloxy-2-methylbenzoxazole obtained in Preparation Example 2, 1,300 ml of ethanol, 110 ml of 35% hydrochloric acid and 550 ml of water was stirred at 55°–60° C. for 4 hours. The reaction solution was cooled to precipitate crystals, and the crystals were collected by filtration. 113 g of 2-acetylamino-5-hexadecyloxyphenol was obtained.

PREPARATION EXAMPLE 4

Synthesis of 2-Acetylamino-4-tert-butyl-5-hexadecyloxyphenol (nuclear alkylation)

A mixture of 30.0 g of 2-acetylamino-5-hexadecyloxyphenol, 20.0 g of Amberlyst 15 (produced by Rohm & Haas Co., U.S.A.) and 300 ml of toluene was stirred while heating at 80°–90° C., during which isobutene was bubbled therethrough for 5 hours. The reaction solution was filtered to remove solids and the filtrate was condensed. On adding 350 ml of n-hexane to the residue, crystals precipitated. The crystals were collected by filtration. 23.5 g of 2-acetylamino-4-tert-butyl-5-hexadecyloxyphenol was obtained.

PREPARATION EXAMPLE 5

Synthesis of 2-Amino-4-tert-butyl-5-hexadecyloxyphenol Hydrochloric Acid Salt (deacetylation)

A mixture of 23.0 g of 2-acetylamino-4-tert-butyl-5-hexadecyloxyphenol obtained in Preparation Example 4, 120 ml of ethanol and 96 ml of 35% hydrochloric acid was refluxed with stirring for 5 hours. The reaction solution was cooled to precipitate crystals. The crystals were collected by filtration. 23.2 g of 2-amino-4-tert-butyl-5-hexadecyloxyphenol was obtained.

PREPARATION EXAMPLE 6

Synthesis of 4-tert-Butyl-5-hexadecyloxy-2-[2-(2-methoxyethoxy)-5-nitrobenzenesulfonylamino]phenol A mixture of 4.4 g of 2-amino-4-tert-butyl-5-hexadecyloxyphenol hydrochloric acid salt obtained in Preparation Example 5 and 3.1 g of 2-(2-methoxyethoxy)-5-nitrobenzenesulfonyl chloride was dissolved in 12 ml of N,N-dimethylacetamide, to which 2.5 ml of pyridine was further added. The resulting mixture was then stirred at 25° C. for 1 hour. On pouring the reaction solution in diluted hydrochloric acid, oily products precipitated. On adding 30 ml of methanol, the oily product crystallized. These crystals were collected by filtration. Yield: 4.5 g.

PREPARATION EXAMPLE 7

Synthesis of 2-[5-Amino-2-(2-methoxyethoxy)benzenesulfonylamino]-4-tert-butyl-5-hexadecyloxyphenol The compound obtained in Preparation Example 6 in the amount of 10 g was dissolved in 60 ml of ethanol, and about 0.5 g of a 10% palladium-carbon catalyst was added. Thereafter, hydrogen was introduced at 55 kg/cm$^2$ and the above-prepared mixture was stirred at 60° C. for 6 hours. The catalyst was removed while the mixture was still hot, and the mixture was allowed to cool whereupon crystals precipitated. The crystals were collected by filtration. Yield: 7.5 g.

PREPARATION EXAMPLE 8

Synthesis of 2-Acetylamino-4-(α,α-dimethylbenzyl)-5-hexadecyloxyphenol

In 150 ml of toluene was dissolved 20 g of 2-acetylamino-5-hexadecyloxyphenol obtained in Preparation Example 3, and it was then heated at 80°–90° C. together with 8 g of Amberlyst 15 (produced by Rohm & Haas Co.). To this mixture was added dropwise 30 ml of α-methylstyrene, and the resulting mixture was heated as it is for about 7 hours. After the reaction was completed, Amberlyst 15 was removed by filtration and the filtrate was condensed. After the addition of methanol, the condensed filtrate was cooled with ice whereupon the desired product precipitated. The product was collected by filtration and washed well with methanol. Yield: 6.6 g.

PREPARATION EXAMPLE 9

Synthesis of 2-Amino-4-(α,α-dimethylbenzyl)-5-hexadecyloxyphenol Hydrochloric Acid Salt A mixture of 6.4 g of the compound obtained in Preparation Example 8, 45 ml of ethanol and 30 ml of concentrated hydrochloric acid was refluxed for 3 hours. After the reaction was completed, the reaction solution was allowed to cool whereupon crystals precipitated. These crystals were collected by filtration. Yield: 6.1 g.

PREPARATION EXAMPLE 10

Synthesis of 2-Acetylamino-4-(1-ethyl-1-methylpentyl)-5-hexadecyloxyphenol

A mixture of 250 ml of 2-acetylamino-5-hexadecyloxyphenol, 50 ml of 2-ethyl-1-hexane, 100 g of Amberlyst 15 and 750 ml of toluene was refluxed at 80° C. for 4 hours. Thereafter, Amberlyst 15 was removed by filtration and the toluene was distilled off from the filtrate. To the residue was added 150 ml of hexane, and the resulting mixture was cooled with ice for 8 hours. Crystals formed were collected by filtration, washed with hexane and dried with air. Yield: 6.0 g.

PREPARATION EXAMPLE 11

Synthesis of 2-Amino-4-(1-ethyl-1-methylpentyl)-5-hexadecyloxyphenol Hydrochloric Acid Salt To 6 g of 2-acetamido-4-(1-ethyl-1-methylpentyl)-5-hexadecyloxyphenol were added 30 ml of ethanol and 25 ml of concentrated hydrochloric acid, and the resulting mixture was heated on a steam bath for 4 hours. Thereafter, the reaction solution was cooled with ice whereupon it separated into two layers. The oil layer was separated and dried under reduced pressure. Yield: 3.5 g.

PREPARATION EXAMPLE 12

Synthesis of Compound C-1

In 100 ml of N,N-dimethylacetamide was dissolved 11.6 g of 2-amino-4-tert-butyl-5-hexadecyloxyphenol hydrochloric acid salt, and 12 ml of pyridine was added thereto. Then, 20 g of 5-(3-chlorosulfonylbenzenesulfonylamino)-2-(N-tert-butylsulfamoyl)-4-(2-methylsulfamoyl-4-nitrophenylazo)-1-naphthol was added. The resulting mixture was stirred for 1 hour and poured into 500 ml of ice water. Precipitates were recrystallized from an isopropyl alcohol-acetonitrile (1:1) mixed solvent. 6.8 g of Compound C-1 was obtained.

PREPARATION EXAMPLE 13

Synthesis of Compound C-2

Compound C-2 was produced in the same manner as in Preparation Example 12 from 2-amino-4-tert-butyl-5-hexadecyloxyphenol hydrochloric acid salt and 5-(3-chlorosulfonylbenzenesulfonylamino)-2-(N,N-diisopropylsulfamoyl)-4-(2-methylsulfonyl-4-nitrophenylazo)-1-naphthol.

PREPARATION EXAMPLE 14

Synthesis of Compound C-3

Compound C-3 was produced in the same manner as in Preparation Example 12 from 2-amino-4-tert-butyl-5-hexadecyloxyphenol hydrochloric acid salt and 5-(3-chlorosulfonylbenzenesulfonylamino)-2-[N,N-bis(2-ethoxyethyl)sulfamoyl]-4-(2-methylsulfonyl-4-nitrophenylazo)-1-naphthol.

PREPARATION EXAMPLE 15

Synthesis of Compound C-11

In 100 ml of N,N-dimethylacetamide were dissolved 31.5 g of 2-[5-amino-2-(2-methoxyethoxy)benzenesulfonylamino]-4-tert-butyl-5-hexadecyloxyphenol and 39.1 g of 5-(3-chlorosulfonylbenzenesulfonylamino)-4-(2-methylsulfonyl-4-nitrophenylazo)-1-naphthol, and 21 ml of pyridine was added thereto. After the mixture was stirred for 80 minutes, 250 ml of methanol and 100 ml of water were added. A resinous product precipitated and solidified in a short time, and it was thus separated by filtration. It was then recrystallized from a toluene-methanol-water (16:4:3) mixed solvent, and 41.5 g of Compound C-11 was obtained.

Short wavelength magenta DRR compounds having a group represented by the following formula $M_1$-(I) as the "Col" have been found according to this invention.

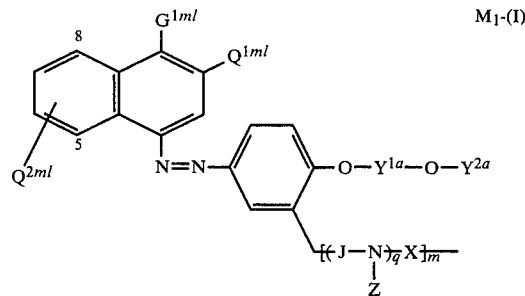

wherein $Q^{1ml}$ is a hydrogen atom, a halogen atom, a sulfamoyl group represented by $-SO_2NY^{3ml}Y^{4ml}$ (wherein $Y^{3ml}$ is hydrogen, an alkyl group or a substituted alkyl group; $Y^{4ml}$ is hydrogen or $Y^{4m1}$; $Y^{4ml}$ is an alkyl group, a substituted alkyl group, an alkenyl group, a cycloalkyl group, an aralkyl group (e.g., benzyl), a substituted aralkyl group (e.g., substituted benzyl), an aryl group (e.g., phenyl) or a substituted aryl group (e.g., substituted phenyl); and $Y^{3ml}$ and $Y^{4ml}$ may combine together directly or through an oxygen atom to form a ring), $-SO_2Y^{5ml}$ ($Y^{5ml}$ is an alkyl group, a substituted alkyl group or an aralkyl group), a carboxyl group, $-COOY^{6ml}$ (wherein $Y^{6ml}$ is an alkyl group, a substituted alkyl group, a phenyl group or a substituted phenyl group), or $-CONY^{3ml}Y^{4ml}$ (wherein $Y^{3ml}$ and $Y^{4ml}$ are the same as defined above);

$Q^{2ml}$ is positioned at the 5- or 8-position relative to $G^{1ml}$ and it represents a hydroxy group, $-NH-COY^{4aml}$ or $-NHSO_2Y^{aml}$ (wherein $Y^{4aml}$ is the same as defined above);

$Y^{1a}$ is defined as $Y^{1a}$ in the formula C-(II);

$Y^{2a}$ is defined as $Y^{2a}$ in the formula C-(II);

$G^{1ml}$ is a hydroxy group or its salt, or a group which gives a hydroxy group by hydrolysis; and m, q, J, Z and X are the same as defined in formula C-(I).

Representative examples of $G^{1ml}$ are the same as listed for G.

Where $Q^{1ml}$ is a sulfamoyl group having the formula: $-SO_2NY^{3ml}Y^{4ml}$, $Y^{3ml}$ is preferably hydrogen, an alkyl group containing from 1 to 8 carbon atoms, and preferably containing from 1 to 4 carbon atoms, or a substituted alkyl group, the alkyl residue of which contains from 1 to 8 carbon atoms, and preferably from 1 to 4 carbon atoms, $Y^{4ml}$ is preferably hydrogen, an alkyl group containing from 1 to 8 carbon atoms, and preferably 1 to 4 carbon atoms, a substituted alkyl group, the alkyl residue of which contains from 1 to 8 carbon atoms, and preferably from 1 to 4 carbon atoms, an alkenyl group containing from 1 to 8 carbon atoms, and preferably from 1 to 4 carbon atoms, a cycloalkyl group containing from 3 to 8 carbon atoms, and preferably from 5 to 8 carbon atoms, a benzyl group, a substituted benzyl group containing from 7 to 12 carbon atoms, a phenyl group or a substituted phenyl group containing from 6 to 9 carbon atoms; and $Y^{3ml}$ and $Y^{4ml}$ may be bound together directly or through oxygen to form a 5- or 6-membered ring.

Embodiments wherein (1) $Y^{3ml}$ and $Y^{4ml}$ are both hydrogen, (2) one of $Y^{3ml}$ and $Y^{4ml}$ is hydrogen and the other is an alkyl group containing from 1 to 4 carbon atoms, and (3) $Y^{3ml}$ and $Y^{4ml}$ are both alkyl groups containing from 1 to 4 carbon atoms are particularly preferred, since such compounds are inexpensive, easily available in the market and excellent in transferability.

The same considerations apply to the group: —CONY$^{3ml}$Y$^{4ml}$.

The group —SO$_2$Y$^{5ml}$, Y$^{5ml}$ is preferably an alkyl group containing from 1 to 8 carbon atoms, a substituted alkyl group, the alkyl portion of which contains from 1 to 8 carbon atoms, or a benzyl group. In particular, an alkyl group containing 1 to 4 carbon atoms and a benzyl group are preferred from the points of low cost, easy availability and good transferability.

Preferred examples of $Y^{6ml}$ in the group: —COOY$^{6ml}$ are an alkyl group containing from 1 to 8 carbon atoms, and preferably from 1 to 4 carbon atoms, a substituted alkyl group, the alkyl residue of which contains from 1 to 8 carbon atoms, and preferably 1 to 4 carbon atoms, a phenyl group and a substituted phenyl group having 6 to 9 carbon atoms.

Examples of substituents for the substituted alkyl groups in $Y^{3ml}$ to $Y^{6ml}$ and $Y^{4aml}$ are a cyano group, an alkoxy group, a hydroxyl group, a carboxyl group, a sulfo group, a tetrahydrofurfuryl group and the like (a phenyl group as a substituent is not preferred).

Examples of substituents for the substituted phenyl groups in $Y^{4ml}$, $Y^{4aml}$ and $Y^{6ml}$ are a hydroxy group, a halogen atom, a carboxy group, a sulfo group, a sulfamoyl group, an alkyl group, an alkoxy group and the like.

The substituted benzyl group of $Y^{4ml}$ preferably contains one or two substituents. Examples of such substituents are a hydroxy group, a halogen atom, a carboxy group, a sulfo group, a sulfamoyl group, an alkyl group, an alkoxy group, a methylenedioxy group and the like. Preferred among them are a hydroxy group, an alkoxy group containing 1 to 4 carbon atoms, and a methylenedioxy group. Examples of such substituted benzyl groups are an o-, m- or p-hydroxybenzyl group, an o-, m- or p-methoxybenzyl group, a 3-hydroxy-4-methoxybenzyl group, a 4-hydroxy-3-methoxybenzyl group, a 2-hydroxy-3-methoxybenzyl group, a 2,5-dimethoxybenzyl group, a 3,4-dimethoxybenzyl group, a methylenedioxybenzyl group, etc.

Preferred short wavelength magenta DRR compounds having a group of the formula M$_1$-(I) are those as described in the above-mentioned formula (II).

Of the short wavelength magenta DRR compounds, those compounds having a group represented by formula M$_1$-(II) or formula M$_1$-(III) as the "Col" are preferred.

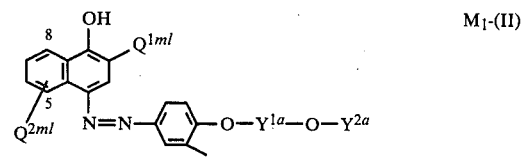

M$_1$-(II)

$$\text{OH} \quad Q^{1ml}$$
$$Q^{2ml} \quad N=N-\!\!\!\bigcirc\!\!\!-O-Y^{1a}-O-Y^{2a}$$

M$_1$-(III)

$$\text{OH} \quad Q^{1ml}$$
$$Q^{2ml} \quad N=N-\!\!\!\bigcirc\!\!\!-O-Y^{1a}-O-Y^{2a}$$
$$SO_2-NH-\!\!\!\bigcirc\!\!\!-O-Y^{1b}-O-Y^{2b}$$

wherein $Q^{1ml}$, $Q^{2ml}$, $Y^{1a}$ and $Y^{2a}$ are the same as defined in formula M$_1$-(I), and $Y^{1b}$ and $Y^{2b}$ are respectively the same as $Y^{1a}$ and $Y^{2a}$.

Representative examples of short wavelength magenta DRR compounds of this invention are shown below.

Compound M$_1$-1

Structure with OH, SO$_2$N(Y$^3$)(Y$^4$), CH$_3$SO$_2$NH, N=N—⌬—OCH$_2$CH$_2$OCH$_3$, SO$_2$NH—⌬—OH, O(CH$_2$)$_{15}$CH$_3$, CH$_3$—C(CH$_3$)—CH$_3$ wherein $Y^3 = Y^4 = C_2H_5$.

Compound M$_1$-2

In Compound M$_1$-1, $Y^3 = CH_3$ and $Y^4 = H$.

Compound M$_1$-3

In Compound M$_1$-1, $Y^3 = C_2H_5$ and $Y^4 = H$.

Compound M$_1$-4

In Compound M$_1$-1, $Y^3 = CH(CH_3)_2$ and $Y^4 = H$.

Compound M$_1$-5

In Compound M$_1$-1, $Y^3 = Y^4 = C_3H_7$—n.

Compound M$_1$-6

In Compound M$_1$-1, $Y^3 + Y^4 = -(CH_2)_4-$.

Compound M$_1$-7

In Compound M$_1$-1, $Y^3 = C_6H_5$ and $Y^4 = H$.

Compound M$_1$-8

In Compound M$_1$-1, $Y^3 = Y^4 = CH_3$.

Compound M$_1$-9

In Compound M$_1$-1, $Y^3 = Y^4 = C_4H_9(n)$.

Compound M$_1$-10

In Compound M$_1$-1, $Y^3 = CH_2CH_2OCH_3$ and $Y^4 = H$.

Compound M$^1$-11

In Compound M$_1$-1, $Y^3 =$

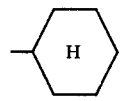

and $Y^4=H$.

Compound $M_1$-12

In Compound $M_1$-1, $Y^3=C_6H_{13}$—n and $Y^4=H$.

Compound $M_1$-13

In Compound $M_1$-1, $Y^3=C(CH_3)_3$ and $Y^4=H$.

Compound $M_1$-14

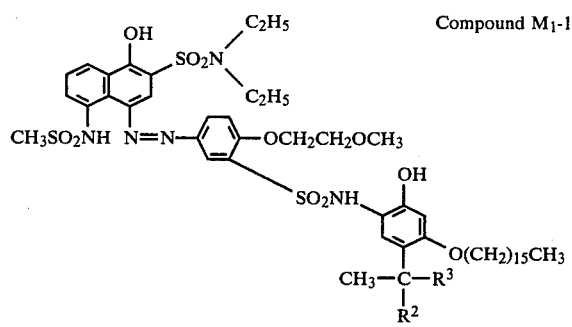

wherein $R^2=CH_3$ and $R^3=C_6H_5$.

Compound $M_1$-15

In Compound $M_1$-14, $R^2=CH_3$ and $R^3=C_2H_5$.

Compound $M_1$-16

In Compound $M_1$-14, $R^2=CH_3$ and $R^3=CH_2$—$C(CH_3)_3$.

Compound $M_1$-17

In Compound $M_1$-14, $R^2=C_2H_5$ and $R^3=C_4H_9$—n.

Compound $M_1$-18

In Compound $M_1$-14, $R^2=CH_3$ and $R^3=H$.

Compound $M_1$-19

In Compound $M_1$-14, $R^2=$

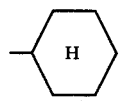

and $R^3=CH_3$.

Compound $M_1$-20

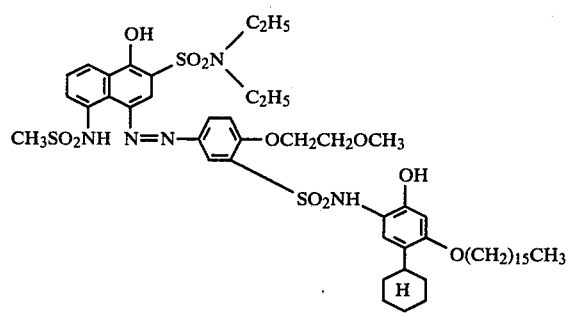

Compound $M_1$-21

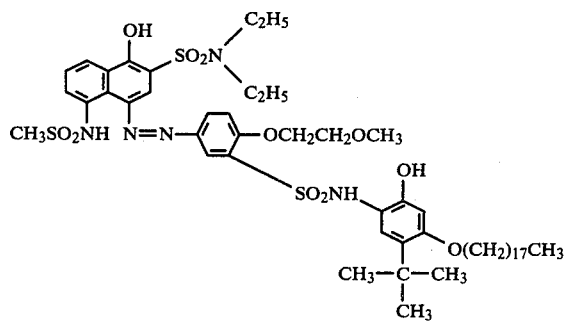

Compound $M_1$-22

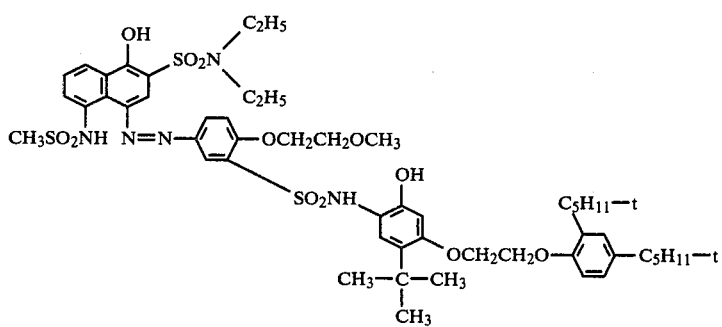

-continued
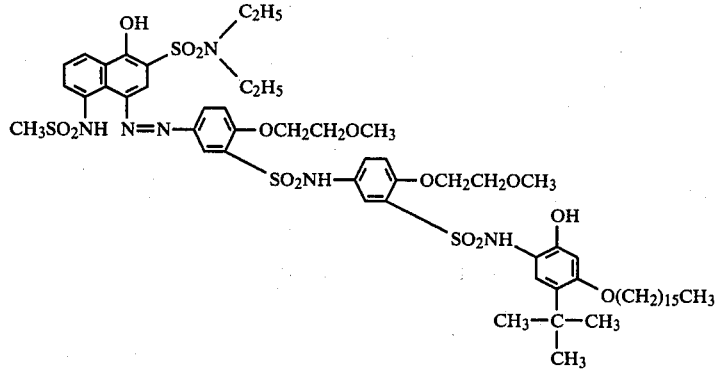
Compound M₁-23
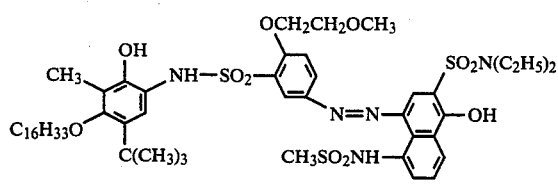
Compound M₁-24
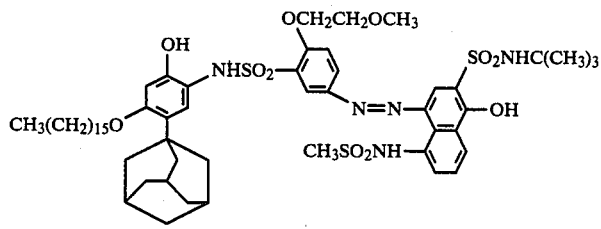
Compound M₁-25
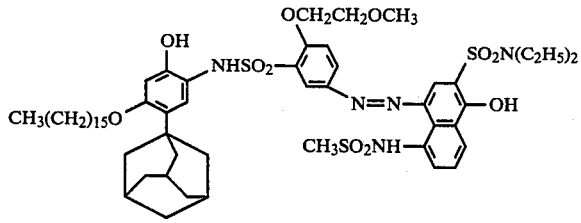
Compound M₁-26
Magenta DRR compounds of this invention which are included in formula (I) but not in compounds having a group of formula M₁-(I) are as follows:
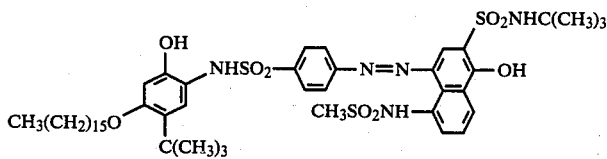
Compound M-1
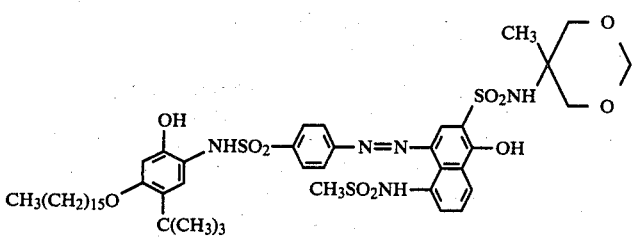
Compound M-2

-continued

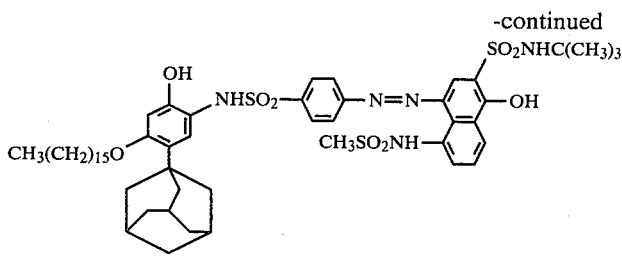

Compound M-3

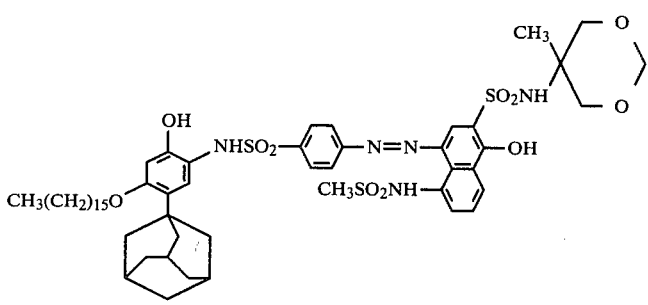

Compound M-4

In an embodiment wherein the compound having a group of formula $M_1$-(I) and the compound having a group of formula $M_2$-(I) are used in combination with each other, both compounds are incorporated in the same layer, which is in turn overlaid on a silver halide emulsion layer, in a surface-surface relation. It is also possible that a layer containing the compound having a group of formula $M_1$-(I) and a layer containing the compound having a group of formula $M_2$-(I) are separately produced and they are overlaid on at least one silver halide emulsion layer.

The above silver halide emulsion layer which is used in combination with the compounds having groups of formula $M_1$-(I) and formula $M_2$-(I) is preferably a green-sensitive silver halide emulsion layer.

The incorporation of the compounds having groups of formula $M_1$-(I) and formula $M_2$-(I) described hereinafter in the same layer produces excellent effects, for example, an increase in solubility and an increase in stability of emulsion.

The compound having a group of formula $M_1$-(I) and the compound having a group of formula $M_2$-(I) may be mixed in any desired ratio within the range that no color reproduction is deteriorated. The ratio of the compound having a group of formula $M_1$-(I) to the compound having a group of formula $M_2$-(I) is preferably about 1:99 to 99:1, and more preferably about 30:70 to 99:1. The particularly preferred ratio of the compound having a group of formula $M_1$-(I) to the compound having a group of formula $M_2$-(I) is about 50:50 to 99:1.

The short wavelength magenta DRR compounds can generally be synthesized by the condensation of sulfonyl halide of azo dye $M_1$-(IV) and o-aminophenyl derivatives $M_1$-(V) containing various organic ballast groups, e.g.,

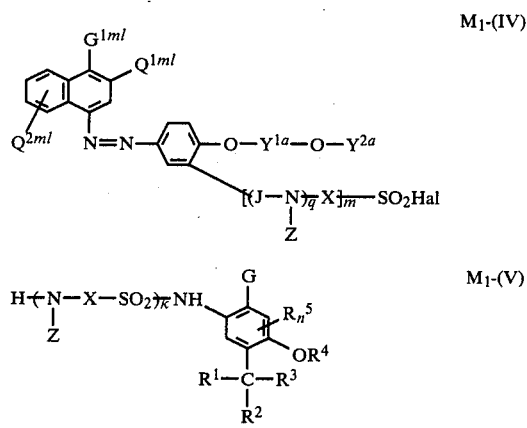

wherein Hal represents a halogen atom; where $m=0$, k is 0 or 1 and where $m=1$, k is 0; and the other symbols are the same as defined in formulae C-(I) and $M_1$-(I).

The above condensation reaction can be carried out in the same manner as described for the synthesis of the compound of formula C-(I).

A useful intermediate for the synthesis of the compound of formula $M_1$-(I): Diazo Compound $M_1$-(C) can be synthesized, for example, by the following method:

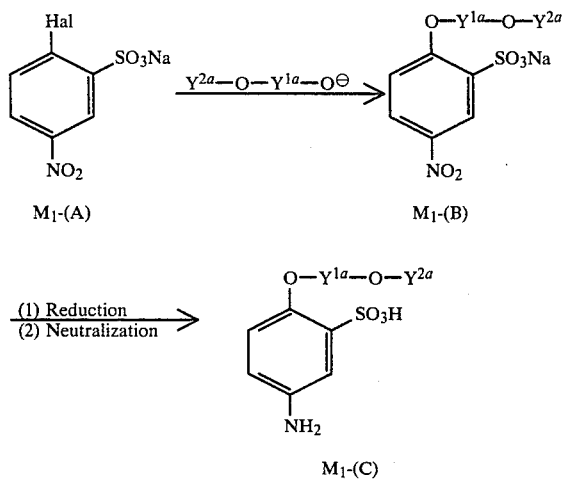

M₁-(C)

wherein Hal represents a halogen atom (in particular, a chlorine atom is preferred) and $Y^{1a}$ and $Y^{2a}$ are the same as defined in formula M₁-(I).

As a method for preparing Compound M₁-(B) from Compound M₁-(A), the above-mentioned method for preparing Compound (E) from Compound (D) should be referred to.

Additionally, the compound of formula M₁-(B) can be obtained by sulfonating p-13 $-(Y^{2a}-O-Y^{1a}-O)-C_6H_4-NO_2$ according to the method as described in the above listed Chemical Abstract. Chlorosulfonation of p-$(Y^{2a}-O-Y^{1a}-O)-C_6H_4-NO_2$ by chlorosulfonic acid is also possible. In this case, it is believed that the reaction proceeds through sulfonic acid (compound wherein in formula M₁-(B),Na is replaced by H).

L. F. Fieser, *Experiments in Organic Chemistry*, 3rd Ed., Chapter 26, D. C. Heath and Co. (1955) (published by Maruzen, Tokyo (1956)) shows the general equation and method to obtain sulfonyl chloride by using chlorosulfonic acid. When sulfonyl chloride (2-alkoxyalkoxy-5-nitrobenzenesulfonyl chloride) is refluxed in methanol, a methanol solution of the corresponding sulfonic acid (in formula M₁-(B), Na is replaced by H) is obtained. Treatment of the sulfonic acid with potassium acetate, potassium hydroxide, barium hydroxide, pyridine or the like provides the corresponding compounds wherein in formula M₁-(B), Na is replaced by K⊕, Ca + 178, Ba + ½, $C_5H_6N\oplus$ or the like.

The calcium salt and barium salt can be synthesized from the corresponding sodium salt by utilizing the difference in solubility thereof in water or the like.

While these derivatives of the compound of formula M₁-(B) are useful intermediates, it is preferred from the points of cost and advantages for the synthesis that the compound of formula M₁-(B) itself is used as an intermediate.

Typical methods to obtain Compound M₁-(C) by reducing the nitro group of the compound of formula M₁-(B) include a reduction using iron powder, a catalytic hydrogen addition (a Raney nickel catalyst or a palladium-carbon catalyst) and a hydrazine reduction (a Raney nickel catalyst, a palladium-carbon catalyst or an active carbon catalyst). Additionally, other methods of reducing the nitro group in the amino group are described, for example, in R. B. Wagner & H. D. Zook, *Synthetic Organic Chemistry*, Chapter 24, pp. 654–657, John Wiley, New York (1953), and S. R. Sandler & W. Karo, *Organic Functional Group Preparations*, Chapter 13, pp. 339–345, Academic Press, London (1968). These methods are also effective in synthesizing the compound of this invention.

As an example of the above methods of obtaining Compound M₁-(C) by reducing the nitro group of the compound represented by formula M₁-(B), the reduction using iron powder will be explained in greater detail.

The amount of the iron powder (preferably commercially available reduced iron) per mol of the compound of formula M₁-(B) is from about 1 mol to about 100 mols, preferably from 1 mol to about 50 mols and more preferably from about 1 mol to about 10 mols. Preferred solvents for use in this reduction reaction include water and alcohols such as methanol, ethanol and methoxyethanol. In some cases, these solvents are used in combination with each other. It is desirable that ammonium chloride be added as a reaction initiator in an amount of from about 1/100 to 1/10, preferably from about 1/100 to 1/20 of the weight of the compound of formula M₁-(B). With regard to the reaction temperature, it is desirably maintained at from about 30° C. to 150° C., and preferably at from about 50° C. to 100° C.

The thus-obtained reaction solution is filtered to remove insoluble products and, thereafter, the filtrate is poured into a non- or poor solvent (e.g., isopropylalcohol) whereupon the sodium salt of the compound of formula M₁-(C) precipitates. The neutralization of the above filtered reaction solution with concentrated hydrochloric acid provides the compound of formula M₁-(C) as the intermolecular salt thereof.

A typical method of synthesizing Compound M₁-(C) will hereinafter be explained in greater detail.

For the formation of the compound of formula M₁-(IV), a diazo component M₁-(C) is diazotized and coupled with a coupler or coupling component, compound of formula M₁-(D).

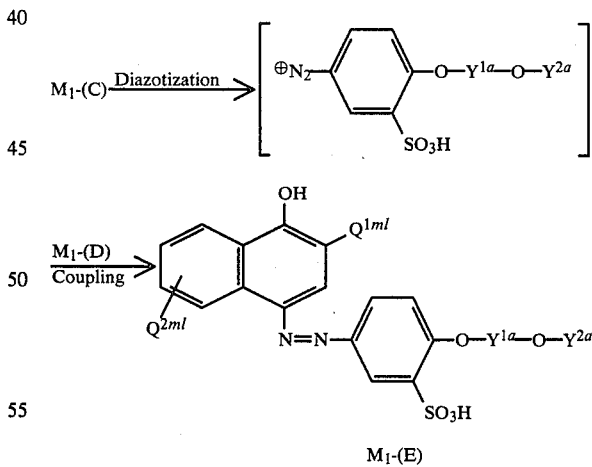

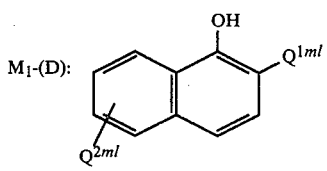

(wherein the symbols are the same as in formula M₁-(I))

The diazotization of Compound $M_1$-(C) can be carried out by the methods as described, for example, in Yutaka Hosoda, *Shin Senryo Kagaku,* pp. 114–120, Gihodo, Tokyo (1963) and Hiroshi Hotta, *Sosetsu Gosei Senryo,* pp. 114–124, Sankyo Shuppan, Tokyo (1970). Preferred among these methods is a method called the "Reversed Method".

According to the "Reversed Method", 1 mol of the diazo component $M_1$-(C), about 1 mol of sodium nitrite and about 1 mol of sodium hydroxide (or a hydroxide of an alkali or alkaline earth metal) are dissolved in water and the resulting mixture is added to a cooled mineral acid water (e.g., diluted hydrochloric acid, diluted sulfuric acid, etc.). While sodium nitrite and sodium hydroxide are preferably added in the amount as described above, they may be added in an excess amount. The thus-obtained diazonium salt solution is mixed with a solution of about 1 mol of Compound $M_1$-(D) in an organic solvent or water to effect the coupling reaction. Preferred organic solvents for use in dissolving the coupler (i.e., Compound $M_1$-(D)) include alcohols such as methanol, ethanol, 2-propanol, methoxyethanol and ethoxyethanol, carbonamides, such as N,N-dimethylacetamide and N,N-dimethylformamide and carboxylic acids such as acetic acid and propionic acid. These organic solvents can be used in combination with each other. Furthermore, Compound $M_1$-(D) can be used as the alkali aqueous solution thereof.

The coupling reaction is preferably carried out in the presence of a basic substance. Preferred basic substances include sodium acetate, potassium acetate, sodium hydroxide, potassium hydroxide, sodium carbonate, potassium carbonate and sodium hydrogencarbonate.

The details of the coupling reaction will be explained in the examples as described later, and are described generally in Hiroshi Horiguchi, *Sosetsu Gosei Senryo,* pp. 124–129, Sankyo Shuppan, Tokyo (1970), H. E. Fierz-David & L. Blangy, *Fundamental Process of Dye Chemistry,* pp. 239–297, Interscience Publishers Inc., New York (1949), and K. Venkataraman, *The Chemistry of Synthetic Dyes,* Chapter 11, Academic Press Inc., New York (1952).

To obtain the compound of formula $M_1$-(IV) (wherein m=0), the sulfonic acid group of the compound of formula $M_1$-(E) is converted in a halogenosulfonyl group. This synthesizing method will hereinafter be described by reference to the case that Hal=Cl, since this is preferred.

Chlorinating agents for use in the conversion of the sulfonic acid group of formula $M_1$-(E) in the chlorosulfonyl group include phosphorus oxychloride, phosphorus pentachloride, thionyl chloride and chlorosulfonic acid. This reaction proceeds smoothly when carboxylic acid amides such as N,N-dimethylacetamide, N,N-dimethylformamide or N-methylpyrrolidone coexist.

The amount of the chlorinating agent required is stoichiometrically determined. In many cases, however, it is desirable to use the chlorinating agent in an excessive amount (e.g., from 1.5 to 50 times the theoretical amount, and preferably from 1.5 to 10 times). In many cases, this reaction proceeds sufficiently at room temperature (about 25° C.). Where the reaction is vigorous, it is possible to cool the reaction mass to as low as about 0° C. On the other hand, where the reaction is slow, it may be heated to a range of from 25° C. to 150° C. (preferably from 25° C. to 100° C.).

Where Hal is another halogen, the compound can be synthesized by the method as described in E. Miller, *Houben-Weyls Methoden der Organishen Chemie,* Vol. IX, pp. 557–598 (1955).

PREPARATION EXAMPLE 16

Synthesis of Sodium 2-(2-Methoxyethoxy)-5-nitrobenzenesulfonate (Method 1)

To a sodium 2-methoxy-ethylate solution which had been prepared by adding 7.3 g of sodium hydride (14.6 g in the form of 50% liquid paraffin suspension) in 300 ml of 2-methoxyethanol was added with stirring 55 g of sodium 2-chloro-5-nitrobenzenesulfonate. The reaction mixture was heated with stirring at 80°–85° C. for 30 minutes on a water bath. After heat-filtration, 1.5 l of isopropyl alcohol was added to the mother liquor to precipitate crystals. These crystals were collected by filtration and washed with 100 ml of isopropyl alcohol. Yield: 59 g.

(Method 2)

A mixture of 5.2 g of sodium 2-chloro-5-nitrobenzenesulfonate, 0.6 g of manganese dioxide, 15 ml of 2-methoxyethanol, 1 ml of water and 0.95 g of sodium hydroxide was stirred at 75° C. for 40 minutes. After cooling, insoluble products were removed by filtration and the filtrate was poured into 100 ml of isopropyl alcohol. Precipitated crystals were collected by filtration. 4.8 g of sodium 2-(2-methoxyethoxy)-5-nitrobenzenesulfonate was obtained.

This compound provided the same infrared absorption spectrum as the compound as obtained in Method 1.

(Method 3)

By repeating the procedure of Method 2 except that 0.8 g of sodium silicate ($Na_2O \cdot nSiO_2$; n=about 3) was used in place of manganese dioxide, 4.8 g of sodium 2-(2-methoxyethoxy)-5-nitrobenzenesulfonate was obtained. $Na_2O \cdot nSiO_2$ (wherein n=about 1, about 2 or about 2.5) provided the same results.

This compound provided the same infrared absorption spectrum as the compound as obtained in Method 1.

PREPARATION EXAMPLE 17

Synthesis of Sodium 2-(2-Ethoxyethoxy)-5-nitrobenzenesulfonate

To a sodium 2-ethoxy-ethylate solution which had been produced by adding 7.3 g of sodium hydride (14.6 g in the form of 50% liquid paraffin suspension) to 300 ml of 2-ethoxyethanol was added 55 g of sodium 2-chloro-5-nitrobenzenesulfonate. This reaction mixture was refluxed for 30 minutes while the temperature was kept at 80°–85° C. After the reaction was completed, insoluble products were removed by filtration and thereafter 150 ml of ethyl cellosolve was distilled off under reduced pressure from the filtrate. To the condensed solution 300 ml of isopropyl alcohol was added, and the resulting mixture was cooled with ice. Precipitated crystals were collected by filtration, washed with 100 ml of isopropyl alcohol, and dried by air. Yield: 33 g.

By repeating the procedure of Method 2 or 3 of Preparation Example 16 except that 2-ethoxyethanol was used in place of 2-methoxyethanol, the same compound was obtained.

PREPARATION EXAMPLE 18

Synthesis of Sodium 2-(2-Propoxyethoxy)-5-nitrobenzenesulfonate

A mixture of 26.0 g of sodium 2-chloro-5-nitrobenzenesulfonate and 5.0 g of sodium silicate ($Na_2O \cdot nSiO_2$; n=about 3) was suspended in 120 ml of 2-propoxyethanol and while stirring the suspension, a solution prepared by dissolving 5.0 g of sodium hydroxide in 5 ml of water was dropwise added thereto at 65° C. over a period of 10 minutes. After the dropwise addition was completed, the resulting mixture was stirred at 65° C. for 3 hours and insoluble products were then removed by suction filtration. On allowing the filtrate to stand, solids precipitated. The solids were removed by filtration and the filtrate was condensed and dried. The addition of 100 ml of ethanol to the residue resulted in the formation of crystals. The crystals were collected by filtration, washed with isopropyl alcohol and dried at 50° C. Yield: 14.1 g.

PREPARATION EXAMPLE 19

Synthesis of Sodium 2-(2-Butoxyethoxy)-5-nitrobenzenesulfonate

By repeating the procedure of Method 2 of Preparation Example 16 except that ethyleneglycol monobutyl ether was used in place of 2-methoxyethanol, the above identified compound was obtained.

PREPARATION EXAMPLE 20

Synthesis of Sodium 5-Amino-2-(2-methoxyethoxy)benzenesulfonate

A mixture of 30 g of sodium 2-(2-methoxyethoxy)-5-nitrobenzenesulfonate obtained in Preparation Example 16, 30 g of reduced iron, 0.6 g of ammonium chloride and 60 ml of water was stirred while heating at 80°-85° C. After the reaction was completed, insoluble products were removed by filtration. After addition of 200 ml of isopropyl alcohol, the filtrate was cooled with ice. Precipitated crystals were collected by filtration, washed with 50 ml of isopropyl alcohol and dried by air. Yield: 23 g.

PREPARATION EXAMPLE 21

Synthesis of 5-Amino-2-(2-methoxyethoxy)benzenesulfonic Acid

A mixture of 20 g of sodium 2-(2-methoxyethoxy)-5-nitrobenzenesulfonate obtained in Preparation Example 16, 10 g of reduced iron, 0.4 g of ammonium chloride, 40 ml of isopropyl alcohol and 40 ml of water was stirred at 77° C. for 90 minutes. After the reaction was completed, the reaction solution was filtered to remove insoluble products. To the filtrate was added 20 ml of concentrated hydrochloric acid (36%). Precipitated crystals were collected by filtration, washed with isopropyl alcohol and dried by air. Yield: 19.6 g.

PREPARATION EXAMPLE 22

Synthesis of 5-Amino-2-(2-ethoxyethoxy)benzenesulfonic Acid

A mixture of 10 g of sodium 2-(2-ethoxyethoxy)-5-nitrobenzenesulfonate obtained in Preparation Example 17, 5 g of reduced iron, 0.2 g of ammonium chloride, 20 ml of isopropyl alcohol and 20 ml of water was stirred at 77° C. for 2 hours. After the reaction was completed, the reaction solution was filtered to remove insoluble products. To the filtrate, 10 ml of concentrated hydrochloric acid (36%) was added. Precipitated crystals were collected by filtration, washed with 30 ml of isopropyl alcohol and dried by air. Yield: 7.6 g.

PREPARATION EXAMPLE 23

Synthesis of 5-Amino-2-(2-propoxyethoxy)benzenesulfonic Acid

A mixture of 10 g of sodium 2-(2-propoxyethoxy)-5-nitrobenzenesulfonate, 5 g of reduced iron, 0.2 g of ammonium chloride, 20 ml of isopropyl alcohol and 20 ml of water was stirred at 77° C. for 2 hours. After the reaction was completed, the reaction solution was filtered to remove insoluble products. After addition of 10 ml of concentrated hydrochloric acid (36%), the filtrate was cooled. Precipitated crystals were collected by filtration and dried by air. Yield: 7.1 g.

PREPARATION EXAMPLE 24

Synthesis of 2-(N-tert-Butylsulfamoyl)-4-[4-(2-methoxyethoxy)-5-sulfophenylazo]-5methanesulfonamido-1-naphthol To a solution prepared by dissolving 1.7 g of sodium hydroxide in 80 ml of water were added 9.9 g of 5-amino-2-(2-methoxyethoxy)-benzenesulfonic acid and 10 ml of an aqueous solution of 2.8 g of sodium nitrite. A solution prepared by dissolving 18 ml of concentrated hydrochloric acid in 70 ml of water was dropwise added to the above-prepared solution. Thereafter, the mixture was stirred at 5° C. or less for 30 minutes to complete the diazo reaction (Preparation of Diazo Solution).

A mixture of 8.0 g of sodium hydroxide, 40 ml of water and 150 ml of methyl alcohol was prepared, to which 14.9 g of 2-tert-butylsulfamoyl-5-methanesulfonamido-1-naphthol was added. To this mixture was dropwise added the above-prepared diazo solution at 10° C. or less. After the dropwise addition was completed, the mixture was stirred at 10° C. or less for 30 minutes, and 20 ml of concentrated hydrochloric acid was added thereto. Precipitated crystals were collected by filtration, washed with 200 ml of acetone and dried by air. Yield: 19 g.

PREPARATION EXAMPLES 25 TO 34

In an analogous manner as in Preparation Example 24, the compounds as illustrated in Table $M_1$-1 below were synthesized.

TABLE $M_1$-1

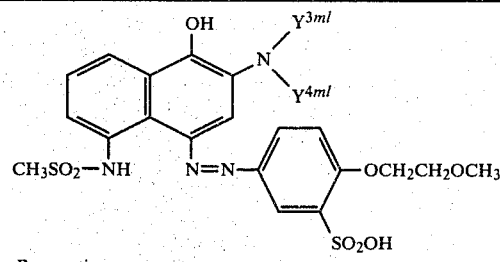

| Preparation Example | $Y^{3ml}$ | $Y^{4ml}$ |
|---|---|---|
| 25 | —CH$_3$ | H |
| 26 | —C$_2$H$_5$ | H |
| 27 | —CH(CH$_3$)$_2$ | H |
| 28 | —C$_2$H$_5$ | —C$_2$H$_5$ |
| 29 | —C$_3$H$_7$—(n) | —C$_3$H$_7$—(n) |
| 30 | —(CH$_2$)$_4$—* | |
| 31 | —C$_6$H$_5$ | H |

TABLE M₁-1-continued

| Preparation Example | $Y^{3ml}$ | $Y^{4ml}$ |
|---|---|---|
| 32 | —CH₃ | —CH₃ |
| 33 | —C₄H₉—(n) | —C₄H₉—(n) |
| 34 | —CH₂CH₂OCH₃ | H |

*$Y^{3ml}$ and $Y^{4ml}$ together combine to form —(CH₂)₄—

PREPARATION EXAMPLE 35

Synthesis of 2-(N-tert-Butylsulfamoyl)-4-[4-(2-methoxyethoxy)-5-chlorosulfonylphenylazo]-5-methanesulfonamido-1-naphthol To a mixture of 19 g of 2-(N-tert-butylsulfamoyl)-b 4-[4-(2-methoxyethoxy)-5-sulfonylazo]-5-methanesulfonamido-1-naphthol obtained in Preparation Example 24, 100 ml of acetone and 20 ml of phosphorus oxychloride was dropwise added 20 ml of N,N-dimethylacetamide at 50° C. or less. After the dropwise addition, the mixture was stirred for 1 hour and gradually poured into 500 ml of ice water. Precipitated crystals were collected by filtration, washed with 50 ml of acetonitrile and dried by air. Yield: 14 g.

PREPARATION EXAMPLES 36 TO 44

In the same manner as in Preparation Example 35, the compounds as illustrated in Table M₁-2 were synthesized.

TABLE M₁-2

[Structure: naphthol with OH, SO₂N(Y³ᵐˡ)(Y⁴ᵐˡ), CH₃SO₂NH, N=N-phenyl-OCH₂CH₂OCH₃ with SO₂Cl]

| Preparation Example | $Y^{3ml}$ | $Y^{4ml}$ |
|---|---|---|
| 36 | —CH₃ | H |
| 37 | —C₂H₅ | H |
| 38 | —CH(CH₃)₂ | H |
| 39 | —C₂H₅ | —C₂H₅ |
| 40 | —C₃H₇—(n) | —C₃H₇—(n) |
| 41 | —(CH₂)₄—* | |
| 42 | —C₆H₅ | H |
| 43 | —CH₃ | —CH₃ |
| 44 | —C₄H₉—(n) | —C₄H₉—(n) |

*$Y^{3ml}$ and $Y^{4ml}$ together combine to form —(CH₂)₄—

PREPARATION EXAMPLE 45

Synthesis of Compound M₁-1

In 20 ml of acetamide were dissolved 4.4 g of 2-amino-4-tert-butyl-5-hexadecyloxyphenol hydrochloric acid salt and 6.5 g of 4-[3-chlorosulfonyl-4-(2-methoxyethoxy)phenylazo]-2-(N,N-diethylsulfamoyl)-5-methylsulfonylamino-1-naphthol, and 4.2 ml of pyridine was added thereto. After stirring at 25° C. for 1 hour, the reaction solution was poured into diluted hydrochloric acid. Precipitated solids were collected by filtration and purified by silica gel column chromatography (eluted by a chloroform-ethyl acetate (2:1) mixed solvent). Yield: 5.2 g.

PREPARATION EXAMPLES 46 TO 57

Synthesis of Compounds M₁-2 to M₁-13

Compounds M₁-2 to M₁-13 were synthesized by the same method as in Preparation Example 45, except that the substituent at the 2-position: —SO₂NY³ ᵐˡY⁴ ᵐˡ of 4-[3-chlorosulfonyl-4-(2-methoxyethoxy)phenylazo]-2-(N,N-diethylsulfamoyl)-5-methylsulfonylamino-1-naphthol was changed as illustrated in Table M₁-3.

TABLE M₁-3

| Preparation Example | $Y^{3ml}$ | $Y^{4ml}$ | Compound No. |
|---|---|---|---|
| 46 | CH₃ | H | 2 |
| 47 | C₂H₅ | H | 3 |
| 48 | CH(CH₃)₂ | H | 4 |
| 49 | C₃H₇—n | C₃H₇—N | 5 |
| 50 | —(CH₂)₄—* | | |
| 51 | C₆H₅ | H | 7 |
| 52 | CH₃ | CH₃ | 8 |
| 53 | C₄H₉—n | C₄H₉—N | 9 |
| 54 | CH₂CH₂OCH₃ | H | 10 |
| 55 | —⟨H⟩ | H | 11 |
| 56 | C₆H₁₃—n | H | 12 |
| 57 | —(CH₃)₃ | H | 13 |

*$Y^{3ml}$ and $Y^{4ml}$ together combine to form —(CH₂)₄—

PREPARATION EXAMPLE 58

Synthesis of Compound M₁-23

In the same manner as in Preparation Example 44, Compound M₁-23 was obtained from 2-[5-amino-2-(2-methoxyethoxy)benzenesulfonylamino]-4-tert-butyl-5-hexadecyloxyphenol and 4-[3-chlorosulfonyl-4-(2-methoxyethoxy)phenylazo]-2-(N,N-diethylsulfamoyl)-5-methylsulfonylamino-1-naphthol.

PREPARATION EXAMPLE 59

Synthesis of Compound M₁-14

In the same manner as in Preparation Example 44 except that the compound obtained in Preparation Example 9 was used in place of the 2-amino-4-tert-butyl-5-hexadecyloxyphenol hydrochloric acid salt, Compound M₁-14 was obtained.

PREPARATION EXAMPLE 60

Synthesis of Compound M₁-17

In the same manner as in Preparation Example 44 except that the compound obtained in Preparation Example 17 was used in place of the 2-amino-4-tert-butyl-5-hexadecyloxyphenol hydrochloric acid salt.

Long wavelength magenta DRR compounds having a group represented by formula M₂-(I) as the "Col" have been found to be suitable for use in this invention.

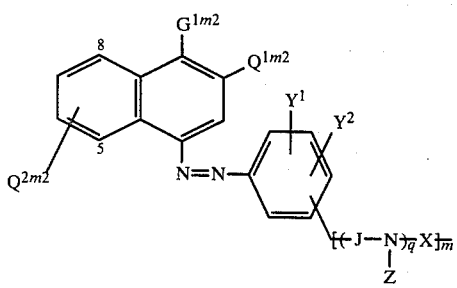

wherein m, q, J, Z and X are the same as defined in formula C-(I), $Q^{1m2}$ is hydrogen, a halogen atom, a sulfamoyl group represented by —$SO_2NY^{3m2}Y^{4m2}$ (wherein $Y^{3m2}$ is a hydrogen atom, an alkyl group, or a substituted alkyl group, $Y^{4m2}$ is a hydrogen atom or $Y^{4am2}$, $Y^{4am2}$ is an alkyl group, a substituted alkyl group, an aralkyl group or an aryl group, and $Y^{3m2}$ and $Y^{4m2}$ may be bound together directly or through an oxygen atom to form a ring), —$SO_2Y^{5m2}$ ($Y^{5m2}$ is an alkyl group, a substituted alkyl group or an aralkyl group), a carboxyl group, —$COOY^{6m2}$ ($Y^{6m2}$ is an alkyl group, a substituted alkyl group, a phenyl group or a substituted phenyl group) or —$CONY^{3m2}Y^{4m2}$ ($Y^{3m2}$ and $Y^{4m2}$ are the same as defined above);

$Q^{2m2}$ is at the 5- or 8-position relative to $G^{1m2}$ and represents a hydroxy group, —CH—$COY^{4am2}$ or —$NHSO_2Y^{4am2}$ (wherein $Y^{4am2}$ is the same as above);

$Y^1$ and $Y^2$ may be the same or different and each represents an alkyl group, a substituted alkyl group, an alkoxy groups or a substituted alkoxy group; and $G^{1m2}$ is a hydroxy group, its salt or a group giving a hydroxy group by hydrolysis.

Representative examples of $G^{1m2}$ are the same as listed for G.

Formula $M_2$-(I) is characterized in that it contains Groups $Y^1$ and $Y^2$ in the dye portion (in particular, the portion resulting from the diazo component). The simultaneous presence of the two electron donative groups have been confirmed to markedly prevent the dark fading of the transferred image as described later. This leads to a great increase in the storage stability of color images in a dark place. Where at least one of $Y^1$ and $Y^2$ is hydrogen, good storage stability of images in a dark place has not been observed.

In more detail, Y and Y may be the same or different and represent alkyl, substituted alkyl, alkoxy or substituted alkoxy. Particularly suitable are those groups which have an alkyl portion containing from 1 to 8 carbon atoms, and preferably from 1 to 4 carbon atoms. Especially suitable examples of $Y^1$ and $Y^2$ are a methyl group, an ethyl group, a methoxy group, an ethoxy group and a methoxyethoxy group. From the points of easy availability of starting materials and a diffusion rate of released dye, a methyl group and a methoxy group are particularly advantageous. Where the total number of carbon atoms of $Y^1$ and $Y^2$ is above 12, the diffusion of release dye is undesirably reduced.

$Q^{1m2}$ is a hydrogen atom, a halogen atom, a sulfamoyl group represented by —$SO_2NY^{3m2}Y^{4m2}$ (wherein $Y^{3m2}$ is a hydrogen atom, an alkyl group or a substituted alkyl group, $Y^{4m2}$ is a hydrogen atom, or $Y^{4am2}$, $Y^{4am2}$ is an alkyl group, a substituted alkyl group, an aralkyl group or an aryl group, and $Y^{3m2}$ and $Y^{4m2}$ may be bound together directly or through an oxygen atom to form a ring), —$SO_2Y^{5m2}$ (wherein $Y^{5m2}$ is an alkyl group, a substituted alkyl group or an aralkyl group), a carboxyl group, —$COOY^{6m2}$ (wherein $Y^{6m2}$ is an alkyl group, a substituted alkyl group, a phenyl group, or a substituted phenyl group), or—$CONY^{3m2}Y^{4m2}$ (wherein $Y^{3m2}$ and $Y^{4m2}$ are the same as defined above).

$Q^{2m2}$ is at the 5- or 8-position relative to $G^{1m2}$ and it represents a hydroxy group, —NH —$COY^{4am2}$ or —$NHSO_2Y^{4am2}$ (wherein $Y^{4am2}$ is the same as defined above).

Where $Q^{1m2}$ is a sulfamoyl group represented by —$SO_2NY^{3m2}Y^{4m2}$, $Y^{3m2}$ is preferably hydrogen, an alkyl group containing from 1 to 8 carbon atoms, and preferably from 1 to 4 carbon atoms or a substituted alkyl group which has an alkyl residue containing from 1 to 8carbon atoms, and preferably from 1 to 4 carbon atoms, and $Y^{4m2}$ is preferably hydrogen, an alkyl group containing from 1 to 8 carbon atoms, and preferably from 1 to 4 carbon atoms, a substituted alkyl group which has an alkyl residue containing from 1 to 8 carbon atoms, and preferably from 1 to 4 carbon atoms, an aralkyl group (e.g., a benzyl group), a phenyl group or a substituted phenyl group containing from 6 to 9 carbon atoms.

$Y^{3m2}$ and $Y^{4m2}$ may be bound together directly or through an oxygen atom to form a 5- or 6-membered ring. From the points of low cost, availability and good transferability, those are preferred in which (1) both of $Y^{3m2}$ and $Y^{4m2}$ are hydrogen, (2) at least one of $Y^{3m2}$ and $Y^{4m2}$ is hydrogen and the other is an alkyl group containing from 1 to 6 carbon atoms, and (3) $Y^{3m2}$ and $Y^{4m2}$ are alkyl groups containing from 1 to 4 carbon atoms.

The same considerations apply to —$CONY^{3m2}Y^{4m2}$.

Preferred examples of $Y^{5m2}$ in the formula: —$SO_2Y^{5m2}$ are an alkyl group containing from 1 to 8 carbon atoms, a substituted alkyl group which has an alkyl portion containing from 1 to 8 carbon atoms and an aralkyl group. In particular, an alkyl group containing from 1 to 4 carbon atoms and a benzyl group are preferred because of low cost, availability and good transferability.

Preferred examples of $Y^{6m2}$ in —$COOY_{6m2}$ are an alkyl group containing from 1 to 8 carbon atoms, and preferably from 1 to 4 carbon atoms, a substituted alkyl group which has an alkyl portion containing from 1 to 8 carbon atoms, and preferably from 1 to 4 carbon atoms, and a phenyl group and substituted phenyl groups containing from 6 to 9 carbon atoms.

Substituents for the substituted alkyl group in $Y^{3m2}$ to $Y^{6m2}$ include a cyano group, an alkoxy group, a hydroxy group, a carboxy group and a sulfo group.

Substituents for the substituted phenyl group in $Y^{6m2}$ include a hydroxy group, a halogen atom, a carboxy group, an sulfo group and a sulfamoyl group.

Preferred long wavelength magenta DRR compounds having a group of formula $M_2$-(I) are those as described in the above-mentioned formula (II).

Furthermore, preferred compounds are those having a group of formula $M_2$-(I) wherein m is O.

Representative examples of DRR compounds having a group of formula $M_2$-(I) are shown below.

Compound M₂-1
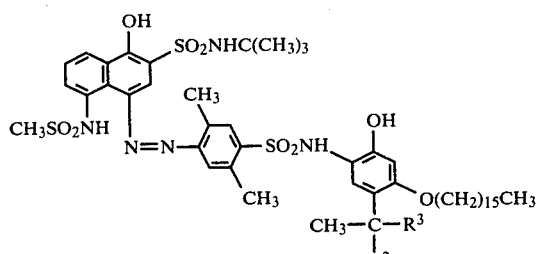
(R² = R³ = CH₃)
Compound M₂-2
  In Compound M₂-1, R² = CH₃, R³ = C₆H₅.
Compound M₂-3
  In Compound M₂-1, R² = C₂H₅, R³ = C₄H₉.
Compound M₂-4
  In Compound M₂-1, R² = CH₃, R³ = C₂H₅.
Compound M₂-5
  In Compound M₂-1, R² = C₂H₅.
Compound M₂-6
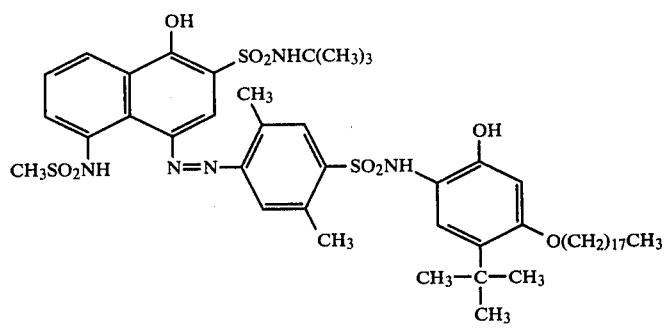
Compound M₂-7
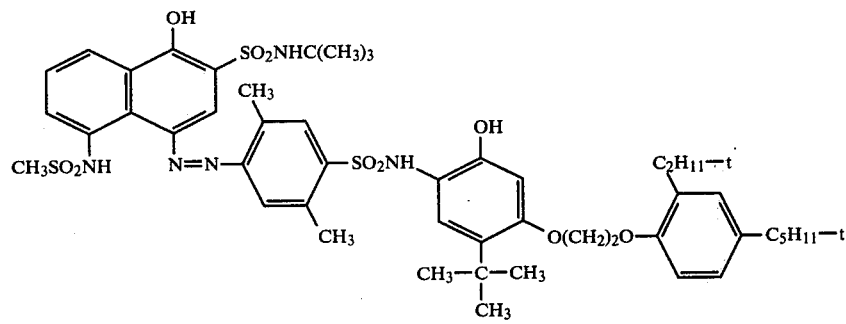
Compound M₂-8
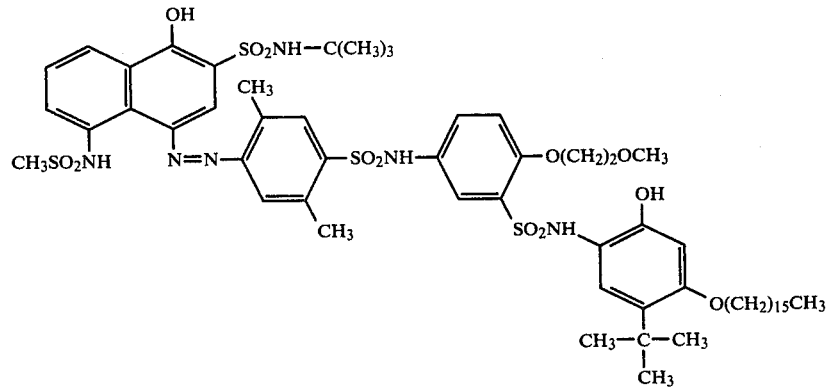
Compound M₂-9

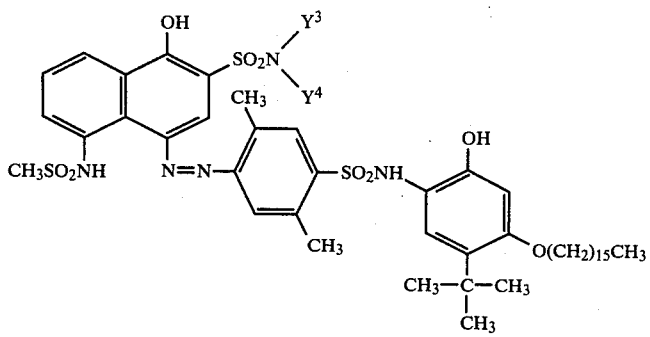

($Y^3 = Y^4 = H$)

Compound $M_2$-10

As in Compound $M_2$-9, $Y^3=H$, $Y^4=CH_3$. Further, such compounds are shown below.

| Compound | As in Structure | |
|---|---|---|
| $M_2$-11 | $M_2$-9 wherein | $Y^3 = H, Y^4 = C_2H_5$ |
| $M_2$-12 | " | $Y^3 = H, Y^4 = C_3H_7-n$ |
| $M_2$-13 | " | $Y^3 = H, Y^4 = CH(CH_3)_2$ |
| $M_2$-14 | " | $Y^3 = H, Y^4 = C_4H_9-n$ |
| $M_2$-15 | " | $Y^3 = H, Y^4 = $ —⟨cyclopentyl-H⟩ |
| $M_2$-16 | " | $Y^3 = H, Y^4 = $ —⟨cyclohexyl-H⟩ |
| $M_2$-17 | " | $Y^3 + Y^4 = -(CH_2)_2O(CH_2)_2-$ |
| $M_2$-18 | " | $Y^3 + Y^4 = -(CH_2)_5-$ |
| $M_2$-19 | " | $Y^3 + Y^4 = -(CH_2)_4-$ |
| $M_2$-20 | " | $Y^3 = Y^4 = CH_3$ |
| $M_2$-21 | " | $Y^3 = Y^4 = C_2H_5$ |
| $M_2$-22 | " | $Y^3 = Y^4 = C_3H_7-n$ |
| $M_2$-23 | " | $Y^3 = Y^4 = C_4H_9-n$ |
| $M_2$-24 | " | $Y^3 = H, Y^4 = CH_2CH_2OCH_3$ |
| $M_2$-25 | " | $Y^3 = H, Y^4 = C_6H_5$ |
| $M_2$-26 | " | $Y^3 = H, Y^4 = CH_2C_6H_5$ |
| $M_2$-27 | " | $Y^3 = H, Y^4 = -CH_2-$⟨2-OCH_3-phenyl⟩ |
| $M_2$-28 | " | $Y^3 = H, Y^4 = -CH_2-$⟨4-OCH_3-phenyl⟩ |
| $M_2$-29 | " | $Y^3 = H, Y^4 = -CH_2-$⟨tetrahydrofuryl⟩ |

Compound $M_2$-30

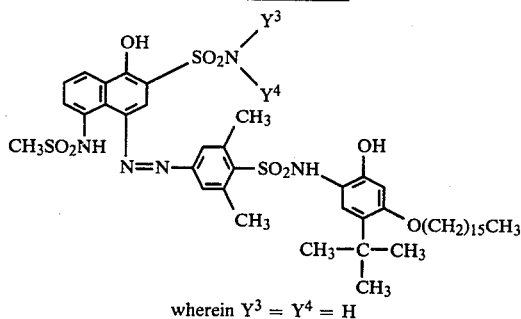

wherein $Y^3 = Y^4 = H$

| Compound | As in Structure | |
|---|---|---|
| $M_2$-31 | $M_2$-30 wherein | $Y^3 = H, Y^4 = CH_3$ |
| $M_2$-32 | " | $Y^3 = H, Y^4 = C_2H_5$ |
| $M_2$-33 | " | $Y^3 = H, Y^4 = C_3H_7-n$ |
| $M_2$-34 | " | $Y^3 = H, Y^4 = -CH(CH_3)_2$ |
| $M_2$-35 | " | $Y^3 = H, Y^4 = C_4H_9-n$ |
| $M_2$-36 | " | $Y^3 = H, Y^4 = $ —⟨cyclopentyl⟩ |
| $M_2$-37 | " | $Y^3 = H, Y^4 = $ —⟨cyclohexyl-H⟩ |
| $M_2$-38 | " | $Y^3 + Y^4 = -(CH_2)_2O(CH_2)_2-$ |
| $M_2$-39 | " | $Y^3 + Y^4 = -(CH_2)_5-$ |
| $M_2$-40 | " | $Y^3 + Y^4 = -(CH_2)_4-$ |
| $M_2$-41 | " | $Y^3 = Y^4 = CH_3$ |
| $M_2$-42 | " | $Y^3 = Y^4 = C_2H_5$ |
| $M_2$-43 | " | $Y^3 = Y^4 = C_3H_7-n$ |
| $M_2$-44 | " | $Y^3 = Y^4 = C_4H_9-n$ |
| $M_2$-45 | " | $Y^3 = H, Y^4 = CH_2CH_2OCH_3$ |
| $M_2$-46 | " | $Y^3 = H, Y^4 = C_6H_5$ |
| $M_2$-47 | " | $Y^3 = H, Y^4 = CH_2C_6H_5$ |
| $M_2$-48 | " | $Y^3 = H, Y^4 = -CH_2-$⟨2-OCH_3-phenyl⟩ |
| $M_2$-49 | " | $Y^3 = H, Y^4 = -CH_2-$⟨4-OCH_3-phenyl⟩ |
| $M_2$-50 | " | $Y^3 = H, Y^4 = CH_2-$⟨tetrahydrofuryl⟩ |
| $M_2$-51 | " | $Y^3 = H, Y^4 = C(CH_3)_3$ |

Compound $M_2$-52

[structure of Compound $M_2$-52 showing naphthalene with OH, $SO_2NHC(CH_3)_3$, $CH_3SO_2NH$, linked via N=N to dimethyl-substituted benzene with $SO_2NH$ to phenol bearing cyclohexyl and $O(CH_2)_{15}CH_3$]

Compound $M_2$-53

As in Compound $M_2$-1 wherein $R^2=CH_3$, $R^3=-CH_2C(CH_3)_3$.

Compound $M_2$-54

As in Compound $M_2$-1 wherein $R^2=CH_3$, $R^3=H$.

Compound $M_2$-55

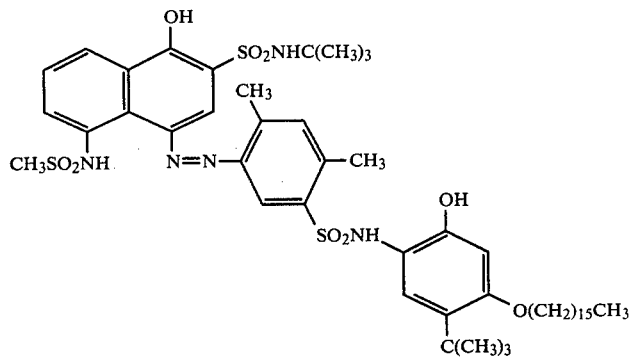
Compound M₂-56
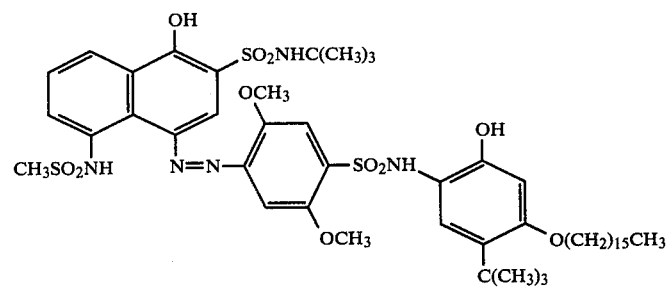
Compound M₂-57
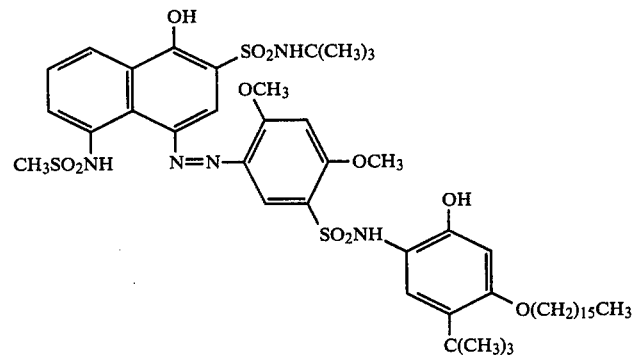
Compound M₂-58
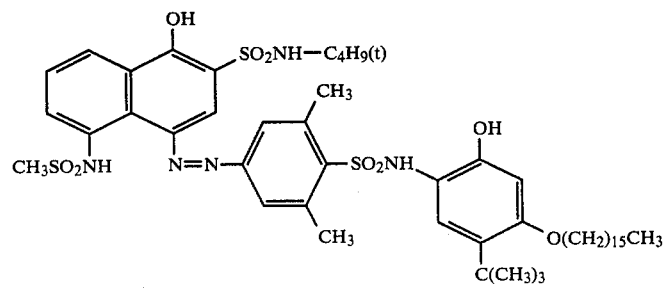
Compound M₂-59

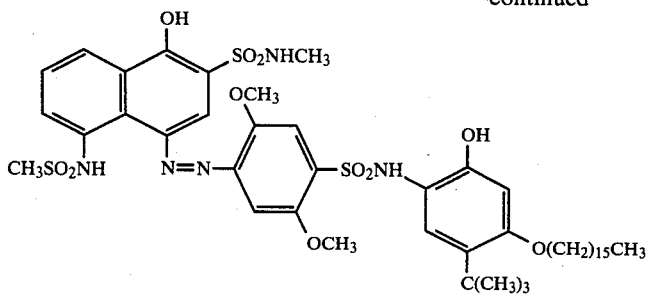

Compound M₂-60

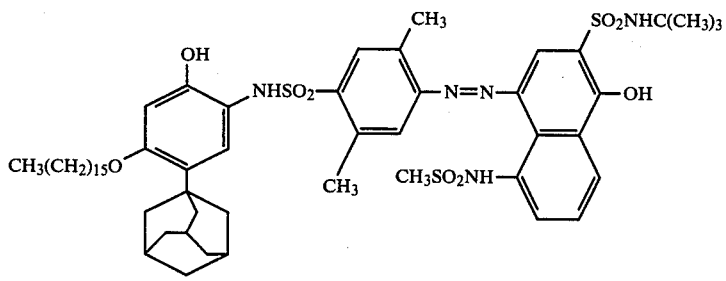

The compounds having a group of formula M₂-(I) can be synthesized by the condensation of sulfonyl halide of azo dye M₂-(II) and o-aminophenol derivatives M₂-(III) containing various organic ballast groups.

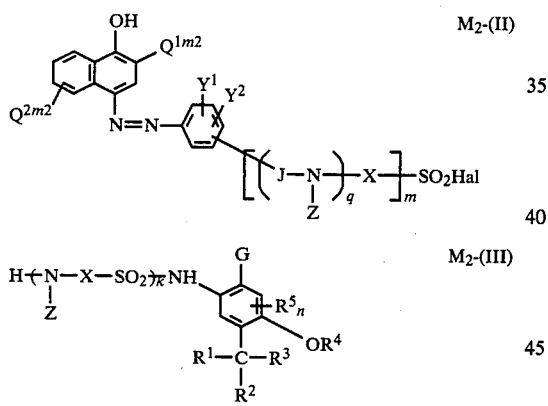

wherein Hal is a halogen atom; where m=O, k is 1 or 0 and where n=1, k is O; and the other symbols are the same as defined in formula (I) or formula M₂-(I).

This condensation reaction can be carried out by the method as described for the synthesis of the compound of formula C-(I).

The sulfonyl halide of azo dye represented by formula M₂-(II) can be synthesized as follows: an aminobenzenesulfonic acid (M₂-(A)) containing two electron donative groups is diazotized and coupled with a compound represented by formula M₂-(B) (i.e., coupler or coupling component) to provide a diazo dye (M₂-(C)), and the diazo dye is further halogenated.

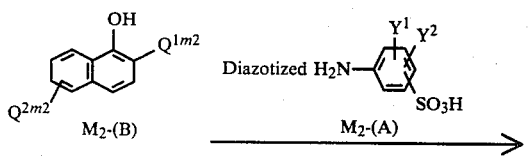

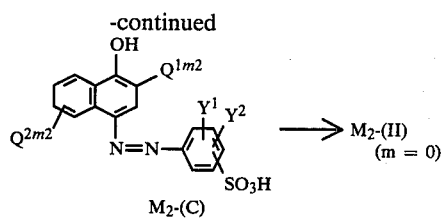

wherein the symbols are the same as defined in formula M₂(I).

The diazotization of Compound M₂-(B) can be carried out by the methods as described in that of M₁-(C). Organic solvents for use in dissolving the coupler include those described as to Compound M₁-(D). The coupling reaction is preferably carried out according to the above-mentioned method.

By using a compound having the formula as illustrated below in place of Compound M₂-(A) in the above reaction, Compound M₂-(II) can be synthesized.

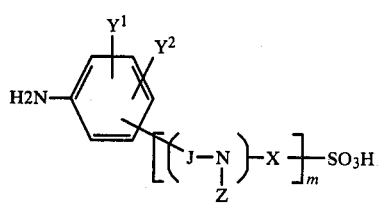

wherein the symbols are the same as in formula M₂-(I).

In obtaining the compound of formula M₂-(II), the sulfonic acid group of the compound of formula M₂-(C) is changed to a halogenosulfonyl group. This synthesis can be carried out according to the abovementioned method as to M₁-(E).

PREPARATION EXAMPLE 61

Synthesis of 2-(N-tert-Butylsulfamoyl)-4-(2,5-dimethyl-4-sulfophenylazo)-5-methanesulfonamido-1-naphthol To a solution prepared by dissolving 4 g of sodium hydroxide in 100 ml of water were added with stirring 10.5 g of 2,5-dimethyl-4-aminobenzenesulfonic acid and 3.85 g of sodium nitrite and thoroughly dissolved therein. This solution was poured at 5° C. or less in 100 ml of 2N hydrochloric acid and stirred for 30 minutes while cooling with ice.

To 5 g of sodium hydroxide were added 50 ml of water, 200 ml of methylalcohol and 18.6 g of 2-(N-tert-butylsulfamoyl) -5-methanesulfonamido-1-naphthol to prepare a solution, and this solution was added with stirring at 10° C. or less to the above-prepared diazo solution.

After stirring for 1 hour while cooling with water, 20 ml of hydrochloric acid (d=1.18) was added to precipitate crystals. These precipitated crystals were collected by filtration and then washed with 100 ml of saturated brine. Yield: 27 g; m.p.: 200° C. or more.

In the same manner as in Preparation Example 61, those compounds containing the groups as illustrated below as the substituent at the 2-position of the naphthol ring in place of the N-tert-butylsulfamoyl group can be obtained.

A sulfamoyl group, an N-methylsulfamoyl group, an N-ethylsulfamoyl group, an N-propylsulfamoyl group, an N-isopropylsulfamoyl group, an N-butylsulfamoyl group, an N-cyclopentylsulfamoyl group, an N-cyclohexylsulfamoyl group, a morpholinosulfamoyl group, a piperidinosulfamoyl group, a pyrrolidinosulfamoyl group, an N,N-dimethylsulfamoyl group, an N,N-diethylsulfamoyl group, an N,N-dipropylsulfamoyl group, an N,N-dibutylsulfamoyl group, an N-(2-methoxyethyl)sulfamoyl group, an N-phenylsulfamoyl group, an N-benzylsulfamoyl group, an N-(2-methoxybenzyl)sulfamoyl group, an N-(4-methoxybenzyl)sulfamoyl group, an N-tetrahydrofurfurylsulfamoyl group.

PREPARATION EXAMPLE 62

Synthesis of 2-(N-tert-Butylsulfamoyl)-4-(3,5-dimethyl-4-sulfophenylazo)-5-methanesulfonamido-1-naphthol To a solution prepared by dissolving 4 g of sodium hydroxide in 100 ml of water were added with stirring 10.5 g of 2,6-dimethyl-4-aminobenzenesulfonic acid and 3.85 g of sodium nitrite, and thoroughly dissolved therein. This solution was poured at 5° C. or less in 100 ml of 2 N hydrochloric acid and stirred for 30 minutes while cooling with ice.

To 50 ml of a 5% sodium hydroxide solution were added 200 ml of methyl alcohol and 18.6 g of 2-tert-butylsulfamoyl-5-methanesulfonamido-1-naphthol to prepare a solution, and this solution was added with stirring at 10° C. or less to the above-prepared diazo solution.

After stirring for 1 hour while cooling with water, 20 ml of hydrochloric acid (d=1.18) was added to precipitate crystals. These precipitated crystals were collected by filtration and washed with 100 ml of saturated brine. Yield: 32 g; m.p.: 200° C. or more.

By analogous methods as those used in Preparation Example 62, compounds containing the groups as noted below as the substituent at the 2-position of the naphthol ring can be obtained in place of the N-tert-butylsulfamoyl group.

A sulfamoyl group, an N-methylsulfamoyl group, an N-ethylsulfamoyl group, an N-propylsulfamoyl group, an N-isopropylsulfamoyl group, an N-butylsulfamoyl group, an N-cyclopentylsulfamoyl group, an N-cyclohexylsulfamoyl group, a morpholinosulfamoyl group, a piperidinosulfamoyl group, a pyrrolidinosulfamoyl group, an N,N-dimethylsulfamoyl group, an N,N-diethylsulfamoyl group, an N,N-dipropylsulfamoyl group, an N,N-dibutylsulfamoyl group, an N-(2-methoxyethyl)sulfamoyl group, an N-phenylsulfamoyl group, an N-benzylsulfamoyl group, an N-(2-methoxybenzyl)sulfamoyl group, an N-(4-methoxybenzyl)sulfamoyl group, an N-tetrahydrofurfurylsulfamoyl group.

PREPARATION EXAMPLE 63

Synthesis of 2-(N-tert-Butylsulfamoyl)-4-(2,5-dimethyl-4-chlorosulfonylphenylazo)-5-methanesulfonamido-1-naphthol To a solution prepared by adding 180 ml of acetonitrile and 35 ml of phosphorus oxychloride to 25 g of the naphthol compound as obtained in Preparation Example 61 was dropwise added 15 ml of N,N-dimethylacetamide at 60° C. or less with stirring.

After stirring at 60° C. for 3 hours, the reaction mixture was poured in 800 ml of ice water to precipitate crystals. These crystals were collected by filtration and then washed with 100 ml of acetonitrile. Yield: 19 g; m.p.: 199°–204° C.

The sulfonic acid group of the other various compounds in which the substituent at the 2-position of the naphthol ring was changed as illustrated in the final part of Preparation Example 61 was each changed to the corresponding sulfonylchloride by the method described in Preparation Example 63.

PREPARATION EXAMPLE 64

Synthesis of 2-(N-tert-Butylsulfamoyl)-4-(3,5-dimethyl-4-chlorosulfonylphenylazo)-5-methanesulfonamido-1-naphthol To a solution prepared by adding 250 ml of acetonitrile and 45 ml of phosphorus oxychloride to 30 g of the naphthol compound as obtained in Preparation Example 62 was dropwise added 15 ml of N,N-dimethylacetamide at 60° C. or less with stirring.

After stirring at 60° C. for 3 hours, the reaction mixture was poured in 1 l of ice water to precipitate crystals. These crystals were collected by filtration and then washed with 100 ml of acetonitrile. Yield: 23 g; m.p.: 197°–201° C.

The sulfonic acid group of the compound in which the substituent at the 2-position of the naphthol ring was changed as illustrated in Preparation Example 62 was changed to the corresponding sulfonylchloride by the method as described in Preparation Example 64.

PREPARATION EXAMPLE 65

Synthesis of Compound $M_2$-1

To 250 ml of N,N-dimethylacetamide were added 44.2 g of the 2-amino-4tert-butyl-5-hexadecyloxyphenol hydrochloric acid salt as obtained in Preparation Example 5 and 60.3 g of the 2-(N-tert-butylsulfamoyl)-4-(2,5-dimethyl-4-chlorosulfonylphenylazo)-5-methanesulfonamido-1-naphthol as obtained in Preparation Example 63. To the resulting mixture was dropwise added with stirring 39.5 ml of pyridine. After the dropwise addition was completed, the reaction mixture was stirred for additional 2 hours at room temperature and then dropwise added to a solution prepared by diluting 50 ml of 35% hydrochloric acid with 1 l of water. Precipitated crystals were, after filtration, recrystallized twice from methanol and twice from ethanol to obtain 39.0 g of Compound $M_2$-1.

PREPARATION EXAMPLE 66

Synthesis of Compound $M_2$-2

In the same manner as in Preparation Example 65, Compound $M_2$-2 was produced from the 2-amino-4-($\alpha,\alpha$-dimethylbenzyl)-5-hexadecyloxyphenol hydrochloric acid salt and the compound as obtained Preparation Example 63.

PREPARATION EXAMPLE 67

Synthesis of Compound $M_2$-3

In the same manner as in Preparation Example 65, Compound $M_2$-3 was produced from the 2-amino-4-(1-ethyl-1-methylpentyl)-5-hexadecyloxyphenyl hydrochloric acid salt and the compound as obtained in Preparation Example 63.

PREPARATION EXAMPLE 68

Synthesis of Compound $M_2$-8

In the same manner as in Preparation Example 65, Compound $M_2$-8 was produced from 2-[5-amino-2-(2-methoxyethoxy)benzenesulfonylamino]-4-tert-butyl-5-hexadecylphenol and the compound as obtained in Preparation Example 61.

PREPARATION EXAMPLES 69 TO 89

Synthesis of Compounds $M_2$-9 to $M_2$-29

By reacting the 2-amino-4-tert-butyl-5-hexadecyloxyphenol hydrochloric acid salt with the compounds as illustrated in the final part of Preparation Example 63 in the same manner as in Preparation Example 65, Compound $M_2$-9 to Compound $M_2$-29 were synthesized.

PREPARATION EXAMPLES 90 TO 111

Synthesis of Compounds $M_2$-30 to $M_2$-51

By reacting the 2-amino-4-tert-butyl-5-hexadecyloxyphenol hydrochloric acid salt with the compounds as illustrated in Preparation Example 64 in the same manner as in Preparation Example 65, Compounds $M_2$-30 to $M_2$-51 were obtained.

Yellow DRR compounds having a group represented by the formulae Y-(I) or Y-(II) as the "Col" have been found to be suitable for use in this invention.

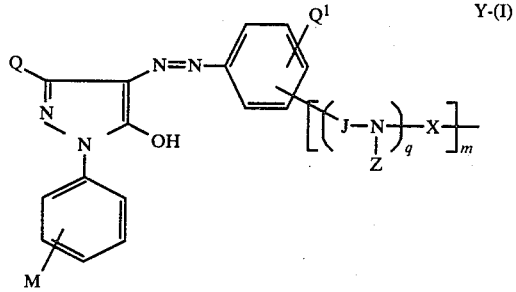

Y-(I)

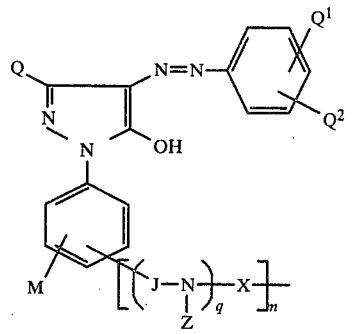

Y-(II)

wherein m, q, J, Z and X are the same as defined in formula C-(I);

Q represents a cyano group, a trifluoromethyl group or a carbamoyl group represented by $-CONY^3Y^4$ (wherein $Y^3$ is hydrogen, an alkyl group, or a substituted alkyl group, $Y^4$ is hydrogen, an alkyl group, a substituted alkyl group, an aralkyl group or an aryl group, and $Y^3$ and $Y^4$ together directly or through an oxygen atom may form a ring);

M represents hydrogen, an alkyl group, a substituted alkyl group, an alkoxy group, a substituted alkoxy group, a sulfamoyl group represented by $-SO_2NY^3Y^4$ (wherein $Y^3$ and $Y^4$ are the same as defined above), a group represented by $-COOY^6$ (wherein $Y^6$ is an alkyl group, a substituted alkyl group, a phenyl group or a substituted phenyl group) or a halogen atom;

$Q^1$ represents hydrogen, a halogen atom, a group represented by $-SO_2NY^3Y^4$ (wherein $Y^3$ and $Y^4$ are the same as defined above), a group represented by $-SO_2Y^5$ (wherein $Y^5$ is an alkyl group, a substituted alkyl group or an aralkyl group), a group represented by $-CONY^3Y^4$ (wherein $Y^3$ and $Y^4$ are the same as defined above) a group represented by $-COOY^6$ (wherein $Y^6$ is the same as defined above), an alkyl group, a substituted alkyl group, an alkoxy group, or a substituted alkoxy group; and $Q^2$ represents a cyano group, a trifluoromethyl group, a group of $-SO_2Y^5$ (wherein $Y^5$ is the same as defined above), a group represented by $-SO_2NY^3Y^4$ (wherein $Y^3$ and $Y^4$ are the same as defined above), a group represented by $-COOY^6$ (wherein $Y^6$ is the same as defined above), a group represented by $-CONY^3Y^4$ (wherein $Y^3$ and $Y^4$ are the same as defined above) or a halogen atom.

Where Q is a carbamoyl group represented by the formula $-CO-NY^3Y^4$, $Y^3$ is preferably hydrogen, an alkyl group containing from 1 to 8 carbon atoms, and preferably from 1 to 4 carbon atoms, or a substituted alkyl group which has an alkyl portion containing from 1 to 8 carbon atoms, and preferably from 1 to 4 carbon atoms; $Y^4$ is preferably hydrogen, an alkyl group containing from 1 to 8 carbon atoms, and preferably from 1 to 4 carbon atoms, a substituted alkyl group which has an alkyl portion containing from 1 to 8 carbon atoms, and preferably from 1 to 4 carbon atoms, a benzyl group, a phenyl group or a substituted phenyl group containing from 6 to 9 carbon atoms; and $Y^3$ and $Y^4$ may be bound together directly or through an oxygen atom to form a 5- or 6-membered ring.

Those cases wherein (1) $Y^3$ and $Y^4$ are both hydrogen, (2) at least one of $Y^3$ and $Y^4$ is hydrogen and the other is alkyl containing 1 to 4 carbon atoms and (3) $Y^3$ and $Y^4$ are alkyl containing 1 to 4 carbon atoms are particularly preferred, from the points of view of low cost, availability, and good transferability.

Q is especially preferred to be a cyano group from the point of view of fastness of transferred dye compound.

The alkyl group represented by M preferably contains from 1 to 8 carbon atoms, and preferably from 1 to 4 carbon atoms, and the substituted alkyl group represented by M preferably has an alkyl portion containing from 1 to 8 carbon atoms, and preferably from 1 to 4 carbon atoms. Examples of substituents for the substituted alkyl group are the same as listed for $Y^3$-$Y^5$ as described later.

The alkoxy group and the substituted alkoxy group represented by M preferably contain an alkyl portion containing from 1 to 8 carbon atoms, and more preferably from 1 to 4 carbon atoms. Examples of substituents for the substituted alkoxy group are the same as listed for $Y^3$-$Y^5$ as described herein.

Where M is a sulfamoyl group represented by the formula —$SO_2NY^3Y^4$, preferred examples of $Y^3$ and $Y^4$ are those as described in —$CONY^3Y^4$ for Q.

Preferred examples of $Y^6$ in —$COOY^6$ are an alkyl group containing from 1 to 8 carbon atoms, and preferably from 1 to 4 carbon atoms, a substituted alkyl group which has an alkyl portion containing from 1 to 8 carbon atoms, and preferably from 1 to 4 carbon atoms, a phenyl group and a substituted phenyl group containing from 6 to 9 carbon atoms.

Examples of substituents for the substituted alkyl group in $Y^3$ and $Y^5$ are a cyano group, an alkoxy group, a hydroxy group, a carboxyl group, a sulfo group and a tetrahydrofurfuryl group.

Examples of substituents for the substituted phenyl group in $Y^4$, $Y^5$ and $Y^6$ are a hydroxy group, a halogen atom, a carboxyl group, a sulfo group and a sulfamoyl group.

As the halogen atom represented by M, a chlorine atom is particularly preferred.

Where $Q^1$ or $Q^2$ is a sulfamoyl group represented by the formula —$SO_2NY^3Y^4$, preferred examples of $Y^3$ and $Y^4$ are those as described in —$CONY^3Y^4$ for Q.

The same considerations apply to the group —$CONY^3Y^4$ for $Q^1$ and $Q^2$.

Where $Q^1$ or $Q^2$ is —$SO_2Y^5$, $Y^5$ preferably is an alkyl group containing from 1 to 8 carbon atoms, a substituted alkyl group which has an alkyl portion containing from 1 to 8 carbon atoms or a benzyl group. In particular, an alkyl group containing from 1 to 4 carbon atoms and a benzyl group are preferred on the grounds that such compounds are inexpensive, easily available on the market and excellent in transferability.

Preferred examples of $Y^6$ in —$COOY^6$ for $Q^2$ are those as described in $Y^6$ for M.

Examples of substituents for the substituted alkyl group in $Y^3$ to $Y^6$ for $Q^1$ and $Q^2$ are a cyano group, an alkoxy group, a hydroxy group, a carboxyl group, a sulfo group and a tetrahydrofurfuryl group. However, a phenyl group is excluded.

Substituents for the substituted phenyl group in $Y^4$, $Y^5$ and $Y^6$ for $Q^1$ and $Q^2$ are a hydroxy group, a halogen atom, a carboxy group, a sulfo group, a sulfamoyl group, an alkyl group and an alkoxy group.

Preferred yellow DRR compounds having a group of formula Y-(I) are those as described in the abovementioned formula (II).

More preferably, the yellow DRR compounds of this invention are those having a group represented by formulae Y-(III) and Y-(IV).

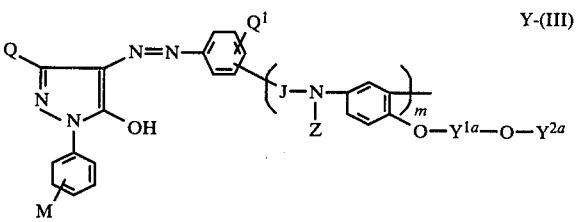

Y-(III)

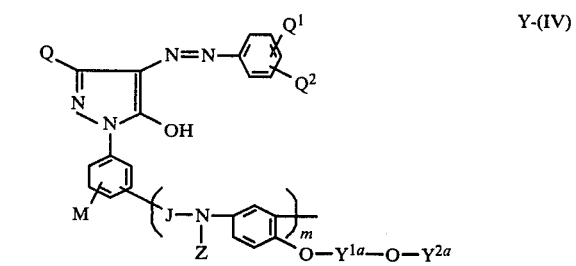

Y-(IV)

wherein Q, $Q^1$, $Q^2$, M, J, Z, q and m have the same meanings as in formula Y-(I) or Y-(II), $Y^{1a}$ and $Y^{2a}$ have the same meanings as in formula C-(II).

Representative examples of yellow DRR compounds of this invention are as follows:

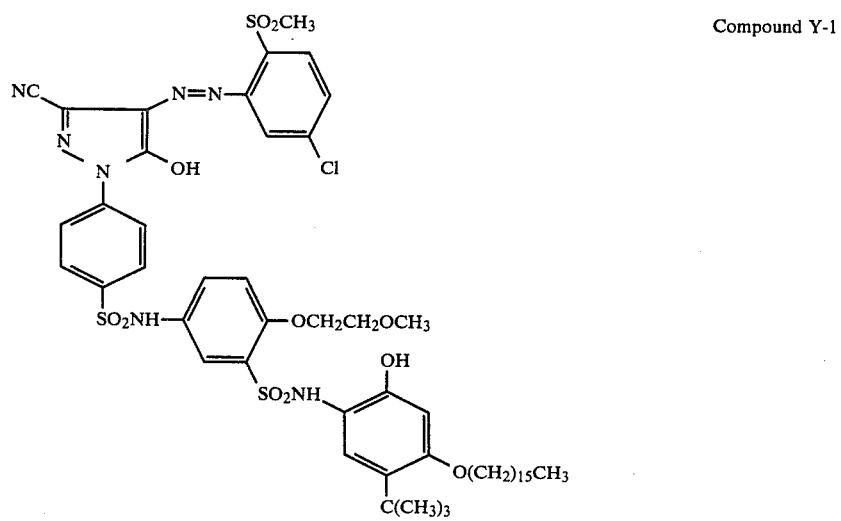

Compound Y-1

Compound Y-2
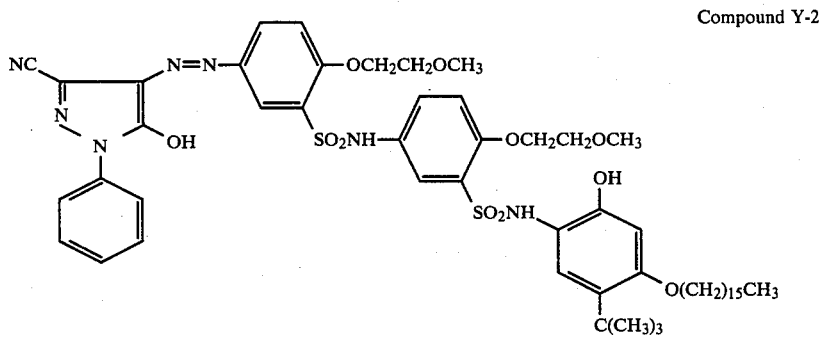
Compound Y-3
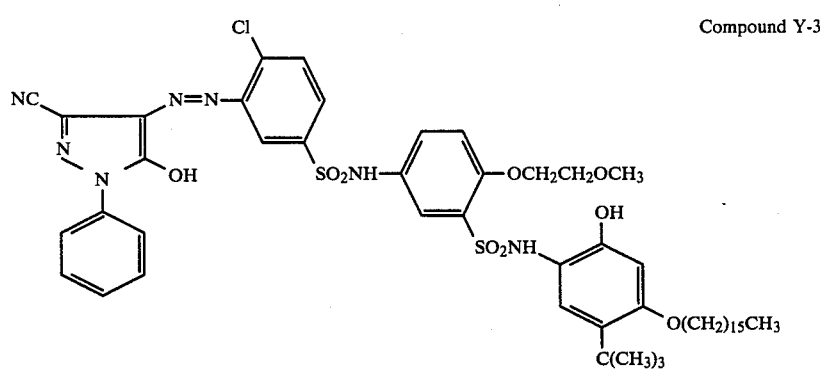
Compound Y-4
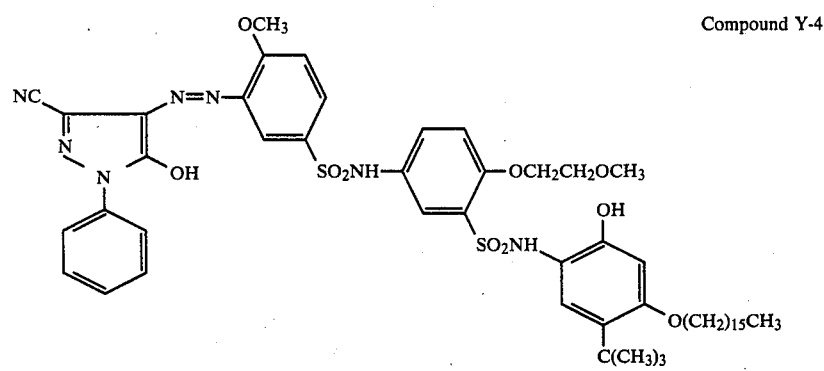
Compound Y-5
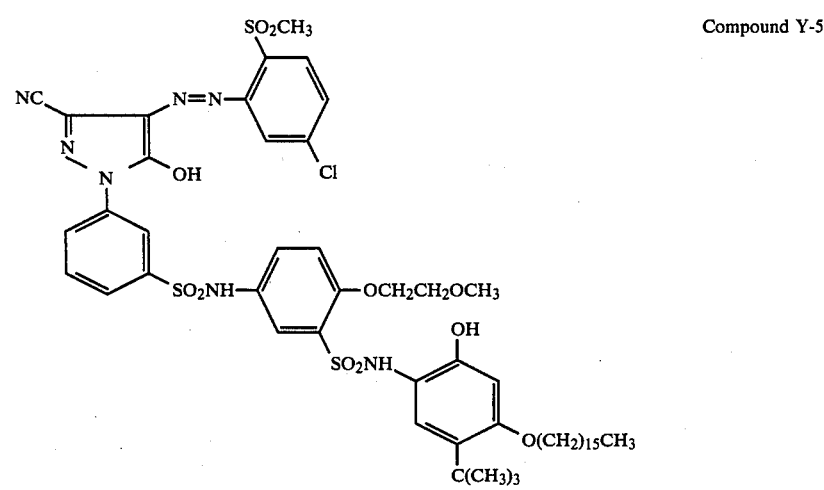

-continued
Compound Y-6
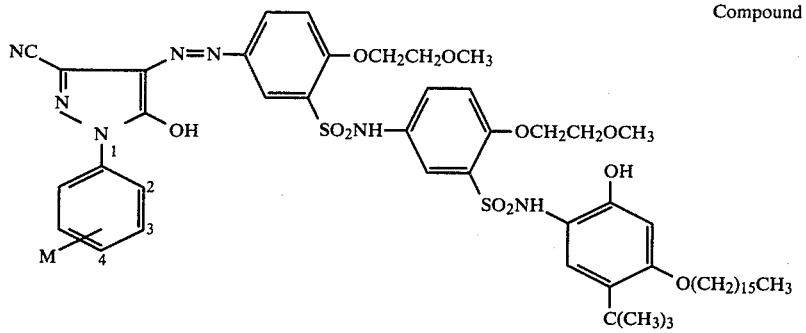
wherein M=2—OCH₃
Compound Y-7
 as in Compound Y-6, wherein M=2—Cl
Compound Y-8
as in Compound Y-6, wherein M=2—CH₃
Compound Y-9
 as in Compound Y-6, wherein M=3—CH₃
Compound Y-10
 as in Compound Y-6, wherein M=4—CH₃
Compound Y-11
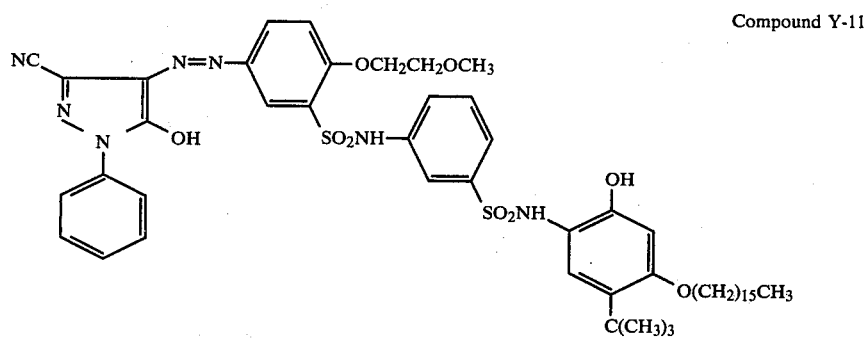
Compound Y-12
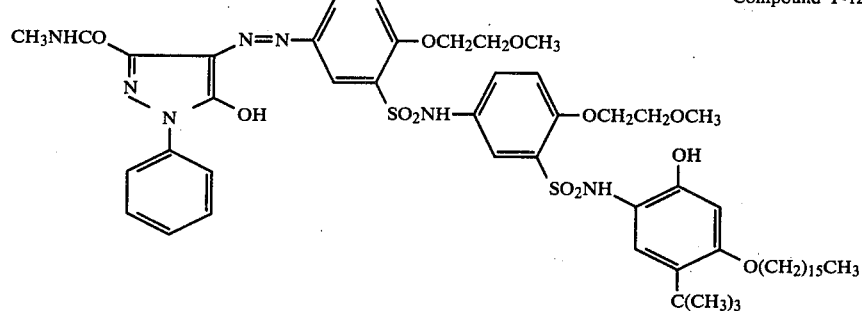
Compound Y-13
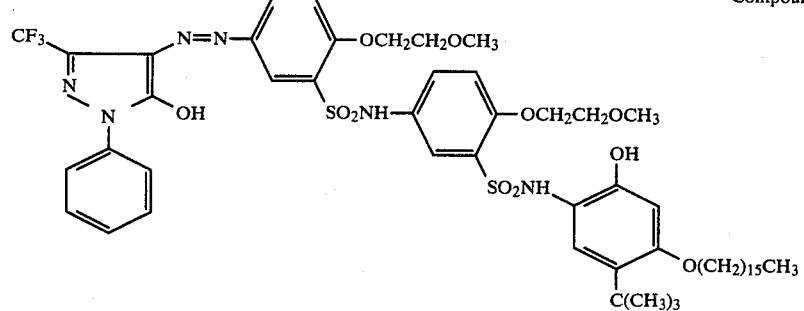

-continued
Compound Y-14
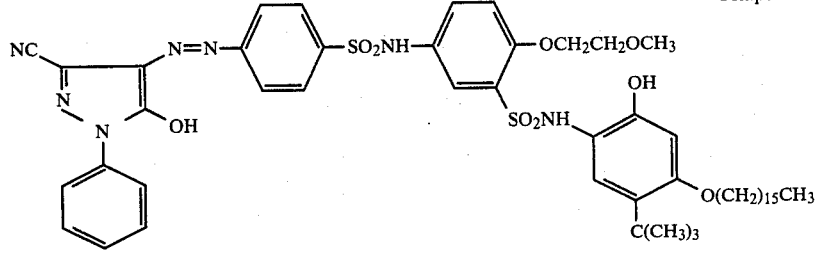
Compound Y-15
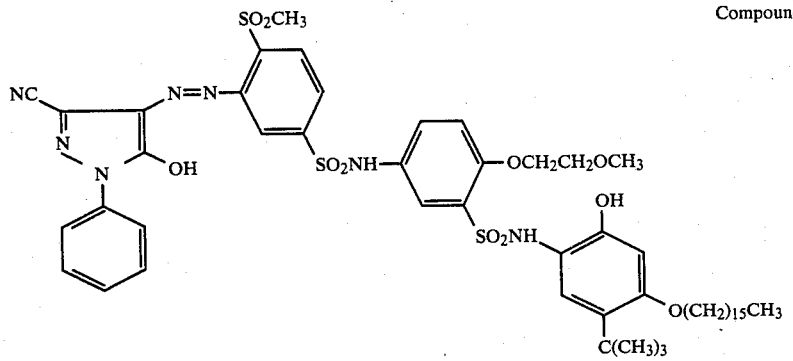
Compound Y-16
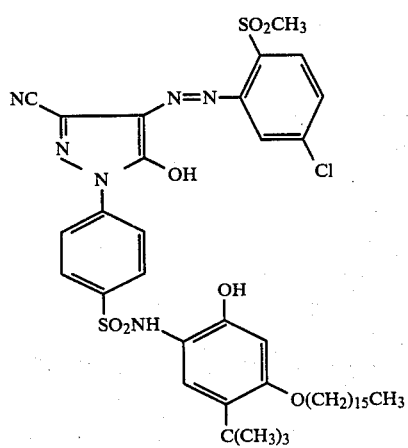
Compound Y-17
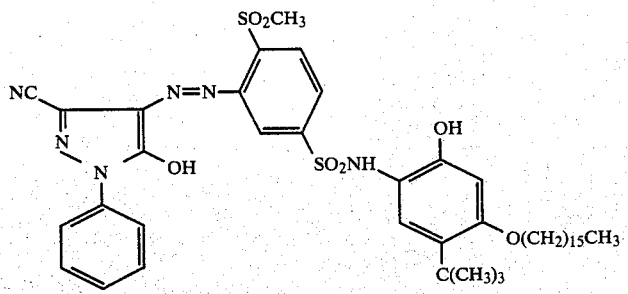
Compound Y-18
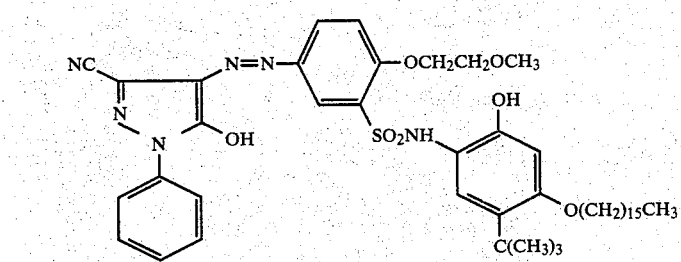

-continued
Compound Y-19
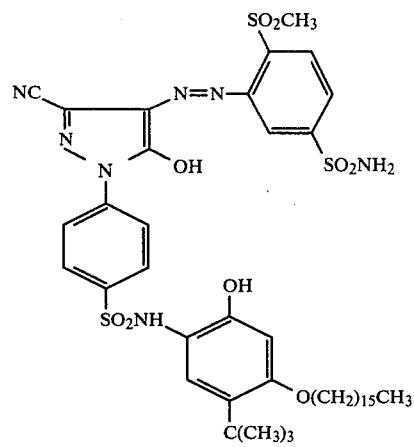
Compound Y-20
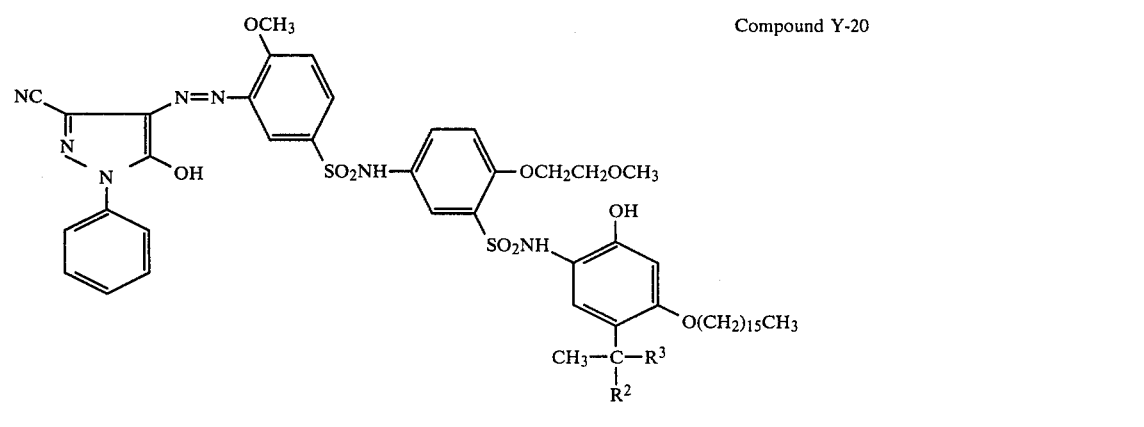
wherein $R^2=CH_3$, $R^3=C_6H_5$
Compound Y-21
 as in Compound Y-20, wherein $R^2=CH_3$, $R^3=C_2H_5$
Compound Y-22
as in Compound Y-20, wherein $R^2=CH_3$, $R^3=CH_2-C(CH_3)_3$
Compound Y-23
 as in Compound Y-20, wherein $R^2=C_2H_5$, $R^3=C_4H_9-n$
Compound Y-24
 as in Compound Y-20, wherein $R^2=CH_3$, $R^3=H$
Compound Y-25
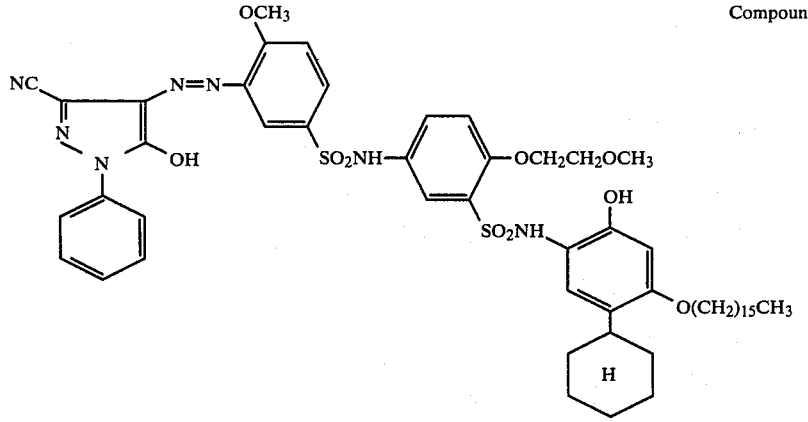

-continued
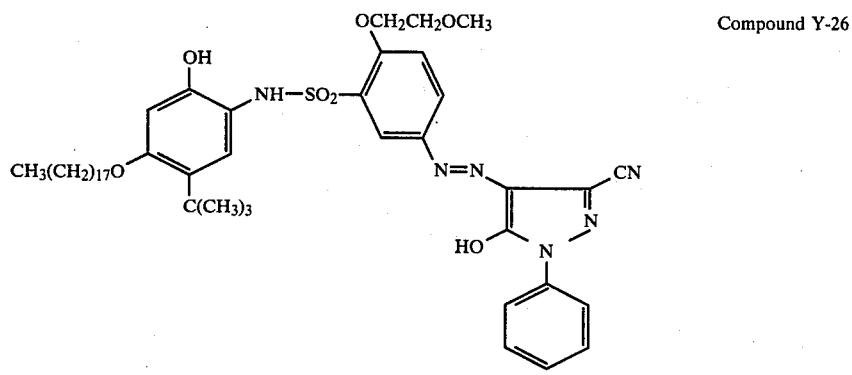
Compound Y-26
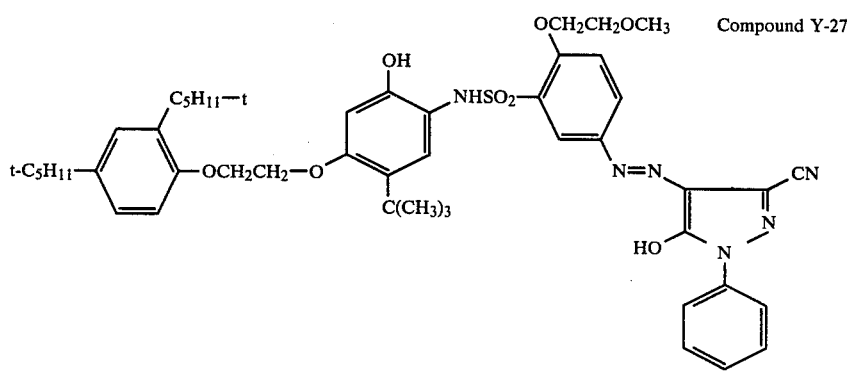
Compound Y-27
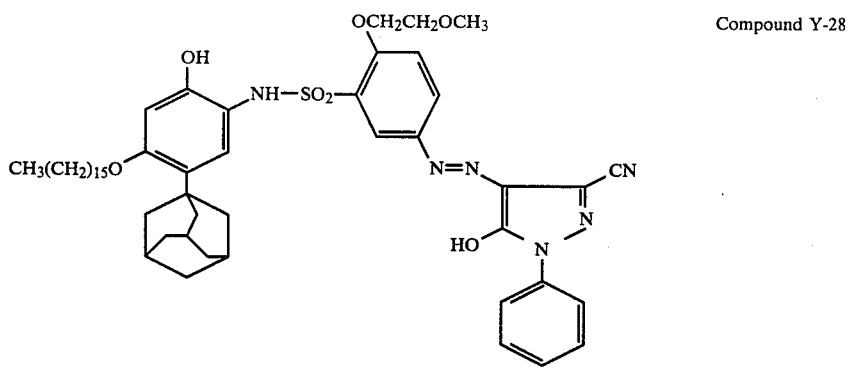
Compound Y-28
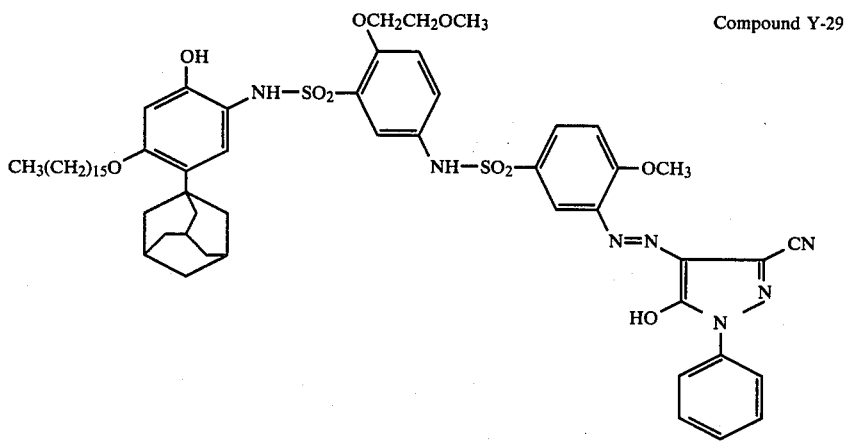
Compound Y-29

Compound Y-30
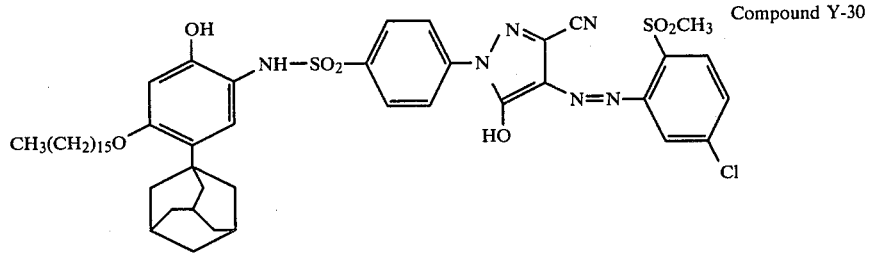
Compound Y-31
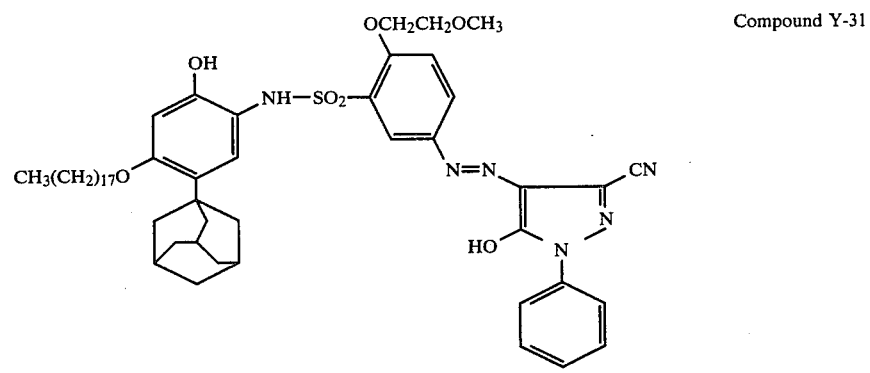
Compound Y-32
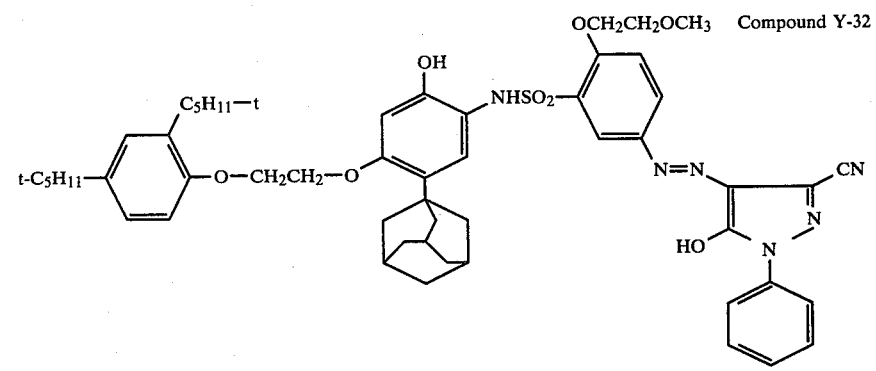
Compound Y-33
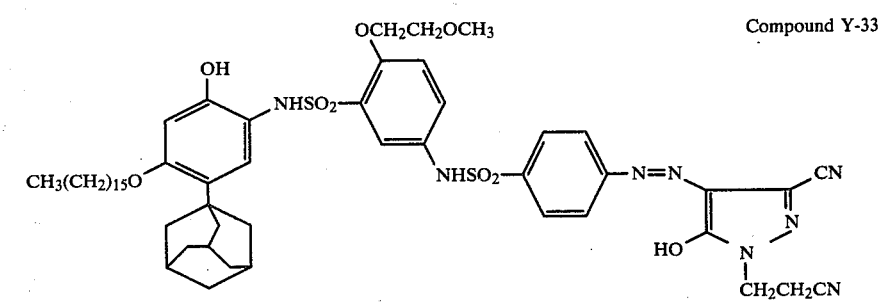
Representative examples of yellow DRR compounds which are not included in formula Y-(I) or Y-(II), but included in formula (I) are as follows:
Compound 1
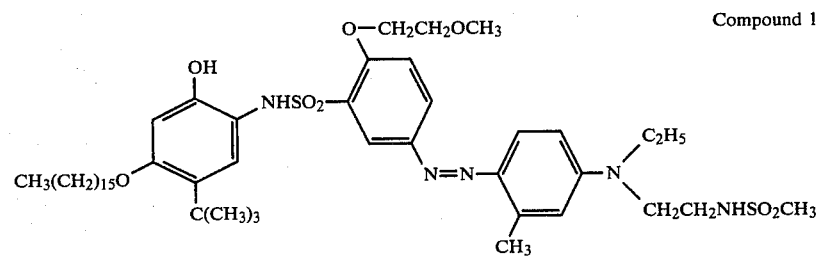

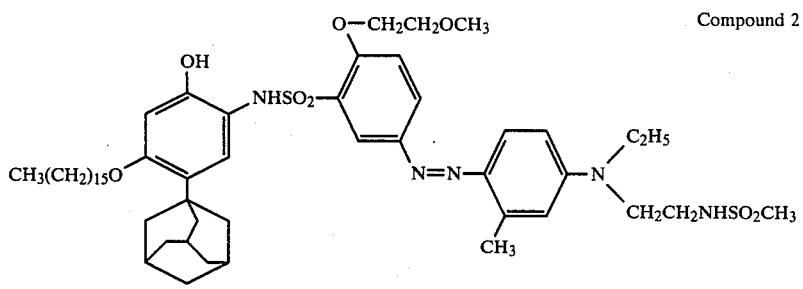

Compound 2

The compounds of this invention having a group represented by formulae Y-(I) or Y-(II) can be synthesized by the condensation of sulfonyl halide of azo dye Y-(V) or Y-(VI) and o-aminophenol derivatives Y-(VII) containing various organic ballast groups.

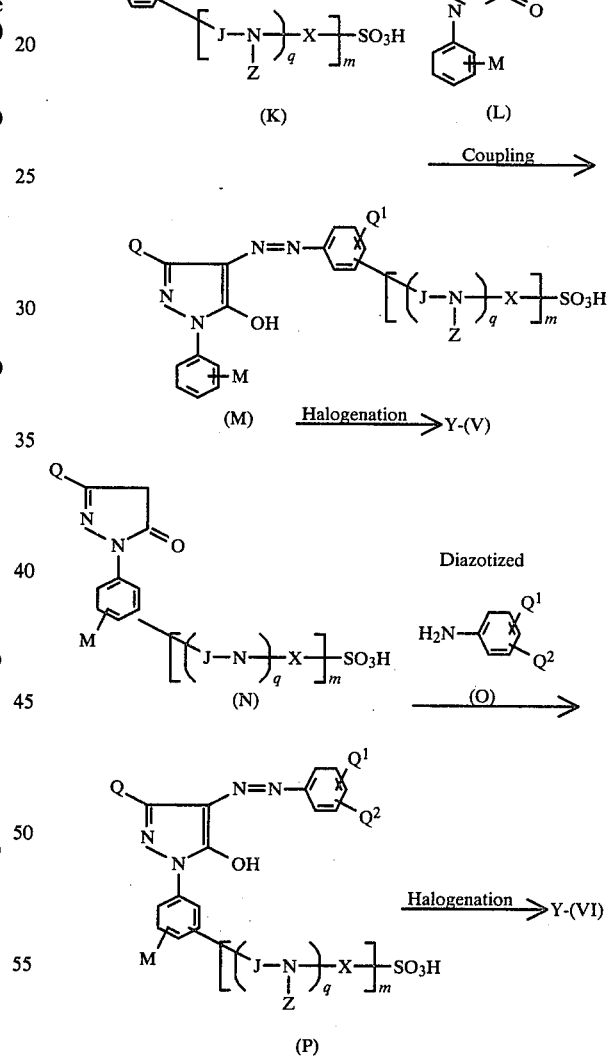

wherein Hal is a halogen atom, where $m=0$, k is 1 or 0 and where $m=1$, k is 0, and the other symbols have the same meanings as in formula Y-(I) or Y-(II) and formula (I).

This condensation reaction can be carried out by the method as described in the synthesis of Compound C-(I).

The compounds represented by formulae Y-(V) and Y-(VI) can be synthesized as follows:

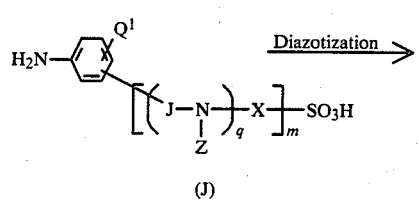

wherein the symbols have the same meanings as in formula Y-(I) or Y-(II).

The diazotization of Compound (J) can be carried out by the methods as described, for example, in Yutaka Hosoda, *Shin Senryo Kagaku*, pp. 114-120, Gihodo, Tokyo (1963) and Hiroshi Horiguchi, *Sosetsu Gosei Senryo*, pp. 114-124, Sankyo Shuppan, Tokyo (1970). Preferred among these methods is so-called "Reversed Method".

According to this method, 1 mol of the diazo component (J), about 1 mol of sodium nitrite and about 1 mole of sodium hydroxide (or a hydroxide of an alkali or alkaline earth metal) are dissolved in water and the resulting mixture is added to a cooled mineral acid water (for example, diluted hydrochloric acid and diluted sulfuric acid). While sodium nitrite or sodium hydroxide is preferably added in the amount as described above, it may be added in an excess amount. The thus obtained diazonium salt solution is mixed with a solution of about 1 mol of Compound (L) in an organic solvent or water to effect the coupling reaction.

Preferred organic solvents for use in dissolving the coupler are those mutually soluble with water, e.g., alcohols such as methanol, ethanol, 2-propanol, methoxyethanol and ethoxyethanol, carbonamides such as N,N-dimethylacetamide and N,N-dimethylformamide and carboxylic acids such as acetic acid and propionic acid. These organic solvents can be used in combination with each other. Furthermore, Compound (L) can be used as the alkali aqueous solution thereof.

The coupling reaction is preferably carried out in the presence of a basic substance. Preferred basic substances include sodium acetate, potassium acetate, sodium hydroxide, potassium hydroxide, sodium carbonate, potassium carbonate and sodium hydrogencarbonate.

Compound (P) can also be synthesized according to the method as described above. However, the diazotization is required to be carried out under the conditions corresponding to the properties of the diazo component (O). The synthesis of Compound (P) can be carried out by reference to the above-described literatures of Yutaka Hosoda and Hiroshi Horiguchi.

While the details of the coupling reaction will be explained in the examples as described later, Hiroshi Horiguchi, *Sosetsu Gosei Senryo*, pp. 124–129, Sankyo Shuppan, Tokyo (1970), H. E. Fierz-David & L. Blangy, *Fundamental Process of Dye Chemistry*, pp. 239–297, Interscience Publishers Inc., New York (1949) and K. Venkataraman, *The Chemistry of Synthetic Dyes*, Chapter 11, Academic Press Inc., New York can be listed as references.

To obtain the compound represented by formula Y-(V) or Y-(VI), the sulfonic acid group of the compound represented by formula (M) or (P) is converted in a halogenosulfonyl group. This synthesizing method will hereinafter be described by reference to the case wherein Hal=Cl since it is preferred.

Chlorinating agents for use in the conversion of the sulfonic acid group of formula (M) or (P) in the chlorosulfonyl group include phosphorus oxychloride, phosphorus pentachloride, thionyl chloride and chlorosulfonic acid. This reaction proceeds smoothly when carboxylic acid amides such as N,N-dimethylacetamide, N,N-dimethylformamide or N-methylpyrrolidone coexist.

The amount of the chlorinating agent required is stoichiometrically determined. In many cases, however, it is desirable to use the chlorinating agent in an excessive amount (e.g., from 1.5 to 50 times the theoretical amount, and preferably from 1.5 to 10 times). In many cases, this reaction proceeds sufficiently at room temperature (about 25° C.). Where the reaction is vigorous, it is possible to cool the reaction mass to as low as about 0° C. On the other hand, where the reaction is slow, it may be heated to a range of from 25° C. to 150° C. (preferably from 25° C. to 100° C.).

Where Hal is another halogen, the compound can be synthesized by the method as described in E. Müller, *Houben-Weyls Methoden der Organishen Chemie*, Vol. IX, pp. 557–598 (1955).

With regard to the synthesis of Compound Y-(V) and Compound Y-(VI), Japanese Patent Application (OPI) Nos. 7727/77 and 111344/79 describe techniques therefor.

PREPARATION EXAMPLE 112

Synthesis of 3-Cyano-4-[4-(2-methoxyethoxy)-5-sulfophenylazo]-1-phenyl-5-pyrazolone To a solution prepared by dissolving 8.0 g of sodium hydroxide in 200 ml of water were added 49.4 g of 5-amino-2-(2-methoxyethoxy)benzenesulfonic acid and 50 ml of an aqueous solution of 13.8 g of sodium nitrite. Separately, a mixture of 60 ml of concentrated hydrochloric acid and 400 ml of water was prepared, to which was dropwise added at 5° C. or less the above-prepared solution. The resulting mixture mixture was then stirred at 5° C. or less for 30 minutes to complete the reaction.

Separately, 16.0 g of sodium hydroxide, 200 ml of water, 33.0 g of sodium acetate and 200 ml of methanol were mixed to prepare a solution and 37.0 g of 3-cyano-1-phenyl-5-pyrazolone was added thereto. To the resulting solution the above-prepared diazo solution was dropwise added at 10° C. or less. After the dropwise addition was completed, the reaction mixture was stirred at 10° C. or less for 30 minutes and then at room temperature for 1 hour. Precipitated crystals were collected by filtration, washed with 200 ml of acetone and dried by air. Yield: 52.0 g; m.p.: 263°–265° C.

PREPARATION EXAMPLES 113 TO 115

In the same manner as in Preparation Example 112, the compounds as illustrated in Table Y-1 were synthesized.

TABLE Y-1

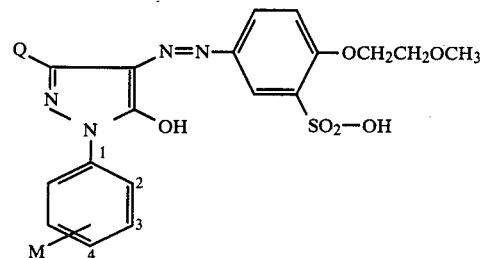

| Preparation Example | Q | M | m.p. (°C.) |
|---|---|---|---|
| 113 | —CN | 2-OCH$_3$ | 207–215 |
| 114 | —CN | 3-CH$_3$ | 205–207 |
| 115 | —CN | 4-CH$_3$ | 258–265 |

PREPARATION EXAMPLE 116

Synthesis of 3-Cyano-4-[4-(2-methoxyethoxy)-5-chloro-sulfonyl-phenylazo]-1-phenyl-5-pyrazolone To a mixture of 51.0 g of the 3-cyano-4-[4-(2-methoxyethoxy)-5-sulfophenylazo]-1-phenyl-5-pyrazolone as obtained in Preparation Example 112, 250 ml of acetone and 50 ml of phosphorus oxychloride was dropwise added 50 ml of N,N-dimethylacetamide at 50° C. or less.

After the addition, the reaction mixture was stirred for about 1 hour and gradually poured in 1.0 l of ice water. Precipitated crystals were collected by filtration, washed with 100 ml of acetonitrile and dried by air. Yield: 46.7 g; m.p.: 181°–183° C.

PREPARATION EXAMPLES 117 TO 120

In an analogous manner as in Preparation Example 116, the compounds as illustrated in Table Y-2 were synthesized.

TABLE Y-2

| Preparation Example | Q | M | m.p. (°C.) |
|---|---|---|---|
| 117 | —CN | 2-OCH$_3$ | 190–194 |
| 118 | —CN | 2-CH$_3$ | 145–149 |
| 119 | —CN | 3-CH$_3$ | 177–182 |
| 120 | —CN | 4-CH$_3$ | 196–197 |

PREPARATION EXAMPLE 121

Synthesis of Compound Y-2

To a solution prepared by dissolving 6.3 g of 2-[5-amino-2(2-methoxyethoxy)benzenesulfonylamino]-4-tert-butyl-5-hexadecyloxyphenol in 30 ml of N,N-dimethylacetamide were added 4.6 g of 3-cyano-4[4-(2-methoxyethoxy)-5-chlorosulfonylphenylazo]-1-phenyl-5-pyrazolone obtained in Preparation Example 116 and furthermore 5 ml of pyridine. After stirring at room temperature for 1 hour, the reaction solution was poured in diluted hydrochloric acid. Precipitated crystals were collected by filtration and recrystallized from N,N-dimethylacetamidemethanol to obtain 7.5 g of Compound Y-2. m.p.: 189°–191° C.

PREPARATION EXAMPLES 122 to 125

Synthesis of Compounds Y-7 to Y-10

In an analogous manner as in Preparation Example 121, Compounds Y-7 to Y-10 were produced from the sulfonyl chlorides as obtained in Preparation Examples 117 to 120, respectively.

PREPARATION EXAMPLE 126

Synthesis of Compound Y-1

To a solution prepared by dissolving 6.3 g of 2-[5-amino-2-(2-methoxyethoxy)benzenesulfonylamino]-4-tert-butyl-5-hexadecyloxyphenol in 30 ml of N,N-dimethylacetamide were added 5.0 g of 3-cyano-4-(5-chloro-2-methylsulfonylphenylazo)-1-(4-chlorosulfonylphenyl)-5-pyrazolone and furthermore 5 ml of pyridine. After stirring at room temperature for 1 hours, the reaction solution was poured in diluted hydrochloric acid. Precipitated crystals were collected by filtration and recrystallized from acetonitrile to obtain 8.4 g of Compound Y-1. m.p.: 144°–149° C.

PREPARATION EXAMPLE 127

Synthesis of Compound Y-3

In an analogous manner as in Preparation Example 126, Compound Y-3 was produced from 2-[5-amino-2-(2-methoxyethoxy)benzenesulfonylamino]-4-tert-butyl-5-hexadecycloxyphenol as obtained in Preparation Example 7 and 3-cyano-4-(2-chloro-5-chlorosulfonylphenylazo)-1-phenyl-5-pyrazolone. m.p.: 115°–120° C.

PREPARATION EXAMPLE 128

Synthesis of Compound Y-18

To 20 ml of N,N-dimethylacetamide were added 4.4 g of 2-amino-4-tert-butyl-5-hexadecyloxyphenol hydrochloric acid salt as obtained in Preparation Example 5 and 4.6 g of 3-cyano-4-[4-(2-methoxyethoxy)-5-chlorosulfonylphenylazo]-1-phenyl-5-pyrazolone obtained in Preparation Example 116. To the resulting mixture was dropwise added 4.7 ml of pyridine with stirring. After the addition was completed, the reaction mixture was further stirred at room temperature for 2 hours. After the stirring, 30 ml of methanol and 10 ml of water were added to the reaction mixture. On adding about 20 ml of ethanol to the above precipitated oily product, crystals precipitated, which were then collected by filtration. Yield: 4.8 g.

PREPARATION EXAMPLE 129

Synthesis of Compound Y-4

To a solution prepared by dissolving 6.3 g of the compound as obtained in Preparation Example 7 and 4.2 g of 4-(5-chlorosulfonyl-2-methoxyphenylazo)-3-cyano-1-phenyl-5-pyrazolone in 20 ml of N,N-dimethylacetamide was added 4.2 ml of pyridine. The resulting mixture was stirred at 25° C. for 1 hour and thereafter 50 ml of methanol and 50 ml of water were added thereto. Oily products precipitated. An addition of 50 ml of ethanol to the precipitated oily products resulted in the crystallization thereof, and the crystals were collected by filtration. Yield: 8.7 g.

PREPARATION EXAMPLE 130

Synthesis of Compound Y-14

To a solution prepared by dissolving 158 g of the compound as obtained in Preparation Example 7 in 700 ml of N,N-dimethylacetamide were added 100 ml of pyridine and then 96 g of 4-(4-chlorosulfonyl-phenylazo)-3-cyano-1-phenyl-5-pyrazolone. The resulting mixture was stirred at 25° C. for 1 hour. On adding to the reaction mixture 600 ml of methanol and 1.2 l of water, oily products decomposed. Thus, the oily products were separated and washed with water. They were then dissolved in 700 ml of acetonitrile. On addition of 1.2 l of methanol, crystals precipitated and collected by filtration. They were recrystallized from 600 ml of ethyl acetate and 1.5 l of methanol to obtain Compound Y-14. Yield: 210 g.

PREPARATION EXAMPLE 131

Synthesis of 2-Acetylamino-4-(1-adamantyl)-5-hexadecyloxyphenol

A mixture of 29 g of 2-acetylamino-5-hexadecyloxyphenol, 150 ml of ethyl acetate, 80 ml of concentrated sulfuric acid and 10 g of 1-adamanthanol was refluxed with stirring at 50° 1 C. for 2 hours. After the reaction mixture was poured into 1 l of water, precipitates formed were collected by filtration and washed with water. The precipitates were recrystallized from 600 ml of ethanol. Yield: 24 g; m.p.: 145.5–147.5° C.

PREPARATION SAMPLE 132

Synthesis of 2-Amino-4-(1-adamantyl)-5-hexadecyloxyphenol Hydrochloric Acid Salt A mixture of 23.7 g of the compound as prepared in Preparation Example 131, 250 ml of ethanol and 96 ml of 35% hydrochloric acid was refluxed with stirring for 5 hours. Thereafter, the reaction solution was cooled. Crystals formed were collected by filtration to obtain 25.5 g of the object. m.p.: 109–115° C.

PREPARATION EXAMPLE 133

Synthesis of Compound $M_1$-26

In 56 ml of N,N-dimethylacetamide was dissolved 10 g of the compound as prepared in Preparation Example 132 and 12 g of 4-[3-chlorosulfonyl-4-(2-methoxyethoxy)phenylazo]-2-(N,N-diethylsulfamoyl)-5-methylsulfonylamino-1-naphthol and then added 6 ml of pyridine. The resulting mixture was stirred at 25° C. for 1 hour, and then poured into a dilute hydrochloric acid. Precipitates formed were collected by filtration and refined with silica gel column chromatography using a mixed solvent of benzene and ethyl acetate (3:2 in volume). Yield: 3.3 g.

With respect to the conventional compounds of this type, the o-sulfonamidophenol derivatives of this invention have the following advantages:

(i) The amount of the compound according to this invention used in a photographic material can be reduced because of its high dye-releasing efficiency.

(ii) Therefore, the thickness of the layer containing the present compound can be reduced. This enables shortening the time required for forming an image.

(iii) Corresponding to the reduced amount of the compound according to this invention used, the amounts of an alkali and a developing agent in the processing solution can also be reduced.

(iv) Corresponding to the reduced amounts of the above-described compounds used, the amount of a color mixture-preventing agent (scavenger of oxidized developing agent) to be used in an intermediate layer can be reduced. This leads to the reduction in the thickness of the intermediate layer and therefore contributes further to the shortening of the time required for forming an image.

(v) Corresponding to the reduced amounts, the amount of a dispersion solvent used can also be reduced.

(vi) Corresponding to the reduced amounts, the amount of a silver halide emulsion used can be reduced. This leads to the reduction in the thickness of the emulsion layer and furthermore contributes to the shortening of the time required for forming an image.

(vii) The compound according to this invention provides a sufficiently high transfer density (Dmax) and a sufficiently low transfer density (Dmin).

(viii) The gradation in the foot portion is high, which is advantageous for the color reproduction.

In addition, the arrangement of the substituents in the compounds according to this invention that the groups $R^1R^2R^3C-$ and $R^4-O-$ are respectively at the 4-position and the 5-position relative to the substituent G is of importance. With respect to those compounds in which the groups $R^1R^2R^3C-$ and $R^4-O-$ are respectively at the 5-position and the 4-position, the present compound has the following advantages:

(ix) The present compound can be used in combination with those developing agents which have lower half wave potentials (i.e., high developing rates). This enables shortening the time required for forming an image.

(x) The present compound is slow in the precipitation as crystals from the solution thereof. Therefore, the emulsion containing the present compound is excellent in stability.

The compound of this invention is combined with a light-sensitive silver halide emulsion to provide a light-sensitive material. When the light-sensitive material is, after imagewise exposure, processed with an alkaline processing solution, at the areas where the silver development takes place, the compound of this invention is oxidized and hydrolyzed, releasing the dye. By application of bleaching and fixing processing steps to the light-sensitive material from which the above released dye has been removed by transferring or water-washing, a color image distribution can be obtained.

When there is used an ordinary emulsion with which development is achieved corresponding to the exposure amount, the transferred image provides a negative image whereas the remaining image provides a positive image.

When a direct reversion emulsion, a DIR reversion emulsion as described in U.S. Pat. Nos. 3,227,551, 3,227,554, 3,364,022, etc., or a reversion emulsion using dissolution physical development as described in British Pat. No. 904,364 is used, the transferred image provides a positive image whereas the remaining image provides a negative image. As necessary, any one of the above emulsions, and any type of combination of a negative image and a positive image can be utilized.

In order to make easy the energy transfer between the DRR compound of this invention which is of relatively low mobility and silver halide particles, the development processing of the light-sensitive material is desirably carried out in the presence of an auxiliary developing agent.

Auxiliary developing agents which can be used for the above purpose are, e.g., as follows:

Black and White Developing Agents

Pyrazolidinones, e.g.,
   1-Phenyl-3-pyrazolidinone
   1-Phenyl-4,4-dimethyl-3-pyrazolidinone
   1-Phenyl-4-methyl-3-pyrazolidinone
   1-Phenyl-4-methyl-4-hydroxymethyl-3-pyrazolidinone
   1-(p-Tolyl)-4-methyl-4-hydroxymethyl-3-pyrazolidinone;
Aminophenols, e.g.,,
   p-Aminophenol
   N-Methyl-p-aminophenol
   N,N-Diethylaminophenol;
Hydroquinones, e.g.,
   p-Tolylhydroquinone

Color Developing Agents

Phenylenediamines, e.g.,
   N,N-Diethyl-p-phenyleneamine
   6-Hydroxy-1,2,3,4-tetrahydroquinoline In general, the black and white developing agents have the advantageous capability of reducing the formation of stains in the image-receiving layer compared to the color developing agents, e.g., phenylenediamines.

Of the black and white developing agents, pyrazolidinones are particularly suitable for use in combination with the DRR compounds of this invention. In particular, it is advantageous to use in combination with 1-aryl-3-pyrazolidinone based developing agents, particularly those represented by the following formula:

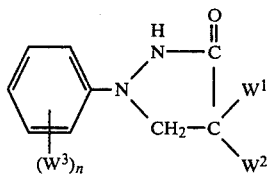

wherein $W^1$ and $W^2$ may be the same or different and each represents hydrogen, an alkyl group (appropriately containing from 1 to about 37 carbon atoms, and including straight, branched and cyclic alkyl groups), which may be substituted, or an aryl group (preferably containing from 6 to 20 carbon atoms, and including phenyl based and naphthyl based aryl groups), which may be substituted.

$W^1$ and $W^2$ may be bound together to form a 4- to 8-membered (preferably 6-membered) carbon ring (preferably a saturated ring).

Suitable examples of substituents for the substituted alkyl group or substituted aryl group are a lower alkyl group containing from 1 to about 6 carbon atoms, a hydroxy group, an alkoxy group containing from 1 to about 20 carbon atoms, preferably from 1 to about 6 carbon atoms, an amino group (an unsubstituted amino group, a mono- or dialkyl substituted amino group, an arylamino group and an amino group substituted by an alkyl group and an aryl group; the number of carbon atoms of such a substituted amino group is suitably from 1 to about 36), a sulfo group, a halogen atom (chlorine, bromine, iodine), and an alkyl or aryl ester group (suitably containing from 1 to about 20 carbon atoms).

Preferred examples of $W^1$ and $W^2$ are a hydrogen atom, an alkyl group and a hydroxyalkyl group (e.g., hydroxymethyl and hydroxyethyl).

$W^3$ represents a hydrogen atom or a substituent with which Hammett's $\sigma$ (sigma) is negative.

n represents an integer of 1 to 5.

Representative examples of substituents in $W^3$ are an alkyl grop (e.g., methyl, ethyl), an alkoxy group (e.g., methoxy, ethoxy), a hydroxy group, an amino group and an aryl group (e.g., phenyl). Where n is 2, a methyl group is an example of the substituents in $W^3$.

Among these compounds, those compounds having the half wave potential of polarography in the range of from about −80 mV to about −200 mV (vs. SCE, at pH 11.0), and preferably about −100 mV to about −150 mV, are particularly advantageous for the following reasons:

Since (1) they rapidly develo silver halide particles and (2) the oxidized products fully efficiently undergo the cross oxidation reaction with the o-sulfonamido phenol derivative of this invention, they enable shortening the time required for the formation of images.

In the utilization of compounds of this invention in the diffusion transfer process, the use of the compound in combination with hydroquinones (e.g., methylhydroquinone, tert-butylhydroquinone, etc.) as well as the developing agents of the above pyrazolidinones is especially advantageous in controlling the gradation in the foot area.

The DRR compound of this invention is generally dispersed in a carrier of hydrophilic colloid by the following method:

The DRR compound is dissolved in an organic solvent and the solution so obtained is added to a solution of hydrophilic colloid and dispersed therein as fine particles. Where the organic solvent used is such a volatile compound as ethyl acetate, tetrahydrofuran and methyl ethyl ketone, it can be removed at the drying step of the photographic layer or by the method as described in U.S. Pat. Nos. 2,322,027, 2,801,171. On the other hand, where the organic solvent is such an easily water-soluble compound as dimethylformamide and 2-methoxyethanol, it can be removed by water-washing according to the method as described in U.S. Pat. Nos. 2,949,360, 3,396,027, etc.

However, in order to stabilize the dispersion of the DRR compound and to accelerate the dye image formation, it is advantageous to incorporate the DRR compound in a solvent which is substantially insoluble in water and has a boiling point of 200° C. or more at atmospheric pressure. Examples of such solvents are dibutyl phthalate, tricresyl phosphate, trihexyl phosphate, tricyclohexyl phosphate and N,N-diethyllauramide. To accelerate the dissolution step of the DRR compound, it is desirable to use the volatile or water-soluble solvent as described above as an auxiliary solvent.

Furthermore, in place of the high boiling point solvent or in combination therewith, an oleophilic polymer can be used. Such oleophilic polymers include a polyester resin obtained by the polycondensation of a polyhydric alcohol and a polybasic acid. In addition, polyvinyl pyrrolidone, polyvinyl acetate, polyvinyl propionate, polyvinyl butyral, polyvinyl chloride, polyacrylate, polymethacrylate, nitrocarboxymethyl cellulose, an N-vinyl pyrrolidone-acrylic acid copolymer, an N-vinyl pyrrolidone-acrylic acid-methyl acrylate copolymer, a vinylphthalimide-acrylic acid copolymer, cellulose acetate hydrogenphthalate, poly-N-methylmethacrylamide, a dimethylaminoethyl methacrylate-acrylic acid copolymer, etc., can be used.

For this dispersion, a colloid mill, a high pressure homogenizer, a supersonic emulsifying apparatus, a high speed rotary mixer, etc., can generally be used. As an auxiliary emulsifying agent, an anion surface active agent is preferably used.

Surface active agents which are useful for use in the dispersion of the present compound include sodium triisopropylnaphthalene sulfonate, sodium dinonylnaphthalene sulfonate, sodium p-dodecylbenzene sulfonate, sodium dioctylsulfosuccinate, sodium cetylsulfate, a formalin condensate (average degree of condensation: about 6.8) wherein the ratio of p-nonylphenol to sodium p-nonylphenoxybutyl sulfonate is about 55:45 as disclosed in Japanese Patent Application (OPI) No. 138726/78, sodium p-tert-octylphenylpolyoxyethylene sulfonate as disclosed in Japanese Patent Application (OPI) No. 117122/77 and anion surface active agents as described in Japanese Patent Publication No. 4293/64 and British Pat. No. 1,138,514.

The use of such an anionic surface active agent in combination with a higher aliphatic acid ester of anhydrohexytol provides excellent emulsifying capability as disclosed in U.S. Pat. No. 3,676,141. Additionally, the dispersion methods as disclosed in Japanese Patent Publication No. 13837/68, U.S. Pat. Nos. 2,992,104, 3,044,873, 3,061,428, 3,832,173, etc., are useful for use in the dispersion of the compound of this invention.

Hydrophilic colloids for use in the dispersion of the present compound include gelatin, colloidal albumin, casein, cellulose derivatives such as carboxymethyl cellulose and hydroxyethyl cellulose, agar, sodium alginate, sugar derivatives such as starch derivatives, and synthetic hydrophilic colloids such as polyvinyl alcohol, poly-N-vinyl pyrrolidone, an acrylic acid copolymer, polyacrylamide or their derivatives or partly hydrolyzed products. As necessary, a mixture of two or more mutually soluble ones of the above colloids is used. While gelatin is the most generally used of the colloids as described above, a part or all of the gelatin may be substituted by a synthetic polymer substance.

In a light-sensitive element for the color diffusion transfer process, the DRR compound is used in combination with a silver halide emulsion.

The silver halide emulsion for use in this invention is a hydrophilic colloidal dispersion of silver chloride, silver bromide, silver chlorobromide, silver iodobromide, silver chloroiodobromide or a mixture thereof. The halogen composition is determined depending upon the purpose for which the light-sensitive material is used and the processing conditions. In particular, a silver bromide emulsion, a silver iodobromide emulsion or a silver chloroiodobromide emulsion wherein the iodide content is 10 mol % or less, and the chloride content is 30 mol % or less, and the remainder is the bromide, is preferred.

The grain size of the silver halide used may be of usual particle size or of fine particle size. It is, however, preferred that the average grain diameter be in the range of from about 0.1 micron to about 2 microns. Furthermore, depending upon the application in which the light-sensitive material is used, it is desirable that the particle diameters be uniform.

The crystal form of the particle used may be of the cubic system or octahedron or of the mixed crystal system.

These silver halide emulsions can be prepared by the known method as described, for example, in P. Glafkides, *Chimie Photographique*, 2nd Ed., Paul Montel, Paris (1957).

The silver halide emulsion as used in this invention can desirably be chemically sensitized by natural sensitizers contained in gelatin, sulfur sensitizers such as sodium thiosulfate and N,N,N'-triethylthiourea, gold sensitizers such as a thiocyanate complex salt or thiosulfuric acid complex salt of monovalent gold, reduction sensitizers such as stannous chloride and hexamethylenetetramine, etc. In this invention, a silver halide emulsion which easily forms a latent image on the surface of particle, an internal latent image type silver halide emulsion as described in U.S. Pat. Nos. 2,592,550, 3,206,313, etc., and furthermore a direct reversal silver halide emulsion using a desensitizing dye and a solarization type silver halide emulsion can be used.

With regard to the solarization type silver halide emulsion, those as described in Mees, *The Theory of the Photographic Process*, pp. 261–297, Macmillan Co., New York (1942) are useful. The method of preparing such an emulsion is described in British Pat. Nos. 443,245, 462,730, U.S. Pat. Nos. 2,005,837, 2,541,472, 3,367,778, 3,501,305, 3,501,306 and 3,501,307.

The internal latent image type silver halide emulsion which is advantageously used in this invention has a light-sensitive center mainly in the interior of the silver halide emulsion particle where a latent image is selectively formed by exposure whereas on the particle surface, the extent to which a latent image is formed is low. Such an internal latent image type silver halide emulsion is characterized by the fact that the amount of silver (corresponding to a surface latent image) in the image obtained by developing with a surface developer after exposure according to T. H. James, *The Theory of Photographic Process*, pp. 171–176, 4th Ed., (1977) is clearly lower than that (corresponding to the total latent image) obtained with an internal developer.

The internal latent image silver halide emulsion can be produced by various methods. Examples of such emulsions are the Burton emulsion which has a high iodine content and is produced by the ammonia process (E. J. Wall, *Photographic Emulsions*, pp. 35–36 and 52–53, American Photographic Publishing Co., (1929) and U.S. Pat. Nos. 2,497,875, 2,563,785), a primitive emulsion in a big particle form which has a low iodine content and is produced by an ammonia process (e.g., as described in West German Patent Application (OLS) No. 2,728,108), an emulsion which is produced by precipitating silver halide particles by the rapid reduction in the concentration of ammonia in a silver halide-ammonia complex salt solution (U.S. Pat. No. 3,511,662), a conversion emulsion obtained by a catastrophic precipitation method in which silver halide particles having a high solubility, such as silver chloride, are first produced and then they are converted to a silver salt having a low solubility, such as silver iodide (U.S. Pat. No. 2,592,250), a core shell emulsion which is produced by providing a shell of silver halide on a big particle of a chemically sensitized core emulsion by mixing the big particle and a fine particle followed by aging (U.S. Pat. No. 3,206,313 and British Pat. No. 1,011,062), a core shell emulsion which is produced by providing a shell of silver halide on a core particle by a method wherein a soluble silver salt solution and a soluble halide solution are simultaneously added to a monodisperse core emulsion subjected to chemical sensitization while keeping the silver ion concentration at a constant level (British Pat. No. 1,027,146 and U.S. Pat. No. 3,761,276), a halogen localized emulsion in which the emulsion particle is of the two or more laminated layer construction and the first layer and the second layer are different in the halogen composition (U.S. Pat. No. 3,935,014), and an emulsion containing therein a different kind of metal which is produced by forming silver halide particles in an acidic medium containing trivalent metal ions (U.S. Pat. No. 3,447,927).

Typical nucleating agents for the emulsion of this type include hydrazines as described in U.S. Pat. Nos. 2,588,982, 2,563,785, hydrazide and hydrazone as described in U.S. Pat. No. 3,227,552, and tertiary salt compounds as described in British Pat. No. 1,283,835, Japanese Patent Publication No. 38164/74, U.S. Pat. Nos. 3,734,738, 3,719,494, 3,615,615.

In the DIR reversion emulsion method as described in U.S. Pat. Nos. 3,227,551, 3,227,554, 3,364,022 and the reversion emulsion method by dissolution physical development as described in British Pat. No. 904,364, such fogging agents can be used in combination with the DRR compound of this invention.

The silver halide emulsion as used in this invention may be stabilized by adding such additives as 4-hydroxy-6-methyl-1,3,3a,7-tetrazaindene, 5-nitroimidazole, 1-phenyl-5-mercaptotetrazole, 8-chloromercury quinoline, benzenesulfinic acid, pyrocatechin, 4-methyl-3-sulfoethylthiazolidine-2-thione, 4-phenyl-3-sulfoethylthiazolidine-2-thione. In addition, inorganic compounds, e.g., complex salts of elements in the platinum group, such as cadmium salt, mercury salt and chloro complex salt of palladium are also used for the stabilization of the present light-sensitive material. Furthermore, the silver halide emulsion used may contain a sensitizing compound such as polyethylene oxide.

The silver halide emulsion as used in this invention may have, if desired, color sensitivity which is enlarged by a spectral sensitizing dye. Useful spectral sensitizers include cyanines, merocyanines, holopolar cyanines, styryls, hemicyanines, oxanols, hemioxanols and the like.

Representative examples of such spectral sensitizers are described in P. Glafkides, *Chimie Photographique*, 2nd Ed., Chapters 35–41, Paul Montel, Paris (1957), and F. M. Hamer, *The cyanine and Related Compounds*, Interscience. In particular, cyanines in which the nitrogen atom of the basic heterocyclic ring is substituted by an aliphatic group (e.g., alky) containing a hydroxy group, a carboxyl group and a sulfo group, as described in U.S. Pat. Nos. 2,503,776, 3,459,553 and 3,177,210 are useful in the practice of this invention.

The light-sensitive element of the light-sensitive material for the color diffusion transfer process according to this invention is coated on a plane-like substance which is subject to no marked change in dimension during the processing, for example, a cellulose acetate film, a polystyrene film, a polyethylene terephthalate film, a polycarbonate film or a laminated material thereof, a thin glass film or the like which are usually used in the production of a photographic light-sensitive material.

Where the adhesion force between the support and the photographic emulsion layer is insufficient, a layer which exhibits adhesive properties to both the layers is provided between them as an undercoating (subbing) layer. Additionally, in order to further increase the adhesive properties, the surface of the support may be subjected to preliminary processings such as corona discharge, irradiation of ultraviolet rays, flame processing, etc.

Other substances which can be used as a support include paper and a laminated paper with a water-impermeable polymer such as polyethylene laminated on the surface thereof.

The DRR compound of this invention can be used in a general light-sensitive material and in particular, in a color diffusion transfer light-sensitive material. In this case, for the formation of such a laminated light-sensitive material, the methods as described in Japanese Patent Publication No. 16356/71, Japanese Patent Application No. 106404/74, and U.S. Pat. No. 3,594,164 can be used.

In the color light-sensitive element to which this invention is applicable, the silver halide emulsion and the DRR compound are combined. Corresponding to the desired color reproduction, a suitable combination of the color sensitivity of the silver halide emulsion and the spectral absorption of the dye image is chosen. In the reproduction of natural color by the subtractive color process, a light-sensitive element comprising at least two combinations of an emulsion having a selective light-sensitivity in a certain wavelength region and a compound which provides a dye image having a selective spectral absorption in the same wavelength region as above can be employed. Particularly, a light-sensitive element comprising a combination of a blue-sensitive silver halide emulsion and the yellow DRR compound of formula Y-(I), combinations of a green-sensitive emulsion and the magenta DRR compound of formula $M_1$-(I) or $M_2$-(I), and a combination of a red-sensitive emulsion and the cyan DRR compound of formula C-(I) are useful.

The combinations of the emulsion and the DRR compound may be each coated in a layer form so that the thus-formed layers are superposed on each other or all the combinations may be each formed in a particle form, mixed with each other and coated in a single layer. In a preferred multilayer construction, the red-sensitive emulsion combination unit is provided on the support, the green-sensitive emulsion combination unit is provided on the red-sensitive emulsion combination unit, and the blue-sensitive emulsion combination unit is provided on the green-sensitive emulsion combination unit. In the case of the high sensitivity emulsion containing silver iodide, a yellow filter layer is provided between the blue-sensitive emulsion combination unit and the green-sensitive emulsion combination unit.

The yellow filter can comprise a yellow colloidal silver dispersion, a dispersion of an oil-soluble yellow dye, an acidic dye mordanted by a basic polymer or a basic dye mordanted by an acidic polymer, and the like. It is advantageous that these emulsion combination units are separated from each other by an intermediate layer. The intermediate layer prevents undesirable interaction from occurring between the emulsion combination units having different color sensitivities.

The intermediate layer is composed, for example, of hydrophilic polymers such as gelatin, polyacrylamide and partly hydrolyzed products of polyvinyl acetate; latex polymers having fine pores as described in U.S. Pat. No. 3,625,685, which are produced from hydrophilic polymers and hydrophobic polymers; or polymers such as calcium alginate which gradually increase hydrophilic properties by a processing composition as described in U.S. Pat. No. 3,384,483.

Between the intermediate layer and the layer containing the DRR compound may be provided a layer (e.g., a gelatin layer) to separate them from each other so that the DRR compound is prevented from migrating in the intermediate layer.

In order to prevent the oxidized product of the developing agent from diffusing to another emulsion combination unit having different color sensitivity, the intermediate layer may contain therein those compounds which act to capture such an oxidized product, for example, a color mixture-preventing agent such as 2,5-di(sec-dodecyl)-hydroquinone and 2,5-di(tert-pentadecyl)-hydroquinone.

The DRR compound of this invention is used in such an amount that the molar ratio of silver in the silver halide emulsion to the DRR compound be from about 50 to 0.5, and preferably from about 20 to about 2.

It is essential for the image-receiving element to include a mordanting layer, which can be composed of, e.g., a poly-4-vinyl pyridine latex (particularly in polyvinyl alcohol) as described in U.S. Pat. No. 3,148,061, polyvinyl pyrrolidone as described in U.S. Pat. No. 3,003,872, or a polymer containing a tertiary ammonium salt as described in U.S. Pat. No. 3,239,337. Basic polymers as described in U.S. Pat. Nos. 2,882,156, 3,625,694, 3,709,690, etc., are also useful mordants. Additionally, those mordants as described in U.S. Pat. Nos. 2,484,430, 3,271,147, 3,184,309, 3,271,147, etc., are useful.

The color photographic material of this invention preferably functions to neutralize the alkali brought thereinto from the processing composition. The processing composition contains an alkali to provide a pH of 10 or more, and preferably 11 or more, which is sufficient to accelerate "image-forming step" comprising the development of silver halide emulsion, the diffusion of DRR compound and the like. After the formation of a diffusion transfer image is materially completed, the pH in the film unit is neutralized to 9 or less, and preferably 8 or less, to materially stop the image-formation at this stage whereby the change with time of the image tone is prevented and the discoloration of image and the staining of brown and white areas caused by a high alkali concentration are prevented.

For this purpose, it is advantageous to incorporate in the film unit a neutralizing layer which contains an acidic substance in an amount sufficient to neutralize the alkali in the processing solution to the above range, that is, contains an acidic substance in an area concentration which is equivalent to or more than the alkali in the developed processing solution.

Preferred acidic substances contain an acidic group having a pKa of 9 or less or a precursor producing such as acidic group by hydrolysis. More preferred ones are higher aliphatic acids such as oleic acid as described in U.S. Pat. No. 2,983,606, and a polymer of acrylic acid, methacrylic acid or maleic acid, or its partial ester or anhydride as described in U.S. Pat. No. 3,362,819.

Representative examples of acidic polymer substances are copolymers of vinyl monomers such as ethylene, vinyl acetate, vinyl methyl ether or the like and maleic anhydride and the half-butyl esters thereof, copolymers of butyl acrylate and acrylic acid, cellulose acetatehydrogen phthalate, etc.

The neutralizing layer can contain, in addition to the acidic substances as described above, polymers such as cellulose nitrate and polyvinyl acetate. Moreover, plasticizers as described in U.S. Pat. No. 3,557,237 can be incorporated therein. Furthermore, the neutralizing layer may be hardened by the cross-linking reaction using a polyfunctional aziridine compound and an epoxy compound.

The neutralizing layer is placed in the image-receiving element and/or the light-sensitive element. In particular, it is advantageous to place it between the support of the image-receiving element and the image-receiving layer thereof. As described in West German Patent Application (OLS) No. 2,038,254, the acidic substance may be microencapsulated and incorporated in the film unit.

In the above case, it is desirable that the neutralizing layer and the acidic substance-containing layer are separated from the processing solution layer to be developed by a neutralization rate-controlling layer (timing layer). This neutralization rate-controlling layer acts to retard the neutralization of the processing solution by the neutralizing layer and to sufficiently proceed the desired development and transfer.

The neutralization rate-controlling layer is mainly composed of gelatin, polyvinyl alcohol, polyvinyl propyl ether, polyacrylamide, hydroxypropylmethyl cellulose, isopropyl cellulose, partial polyvinyl butyral, partially hydrolyzed polyvinyl acetate, or a copolymer of β-hydroxyethyl methacrylate and ethyl acrylate. Those polymers obtained by hardening the above polymers by the cross-linking reaction using an aldehyde compound such as formaldehyde or an N-methylol compound are useful.

Examples of such neutralization rate-controlling layers are described in U.S. Pat. Nos. 3,455,686, 4,009,030, 3,785,815, Japanese Patent Application Nos. 77946/75, 90616/75, Japanese Patent Application (OPI) Nos. 92022/73, 64435/74, 22935/74, 77333/76, Japanese Patent Publication Nos. 15756/69, 12676/71, 41214/73, West German Patent Application (OLS) Nos. 1,622,936, 2,162,277, *Research Disclosure*, 15162, No. 151 (1976), etc.

Preferably, the thickness of the neutralization rate-controlling layer is from 2 microns to 20 microns.

The processing composition for use in this invention is a liquid composition which contains processing components required for developing the silver halide emulsion and for forming the diffusion transfer dye or a dye image remaining after the released dye is flowed away. The major component of the solvent is water. In some cases, the solvent may contain a hydrophilic solvent, such as methanol and 2-methoxyethanol.

The processing composition contains an alkali in an amount enough to maintain the pH required for causing the development of the emulsion layer and to neutralize the acids (e.g., halogen hydrogen acid such as bromo hydrogen acid) formed during the various courses including development and the formation of dye image. Examples of such alkalis are alkali or alkaline earth metal salts and amines, such as lithium hydroxide, sodium hydroxide, potassium hydroxide, a dispersion of calcium hydroxide, tetramethylammonium hydroxide, sodium carbonate, sodium tertiary phosphate and diethylamine.

Where the processing composition is used in the diffusion transfer process, it is desirable to incorporate caustic alkali in such a concentration that at room temperature ($\sim$20° C.), the pH is about 12 or more, particularly about 13 or more. More preferably, the processing composition contains high molecular weight hydrophilic polymers, such as polyvinyl alcohol, hydroxyethyl cellulose, and sodium carboxymethyl cellulose. These polymers provide the processing composition with a viscosity of 1 poise or more, and preferably from 500 to 1,000 poises at room temperature, to facilitate uniform development of the processing composition during the processing. Furthermore, where the aqueous solvent migrates in the light-sensitive element and the image-receiving element during the processing, concentrating the processing composition, the polymers form a non-fluidous film to assist the film unit after processing to be combined together. The polymer film, when the formation of the diffusion transfer dye image is substantially completed, can be used to prevent the change of image by controlling the additional migration of the coloring component in the image-receiving layer.

It is advantageous in some cases that the processing composition for use in the diffusion transfer process further contains carbon black to prevent the silver halide emulsion from being fogged by light during the processing, a light-shielding substance such as $TiO_2$ and a pH indicator and a desensitizing agent, as described in U.S. Pat. No. 3,579,333.

The processing composition is preferably placed in a rupturable vessel as described in U.S. Pat. Nos. 2,543,181, 2,643,886, 2,653,732, 2,723,051, 3,056,491, 3,056,492, 3,152,515 and used.

Where the light-sensitive sheet of this invention is in the form of photographic film unit, that is, it is of the construction that the photographic processing can be carried out by passing the imagewise exposed film unit between a pair of rolls which are placed in parallel, it includes, for example, the following elements:

(1) The support,
(2) The light-sensitive element as described above,
(3) The image-receiving element as described above,
(4) The processing element as described above, and
(5) The developer (in the processing element or in the light-sensitive element).

A preferred embodiment in which the above elements are combined together and to which this invention is applicable is described in Belgian Pat. No. 757,959. According to this embodiment, an image-receiving layer, a substantially opaque light reflective layer (e.g., a $TiO_2$ layer and a carbon black layer) and a single or a plurality of light-sensitive layers (light-sensitive element) as described above are successively coated on a transparent support, and furthermore a transparent cover sheet is overlaid thereon in a surface-surface relation. The rupturable container accommodating the alkaline processing composition containing an agent to make opaque (e.g., carbon black) for light-shielding is placed adjacent to the most upper layer (protective layer) of the above light-sensitive layers and the transparent cover sheet.

Such a film unit is exposed through a transparent cover sheet, and when it is removed from a camera, the container is broken by pressing members to cause development of the processing solution (including the agent to make opaque) between the light-sensitive layer and the cover sheet. Thus, the light-sensitive element is shielded from light in the sandwiched form and the development proceeds in a light place.

For the film unit in this embodiment, it is desirable that a neutralization mechanism as described above be incorporated.

In particular, it is preferred that the neutralization layer be provided in the cover sheet (if desired, the timing layer is provided at the side where the processing solution is developed).

Other useful laminated embodiments in which the DRR compound of this invention can be used are described in U.S. Pat. Nos. 3,415,644, 3,415,645, 3,415,646, 3,647,487, 3,635,707, German Patent Application (OLS) No. 2,426,980.

In another desirable embodiment, the image-receiving element of the multilayer construction comprising the support--the neutralization layer--the neutralization rate-controlling layer--the mordanting layer and the material with a single or a plurality of light-sensitive layers (light-sensitive element) successively coated on the support are superposed on each other in a surface-surface relation, and the processing solution is developed between them to effect the processing. In this case, the image-receiving element may be stripped off. Alternatively, as described in U.S. Pat. No. 3,415,645, the support for the image-receiving layer is made transparent and the reflective layer is provided between the image-receiving layer and the light-sensitive layer, so that the image can be seen without stripping.

The photographic light-sensitive material of the present invention can be also used for conventional color photography in addition to color diffusion transfer process.

When the photographic light-sensitive material of the present invention is processed with an alkaline aqueous solution after exposure to light, a DRR compound of the present invention can release a dye by oxidation and hydrolysis. Following removal of the released dye by washing with water, the light-sensitive material is subjected to bleaching and fixing to obtain a color image.

As being apparent from the above, the term "color" implies so-called "black coloration", and the photographic light-sensitive material of the present invention is also conveniently used for X-ray photography.

EXAMPLE 1

On a transparent polyester support the following layers were successively coated to produce a light-sensitive sheet.

(1) A mordanting layer containing 3.0 g/m² of a mordant as shown below and 3.0 g/m² of gelatin.

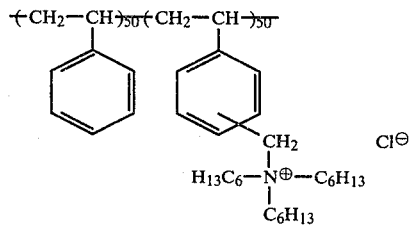

(2) A white reflective layer containing 20 g/m² of titanium dioxide and 2.0 g/m² of gelatin.

(3) A light-shielding layer containing 2.70 g/m² of carbon black and 2.70 g/m² of gelatin.

(4) A layer containing 0.40 g/m² of a cyan DRR compound as shown below, 0.09 g/m² of tricyclohexyl phosphate, 0.01 g/m² of 2,5-di(tert-pentadecyl)hydroquinone and 0.8 g/m² of gelatin.

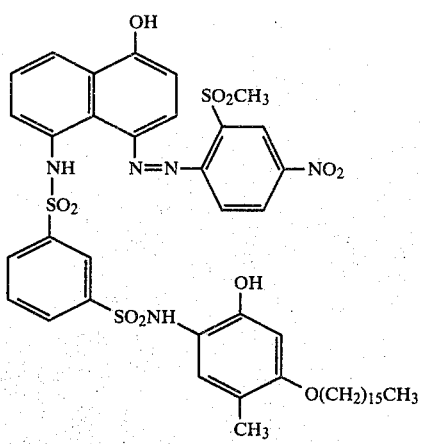

(5) A layer containing 1.03 g/m² (as silver) of a red-sensitive internal latent image type direct reversal silver bromide emulsion, 1.2 g/m² of gelatin, 0.05 mg/m² of a nucleating agent as shown below and 0.13 g/m² of sodium pentadecylhydroquinone sulfonate.

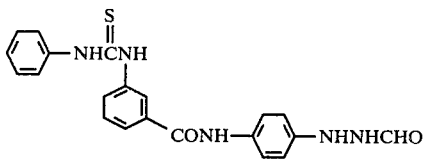

(6) A layer containing 0.71 g/m² of 2,5-(tert-pentadecyl)hydroquinone, 0.24 g/m² of a copolymer of vinyl pyrrolidone and vinyl acetate (molar ratio: 7:3) and 0.6 g/m² of gelatin.

(7) A layer containing 0.4 g/m² of gelatin.

(8) A layer containing 0.32 g/m² of a magenta DRR compound as shown below, 0.08 g/m² of tricyclohexyl phosphate, 0.01 g/m² of 2,5-di(tert-pentadecyl)hydroquinone and 0.6 g/m² of gelatin.

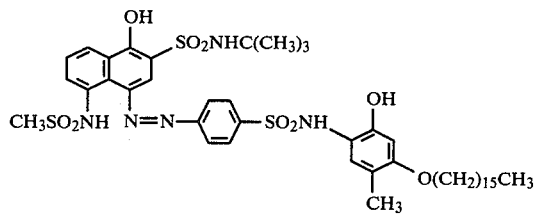

(9) A layer containing 0.82 g/m² (as silver) of a green-sensitive internal latent image type direct reversal silver bromide emulsion, 0.9 g/m² of gelatin, 0.03 mg/m² of the same nucleating agent as used in Layer (5) and 0.08 g/m² of sodium pentadecylhydroquinone sulfonate.

(10) A layer containing 0.71 g/m² of 2,5-di(tert-pentadecyl)hydroquinone, 0.24 g/m² of a copolymer of vinyl pyrrolidone and vinyl acetate (molar ratio: 7:3) and 0.6 g/m² of gelatin.

(11) A layer containing 0.4 g/m² of gelatin.

(12) A layer containing 0.53 g/m² of a yellow DRR compound as shown below, 0.13 g/m² of tricyclohexyl phosphate, 0.01 g/m² of 2,5-di(tert-pentadecyl)hydroquinone and 0.7 g/m² of gelatin.

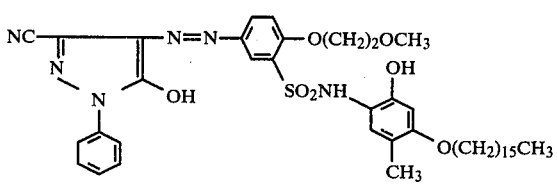

(13) A layer containing 1.09 g/m² (as silver) of a blue-sensitive internal latent image type direct reversal silver bromide emulsion, 1.1 g/m² of gelatin, 0.04 mg/m² of the same nucleating agent as used in Layer (5) and 0.07 g/m² of sodium pentadecylhydroquinone sulfonate.

(14) A layer containing 1.0 g/m² of gelatin.

A processing solution having the composition as illustrated below was charged in an amount of 0.8 g to a rupturable container.

| Composition of Processing Solution | |
|---|---|
| 1-(p-Tolyl)-4-hydroxymethyl-4-methyl-3-pyrazolidinone | 6.9 g |
| tert-Butylhydroquinone | 0.2 g |
| 5-Methylbenzotriazole | 3.5 g |
| Sodium Sulfite (anhydrous) | 0.2 g |
| Carboxymethyl Cellulose Sodium Salt | 58 g |
| Carbon Black | 150 g |
| Potassium Hydroxide (28% aq. soln.) | 200 cc |
| Benzyl Alcohol | 1.5 cc |
| H₂O | 580 cc |

On a transparent polyester support the following layers were successively coated to produce a cover sheet.

(1) A layer containing 22 g/m² of an acrylic acid-butyl acrylate (80:20 by weight) copolymer and 0.44 g/m² of 1,4-bis(2,3-epoxypropoxy)butane.

(2) A layer containing 3.8 g/m² of acetyl cellulose (hydrolysis of 100 g of acetyl cellulose provides 39.4 g of an acetyl group), 0.2 g/m² of a styrene-maleic anhydride (60:40 by weight) copolymer (molecular weight: about 50,000) and 0.115 g/m² of 5-(β-cyanoethylthio)-1-phenyltetrazole.

(3) A layer containing 2.5 g/m² of a latex copolymer of vinylidene chloride, methyl acrylate and acrylic acid (85:12:3 by weight) and 0.05 g/m² of a latex of polymethyl methacrylate (grain diameter: 1 to 3 microns).

The above light-sensitive sheet is designated Sample A. Additionally, Samples B$^c$, C$^c$, D$^c$ and E$^c$ were produced by the same method as above except that the compounds as illustrated in Table 1 were used in place of the cyan DRR compound of Layer (4).

Each of Samples A to E$^c$ was exposed and combined together with the processing solution and cover sheet as obtained above. Thereafter, by extending the processing solution in a thickness of 80 μm at 25° C. by use of the pressing member, a transferred dye image was obtained. The results are shown in Table 1.

As can be seen from the results as illustrated in Table 1, Samples B$^c$, C$^c$, D$^c$ and E$^c$ were high in the maximum reflective density, low in the minimum reflective density and provided good gradation in the foot area in comparison with Sample A. Furthermore, with Samples B$^c$, C$^c$, D$^c$ and E$^c$, the conversion ratio (transferred color image density/developed silver amount) in the vicinity of the maximum reflective density was great, and the utilization ratio (transferred color image density/amount of coated DRR compound) was also great.

TABLE 1

| Sample | DRR Compound | Amount[1] (g/m²) | Processing Temp. (°C.) | Cyan Maximum Reflective Density | Cyan Minimum Reflective Density | Gradation in[2] Foot Area (0.5/Δ log E) | Remarks |
|---|---|---|---|---|---|---|---|
| A | Layer(4) as is | 0.40 | 25 | 0.78 | 0.31 | 0.52 | Comparison |
| B$^c$ | C-3 | 0.51 | " | 1.40 | 0.30 | 0.72 | Invention |
| C$^c$ | C-4 | 0.42 | " | 1.45 | 0.30 | 0.76 | " |
| D$^c$ | C-8 | 0.44 | " | 1.51 | 0.30 | 0.65 | " |

TABLE 1-continued

| Sample | DRR Compound | Amount*[1] (g/m²) | Processing Temp. (°C.) | Cyan Maximum Reflective Density | Cyan Minimum Reflective Density | Gradation in*[2] Foot Area (0.5/Δ log E) | Remarks |
|---|---|---|---|---|---|---|---|
| E[c] | C-11 | 0.51 | " | 1.70 | 0.31 | 0.60 | " |

*[1]Coated in such a manner that the mol number per square meter of the compound was equal.
*[2]When log (exposure amount) corresponding to Dmin + 0.5 is indicated by Δ log E in the characteristic curve obtained by using a direct reversion emulsion, 0.5/Δ log E can be represented as the gradation at the foot area. As (0.5/Δ log E) is higher, the contrast is higher.

EXAMPLE 2

An experiment was conducted in the same manner as in Example 1 except that the developing agent was changed to 1-phenyl-4-hydroxymethyl-4-methyl-3-pyrazolidinone (13.0 g). Samples A, B[c], C[c], D[c] and E[c] were processed. The results at 25° C. are shown in Table 2.

As can be seen from Table 2, in comparison with Sample A, Samples B[c], C[c], D[c] and E[c] provided good characteristic values as in Example 1.

TABLE 2

| Sample | DRR Compound | Amount*[1] (g/m²) | Processing Temp. (°C.) | Cyan Maximum Reflective Density | Cyan Minimum Reflective Density | Gradation in*[2] Foot Area (0.5/Δ log E) | Remarks |
|---|---|---|---|---|---|---|---|
| A | Layer(4) as is | 0.40 | 25 | 0.82 | 0.32 | 0.48 | Comparison |
| B[c] | C-3 | 0.51 | " | 1.75 | 0.30 | 0.74 | Invention |
| C[c] | C-4 | 0.42 | " | 1.82 | 0.31 | 0.69 | " |
| D[c] | C-8 | 0.44 | " | 1.88 | 0.31 | 0.66 | " |
| E[c] | C-11 | 0.51 | " | 2.01 | 0.32 | 0.60 | " |

*[1], *[2]Same as in Table 1.

EXAMPLE 3

On a transparent polyester support the following layers were successively coated to produce a light-sensitive sheet.
(1) A layer containing 0.40 g/m² of the same DRR compound as in Layer (4) in Example 1, 0.16 g/m² of tricyclohexyl phosphate, 0.05 g/m² of a formalin condensate of p-nonylphenol and sodium p-nonylphenoxybutyl sulfonate (55.45) (average degree of condensation: 3.4) and 2.0 g/m² of gelatin.
(2) A layer containing 0.40 g/m² (as silver) of a red-sensitive silver iodobromide emulsion and 0.80 g/m² of gelatin.
(3) A layer containing 1.0 g/m² of gelatin.

The above light-sensitive sheet was designated Sample F[c]. Additionally, Samples G[c], H[c], I[c] and J[c] were produced in the same manner as above except that only the cyan DRR compound of Layer (1) was replaced by the compounds as illustrated in Table 3.

The same mordanting layer as in the light-sensitive sheet of Example 1 was coated on a transparent polyester support to produce a mordanting sheet.

Each of these samples was exposed to light and then combined together at 25° C. with the same processing solution as in Example 2 and the above-prepared mordanting layer. The processing solution was developed in a thickness of 80 μm by use of a pressing member. After 5 minutes, the mordanting layer was stripped off, washed with water and, thereafter, soaked in a buffer solution with a pH of 5 and dried to obtain a transferred negative color image.

On the other hand, the light-sensitive sheet was processed with the following bleach-fixing solution and, thereafter, washed with water, soaked in a 0.2% aqueous solution of tetramethylammonium bromide and dried to obtain a reversal positive color image.

| Bleach-Fixer | |
|---|---|
| Ammonium Thiosulfate (70%) | 150 cc |
| EDTA-Fe | 36.6 g |
| EDTA-2Na | 3.4 g |
| Sodium Sulfite (anhydrous) | 12.0 g |
| Sodium Carbonate (1 H₂O salt) | 2.0 g |
| Water to make | 1 l |

The results are illustrated in Table 3. As can be seen from Table 3, in comparison with Sample F[c], Samples G[c], H[c], I[c] and J[c] were high in the maximum transmission density and low in the minimum transmission density in both the reversal positive color image and the transferred negative color image. This indicates that at the areas where the development occurs in Samples G[c], H[c], I[c] and J[c], the amount of the coated dye material converted in the transferred dye is great, that is, the amount of the coated dye material remaining in the light-sensitive sheet is very small.

TABLE 3

| Sample | DRR Compound | Amount*[1] (g/m²) | Processing Temp. (°C.) | Reversal Positive Color Image | | Transferred Negative Color Image | | Remarks |
| | | | | Cyan Maximum Transmission Density | Cyan Minimum Transmission Density | Cyan Maximum Transmission Density | Cyan Minimum Transmission Density | |
|---|---|---|---|---|---|---|---|---|
| F[c] | Layer(1) as is | 0.40 | 25 | 2.32 | 0.56 | 1.85 | 0.10 | Comparison |

TABLE 3-continued

| Sample | DRR Compound | Amount*1 (g/m²) | Processing Temp. (°C.) | Reversal Positive Color Image | | Transferred Negative Color Image | | Remarks |
| --- | --- | --- | --- | --- | --- | --- | --- | --- |
| | | | | Cyan Maximum Transmission Density | Cyan Minimum Transmission Density | Cyan Maximum Transmission Density | Cyan Minimum Transmission Density | |
| $G^c$ | C-3 | 0.51 | " | 2.31 | 0.24 | 2.15 | 0.09 | Invention |
| $H^c$ | C-4 | 0.42 | " | 2.33 | 0.22 | 2.18 | 0.08 | " |
| $I^c$ | C-8 | 0.44 | " | 2.33 | 0.19 | 2.23 | 0.09 | " |
| $J^c$ | C-11 | 0.51 | " | 2.32 | 0.17 | 2.28 | 0.10 | " |

*1 Same as in Table 1.

EXAMPLE 4

Samples $B^{m1}$, $C^{m1}$, $D^{m1}$ and $E^{m1}$ were produced in the same manner as in Sample A of Example 1, except that the magenta DRR compound of Layer (8) was replaced by the compounds as illustrated in Table 4.

Each sample was exposed to light and then combined together with the same processing solution and cover sheet as used above. The processing solution was developed at 25° C. in a thickness of 80 μm by use of a pressing member to obtain a transferred color image. The results are shown in Table 4.

TABLE 4

| Sample | DRR Compound | Amount*1 (g/m²) | Processing Temp. (°C.) | Magenta Maximum Reflective Density | Magenta Minimum Reflective Density | Gradation at*2 Foot Area (0.5/Δ log E) | Remarks |
| --- | --- | --- | --- | --- | --- | --- | --- |
| A | Layer(8) as is | 0.32 | 25 | 1.23 | 0.23 | 0.69 | Comparison |
| $B^{m1}$ | $M_1$-1 | 0.36 | " | 1.90 | 0.19 | 0.94 | Invention |
| $C^{m1}$ | $M_1$-13 | 0.36 | " | 2.05 | 0.19 | 1.14 | " |
| $D^{m1}$ | $M_1$-19 | 0.39 | " | 1.92 | 0.19 | 1.03 | " |
| $E^{m1}$ | $M_1$-22 | 0.38 | " | 1.83 | 0.20 | 0.94 | " |

*1, *2 Same as in Table 1.

EXAMPLE 5

Samples A, $B^{m1}$, $C^{m1}$, $D^{m1}$ and $E^{m1}$ were processed in the same manner as in Example 4 except that the developing agent of the processing composition was changed to 1-phenyl-4-hydroxymethyl-4-methyl-3-pyrazolidinone (13.0 g). The results obtained at 25° C. are shown in Table 5.

TABLE 5

| Sample | DRR Compound | Amount*1 (g/m²) | Processing Temp. (°C.) | Magenta Maximum Reflective Density | Magenta Minimum Reflective Density | Gradation in*2 Foot Area (0.5/Δ log E) | Remarks |
| --- | --- | --- | --- | --- | --- | --- | --- |
| A | Layer(8) as is | 0.32 | 25 | 1.48 | 0.24 | 0.74 | Comparison |
| $B^{m1}$ | $M_1$-1 | 0.36 | " | 1.94 | 0.20 | 1.02 | Invention |
| $C^{m1}$ | $M_1$-13 | 0.36 | " | 2.10 | 0.19 | 1.20 | " |
| $D^{m1}$ | $M_1$-19 | 0.39 | " | 2.00 | 0.20 | 1.11 | " |
| $E^{m1}$ | $M_1$-22 | 0.38 | " | 1.92 | 0.20 | 1.04 | " |

*1, *2 Same as in Table 1.

EXAMPLE 6

A light-sensitive sheet was produced according to Example 3 except that the cyan DRR compound in Layer (1) was replaced by 0.32 g/m² of the same magenta DRR compound as in Layer (8) of Example 1.

This light-sensitive sheet was designated Sample $F^{m1}$. Additionally, Samples $G^{m1}$, $H^{m1}$, $I^{m1}$ and $J^{m1}$ were produced in the same manner as above except that the magenta DRR compound in Layer (1) was replaced by the compounds as illustrated in Table 6.

Samples $F^{m1}$, $G^{m1}$, $H^{m1}$ and $J^{m1}$ were exposed to light and then combined together at 25° C. with the same processing solution as in Example 5 and the same mordanting sheet as in Example 3. After that, a reversal positive color image was obtained according to the same processings as in Example 3.

The results are shown in Table 6.

TABLE 6

| Sample | DDR Compound | Amount[1] (g/m²) | Processing Temp. (°C.) | Reversal Positive Color Image | | Transferred Negative Color Image | | Remarks |
|---|---|---|---|---|---|---|---|---|
| | | | | Magenta Maximum Transmission Density | Magenta Minimum Transmission Density | Magenta Maximum Transmission Density | Magenta Minimum Transmission Density | |
| $F^{m1}$ | Layer(1) as is | 0.32 | 25 | 1.17 | 0.24 | 1.08 | 0.06 | Comparison |
| $G^{m1}$ | $M_1$-1 | 0.36 | " | 1.19 | 0.05 | 1.22 | 0.03 | Invention |
| $H^{m1}$ | $M_1$-13 | 0.36 | " | 1.21 | 0.03 | 1.23 | 0.03 | " |
| $I^{m1}$ | $M_1$-19 | 0.39 | " | 1.19 | 0.05 | 1.21 | 0.03 | " |
| $J^{m1}$ | $M_1$-22 | 0.38 | " | 1.20 | 0.06 | 1.20 | 0.03 | " |

[1]Same as in Table 1.

EXAMPLE 7

Samples $B^{m2}$, $C^{m2}$, $D^{m2}$ and $E^{m2}$ were produced in the same manner as in Sample A of Example 1 except that the magenta DRR compound in Layer (8) was replaced by the compounds as illustrated in Table 7.

Each sample was exposed to light and combined together with the same processing solution and cover sheet as used in Example 1. The processing solution was developed at 25° C. in a thickness of 80 μm by use of a pressing member.

The results are shown in Table 7.

TABLE 7

| Sample | DRR Compound | Amount[1] (g/m²) | Processing Temp. (°C.) | Magenta Maximum Reflective Density | Magenta Minimum Reflective Density | Gradation at[2] Foot Area (0.5/Δ log E) | Remarks |
|---|---|---|---|---|---|---|---|
| A | Layer(8) as is | 0.32 | 25 | 1.23 | 0.23 | 0.69 | Comparison |
| $B^{m2}$ | $M_2$-1 | 0.33 | " | 1.61 | 0.19 | 1.10 | Invention |
| $C^{m2}$ | $M_2$-16 | 0.34 | " | 1.55 | 0.19 | 1.04 | " |
| $D^{m2}$ | $M_2$-33 | 0.32 | " | 1.73 | 0.20 | 1.04 | " |
| $E^{m2}$ | $M_2$-51 | 0.33 | " | 1.70 | 0.20 | 1.12 | " |

[1], [2]Same as in Table 1.

EXAMPLE 8

Sample A, $B^{m2}$, $C^{m2}$, $D^{m2}$ and $E^{m2}$ were processed in the same manner as in Example 7 except that the developing agent of the processing solution was changed to 1-phenyl-4-hydroxymethyl-4-methyl-3-pyrazolidinone (13.0 g). The results obtained at 25° C. are shown in Table 8.

TABLE 8

| Sample | DRR Compound | Amount[1] (g/m²) | Processing Temp. (°C.) | Magenta Maximum Reflective Density | Magenta Minimum Reflective Density | Gradation at[2] Foot Area (0.5/Δ log E) | Remarks |
|---|---|---|---|---|---|---|---|
| A | Layer(8) as is | 0.32 | 25 | 1.48 | 0.24 | 0.74 | Comparison |
| $B^{m2}$ | $M_2$-1 | 0.33 | " | 2.08 | 0.20 | 1.16 | Invention |
| $C^{m2}$ | $M_2$-16 | 0.34 | " | 1.90 | 0.20 | 1.08 | " |
| $D^{m2}$ | $M_2$-33 | 0.32 | " | 2.14 | 0.21 | 1.10 | " |
| $E^{m2}$ | $M_2$-51 | 0.33 | " | 2.10 | 0.21 | 1.14 | " |

[1], [2]Same as in Table 1.

EXAMPLE 9

Samples $G^{m2}$, $H^{m2}$, $I^{m2}$ and $J^{m2}$ were produced in the same manner as $F^{m1}$ except that the magenta DRR compound of Layer (1) was replaced by the compounds as illustrated in Table 9.

Each sample was exposed to light and combined together at 25° C. with the same processing solution as used in Example 8 and the same mordanting sheet as in Example 3. After that, a reversal positive color image was obtained according to the same processings as in Example 3.

The results are shown in Table 9.

TABLE 9

| Sample | DRR Compound | Amount[1] (g/m²) | Processing Temp. (°C.) | Reversal Positive Color Image | | Transferred Negative Color Image | | Remarks |
|---|---|---|---|---|---|---|---|---|
| | | | | Magenta Maximum Transmission Density | Magenta Minimum Transmission Density | Magenta Maximum Transmission Density | Magenta Minimum Transmission Density | |
| $F^{m1}$ | Layer(1) as is | 0.32 | 25 | 1.17 | 0.24 | 1.08 | 0.06 | Comparison |
| $G^{m2}$ | $M_2$1 | 0.33 | " | 1.24 | 0.06 | 1.22 | 0.03 | Invention |

TABLE 9-continued

| Sample | DRR Compound | Amount*[1] (g/m$^2$) | Processing Temp. (°C.) | Reversal Positive Color Image | | Transferred Negative Color Image | | Remarks |
|---|---|---|---|---|---|---|---|---|
| | | | | Magenta Maximum Transmission Density | Magenta Minimum Transmission Density | Magenta Maximum Transmission Density | Magenta Minimum Transmission Density | |
| H$^{m2}$ | M$_2$-16 | 0.34 | " | 1.24 | 0.06 | 1.21 | 0.03 | " |
| I$^{m2}$ | M$_2$-33 | 0.32 | " | 1.25 | 0.05 | 1.23 | 0.04 | " |
| J$^{m2}$ | M$_2$-51 | 0.33 | " | 1.26 | 0.05 | 1.23 | 0.04 | " |

*[1] Same as in Table 1.

EXAMPLE 10

Dye Compound A$^{m2}$ released from Compound M$_2$-1 was dissolved in N,N-dimethylformamide (DMF) to give a $10^{-3}$ M DMF solution of Dye Compound A$^{m2}$. This solution in the amount of 0.25 ml was diluted with 11.5 ml of DMF, and a mixture of 1.25 ml of a $10^{-1}$ M DMF solution of butyl acrylate and 12.5 ml of a buffer solution (Britton-Robinson buffer solution) with a pH of 5.05 was added thereto.

The resulting solution was allowed to stand at room temperature (25°–29° C.) and the decrease in absorbance at the visible absorption maximum wavelength was measured. The remaining ratio of Dye Compound A$^{m2}$ was calculated from the values obtained by the above measurement. Assuming that the decrease in the remaining ratio is substantially of the first order, the first order reaction rate constant k was obtained.

In the same manner as above, ks for Dye Compounds B$^{m2}$, C$^{m2}$ and D$^{m2}$ released from Compound M$_2$-55, M$_2$-56 and M$_2$-57 were obtained.

For comparison, for E$^{m2}$ containing no electron donative group in the azo component and F$^{m2}$ containing a mon-substituted electron donative group in the azo component, the k value was obtained.

The results are shown in Table 10.

TABLE 10
Reaction of Released Dye Compound and Butyl Acrylate

[Chemical structure: naphthalene with OH, CH$_3$SO$_2$NH, SO$_2$NH-C(CH$_3$)$_2$-CH$_3$, N=N-phenyl with R$^{12}$, R$^{13}$, R$^{14}$]

| Compound | R$^{12}$ | R$^{13}$ | R$^{14}$ | k (day$^{-1}$) |
|---|---|---|---|---|
| A$^{m2}$ | —CH$_3$ | —SO$_2$NH$_2$ | —CH$_3$ | 0.025 |
| B$^{m2}$ | —CH$_3$ | —CH$_3$ | —SO$_2$NH$_2$ | 0.033 |
| C$^{m2}$ | —OCH$_3$ | —SO$_2$NH$_2$ | —OCH$_3$ | 0.032 |
| D$^{m2}$ | —OCH$_3$ | —OCH$_3$ | —SO$_2$NH$_2$ | 0.012 |
| *E$^{m2}$ | —H | —SO$_2$NH$_2$ | —H | 0.098 |
| *F$^{m2}$ | —H | —SO$_2$NH$_2$ | —CH$_3$ | 0.099 |

*Comparative compounds.

From Table 10, it can be seen that Compounds A$^{m2}$ to D$^{m2}$ are excellent in fastness as compared with Comparative Compounds E$^{m2}$ to F$^{m2}$ and that the presence at the same time of two electron donor groups in the azo component is of great importance.

These test results are in good agreement with the practical fastness of the transferrred image.

EXAMPLE 11

Samples b$^y$, C$^y$ and E$^y$ were produced in the same manner as in Sample A of Example 1 except that the yellow DRR compound of Layer (12) was replaced by the compounds as illustrated in Table 11. Samples A, B$^y$, C$^y$, D$^y$ and E$^y$ were exposed to light, and combined with the same processing solutions and cover sheets as described above. The processing solution was developed at 25° C. in a thickness of 80 μm by use of a pressing member to obtain a transferred color image. The results are shown in Table 11.

TABLE 11

| Sample | DRR Compound | Amount*[1] (g/m$^2$) | Processing Temp. (°C.) | Yellow Maximum Reflective Density | Yellow Minimum Reflective Density | Gradation at*[2] Foot Area (0.5/Δ log E) | Remarks |
|---|---|---|---|---|---|---|---|
| A | Layer(12) as is | 0.53 | 25 | 1.08 | 0.20 | 0.51 | Comparison |
| B$^y$ | Y-1 | 0.74 | " | 1.43 | 0.18 | 0.69 | Invention |
| C$^y$ | Y-4 | 0.68 | " | 1.49 | 0.18 | 0.77 | " |
| D$^y$ | Y-14 | 0.66 | " | 1.52 | 0.18 | 0.72 | " |
| E$^y$ | Y-15 | 0.71 | " | 1.45 | 0.18 | 0.75 | " |

*[1], *[2] Same as in Table 1.

EXAMPLE 12

Samples A, B$^y$, C$^y$, D$^y$ and E$^y$ of Example 11 were processed in the same manner as in Example 11 except that the developing agent of the processing composition was changed to 1-phenyl-4-hydroxymethyl-4-methyl-3-pyrazolidinone (13.0 g). The results obtained at 25° C. are shown in Table 12.

TABLE 12

| Sample | DRR Compound | Amount*1 (g/m²) | Processing Temp. (°C.) | Yellow Maximum Reflective Density | Yellow Minimum Reflective Density | Gradation at*2 Foot Area (0.5/Δ log E) | Remarks |
|---|---|---|---|---|---|---|---|
| A | Layer(12) as is | 0.53 | 25 | 1.34 | 0.20 | 0.60 | Comparison |
| $B^y$ | Y-1 | 0.74 | " | 1.58 | 0.18 | 0.80 | Invention |
| $C^y$ | Y-4 | 0.68 | " | 1.53 | 0.18 | 0.86 | " |
| $D^y$ | Y-14 | 0.66 | " | 1.62 | 0.18 | 0.80 | " |
| $E^y$ | Y-15 | 0.71 | " | 1.52 | 0.18 | 0.84 | " |

*1, *2 Same as in Table 1.

EXAMPLE 13

A light-sensitive sheet was produced according to Example 3 except that the cyan DRR compound in Layer (1) was replaced by 0.53 g/m² of the same yellow DRR compound as in Layer (12) of Example 1.

The above light-sensitive sheet was designated Sample $F^y$. Additionally, Samples $G^y$, $H^y$, $I^y$ and $J^y$ were produced in the same manner as above except that only the yellow DRR compound of Layer (1) was replaced by the compounds as illustrated in Table 13.

Each sample was exposed to light and combined together at 25° C. with the same processing solution as in Example 12 and the above-prepared mordanting sheet as in Example 3. After that, a reversal positive color image was obtained according to the same processings as in Example 3. The results are shown in Table 13.

| Processing Solution | |
|---|---|
| 1-Phenyl-4-hydroxymethyl-4-methyl-3-pyrazolidinone | 13 g |
| Methylhydroquinone | 0.3 g |
| 5-Methylbenzotriazole | 3.5 g |
| Sodium Sulfite (anhydrous) | 0.2 g |
| Carboxymethyl Cellulose Na Salt | 58 g |
| Potassium Hydroxide (28% aq. soln.) | 200 cc |
| Benzyl Alcohol | 1.5 cc |
| $H_2O$ | 685 cc |

On a transparent polyester support was coated a mordanting layer containing 3.0 g/m² of the same mordant as in Sample A and 3.0 g/m² of gelatin to produce an image-receiving sheet.

The sample containing the magenta DRR compound in Layer (1) of the above light-sensitive sheet was designated ($A^m$). Sample ($B^m$) was produced in the same manner as in Sample ($A^m$) except that the magenta DRR compound was replaced by the following com-

TABLE 13

| | | | | Reversal Positive Color Image | | Transferred Negative Color Image | | |
|---|---|---|---|---|---|---|---|---|
| Sample | DRR Compound | Amount*1 (g/m²) | Processing Temp. (°C.) | Yellow Maximum Transmission Density | Yellow Minimum Transmission Density | Yellow Maximum Transmission Density | Yellow Minimum Transmission Density | Remarks |
| $F^y$ | Layer(1) as is | 0.53 | 25 | 1.10 | 0.26 | 0.90 | 0.06 | Comparison |
| $G^y$ | Y-1 | 0.74 | " | 1.12 | 0.13 | 1.03 | 0.05 | Invention |
| $H^y$ | Y-4 | 0.68 | " | 1.12 | 0.10 | 1.06 | 0.05 | " |
| $I^y$ | Y-14 | 0.66 | " | 1.11 | 0.09 | 1.08 | 0.05 | " |
| $J^y$ | Y-15 | 0.71 | " | 1.13 | 0.14 | 1.02 | 0.05 | " |

*1 Same as in Table 1.

EXAMPLE 14

On a transparent polyester support were successively coated the following layers to produce a light-sensitive sheet.

(1) A layer containing 0.43 g/m² of the magenta DRR compound of Sample A, 0.16 g/m² of tricyclohexyl phosphate and 2.0 g/m² of gelatin.

(2) A layer containing 0.80 g/m² (as silver) of a green-sensitive internal latent image type direct reversal silver bromide emulsion, 0.8 g/m² of gelatin, 0.04 mg/m² of the same nucleating agent as used in Sample A and 0.05 g/m² of sodium pentadecylhydroquinone sulfonate.

(3) A layer containing 1.1 g/m² of gelatin.

To a rupturable container was charged 0.8 g of a processing solution having the following composition.

pound. ($B^m$): A sample containing 0.47 g/m² of Compound $M_1$-14.

Each sample was exposed to light and combined together with the above processing solution-containing rupturable container and the above-prepared image-receiving sheet. The processing solution was developed at 15° C. or 25° C. in a thickness of 80 μm by use of a pressing member. After 5 minutes, the image-receiving sheet was stripped off and dipped in a 2% solution of acetic acid, and therefter it was washed with water and dried to obtain a transferred color image. The results are shown in Table 14.

TABLE 14

| Sample | Processing Temp. (°C.) | Magenta Maximum Transmission Density (Dmax) | Magenta Minimum Transmission Density (Dmin) | Gradation at* Foot Area (0.5/Δ log E) | Remarks |
|---|---|---|---|---|---|
| $(A^m)$ | 15 | 0.91 | 0.04 | 0.40 | Comparison |
| $(B^m)$ | " | 1.17 | 0.02 | 0.67 | Invention |
| $(A^m)$ | 25 | 0.95 | 0.05 | 0.45 | Comparison |
| $(B^m)$ | " | 1.23 | 0.02 | 0.67 | Invention |

*Same as in Table 1.

EXAMPLE 15

Samples $(A^m)$ and $(B^m)$ in Example 14 were processed in the same manner as in Example 14 except that the developing agent of the processing solution 1-p-tolyl-4-hydroxymethyl-4-methyl-3-pyrazolidinone (6.9 g) was changed. The results obtained at 25° C. are shown in Table 15.

TABLE 15

| Sample | Processing Temp. (°C.) | Magenta Maximum Transmission Density | Magenta Minimum Transmission Density | Gradation at* Foot Area (0.5/Δ log E) | Remarks |
|---|---|---|---|---|---|
| $(A^m)$ | 25 | 0.92 | 0.11 | 0.33 | Comparison |
| $(B^m)$ | " | 1.17 | 0.09 | 0.39 | Invention |

*Same as in Table 1.

EXAMPLE 16

On a transparent polyester support were successively coated the following layers to produce a light-sensitive sheet.

(1) A mordanting layer containing 3.0 g/m² of the same mordant as in Example 14 and 3.0 g/m² of gelatin.

(2) A white reflective layer containing 20 g/m² of titanium dioxide and 2.0 g/m² of gelatin.

(3) A light-shielding layer containing 2.70 g/m² of carbon black and 2.70 g/m² of gelatin.

(4) The same layer as Layer (1) in Sample $(A^m)$ of Example 14.

(5) The same layer as Layer (2) in Example 14.

(6) The same layer as Layer (3) in Example 14.

Into a rupturable container was charged 0.8 g of the same processing solution as used in Example 14, except that it contained 150 g of carbon black.

The sample containing the magenta DRR compound in Layer (4) of the above light-sensitive sheet was designated $(C^m)$. Additionally, $(D^m)$ was produced, in which the compound of Sample $(B^m)$ in Example 14 was used in place of compound of Sample $(A^m)$.

Samples $(C^m)$ and $(D^m)$ were exposed to light and were each combined with a processing solution-containing container as above and cover sheet as in Example 1. The processing solution was developed at 25° C. in a thickness of 80 μm by use of a pressing member to obtain a transferred color image.

TABLE 16

| Sample | Processing Temp. (°C.) | Magenta Maximum Reflective Density | Magenta Minimum Reflective Density | Gradation at Foot Area (0.5/Δ log E) |
|---|---|---|---|---|
| $(C^m)$ | 25 | 1.50 | 0.29 | 0.43 |

TABLE 16-continued

| Sample | Processing Temp. (°C.) | Magenta Maximum Reflective Density | Magenta Minimum Reflective Density | Gradation at Foot Area (0.5/Δ log E) |
|---|---|---|---|---|
| $(D^m)$ | " | 2.05 | 0.23 | 0.60 |

EXAMPLE 17

On a transparent polyester film were successively coated the following layers to produce a light-sensitive sheet.

(1), (2), (3) The same layers as in Example 16, respectively.

(4) A layer containing 0.44 g/m² of Compound C-11 (cyan DRR compound), 0.09 g/m² of tricyclohexyl phosphate, 0.008 g/m² of 2,5-di-tert-pentadecylhydroquinone and 0.8 g/m² of gelatin.

(5), (6), (7) The same layers as in Example 1, respectively.

(8) A layer containing 0.29 g/m² of Compound $M_1$-1 (magenta DRR compound), 0.15 g/m² of Compound $M_2$-1 (magenta DRR compound), 0.08 g/m² of tricyclohexyl phosphate, 0.009 g/m² of 2,5-di-tert-pentadecylhydroquinone and 0.9 g/m² of gelatin.

(9), (10), (11), (13), (14) The same layers as in Example 1, respctively.

(12) The same layer as in Example 1, except that only the piror yellow DRR compound is replaced by Compound Y-1.

The above light-sensitive sheet was exposed to light and combined together with the same processing solution-containing container as used in Example 15 and the same cover sheet as used in Example 1. The processing solution was developed at 25° C. in a thickness of 80 μm by use of a pressing member to obtain a transferred color image. The transferred color image exhibited a satisfactory maximum reflective density, a satisfactory minimum reflective density and a good gradation.

EXAMPLE 18

On a transparent polyester support were successively coated the following layers to produce a light-sensitive sheet.

(1) A layer containing 0.52 g/m² of a cyan DRR compound as illustrated below, 0.16 g/m² of tricyclohexyl phosphate, 0.05 g/m² of a formalin condensate of p-nonyphenol and sodium p-nonylphenoxybutyl sulfonate (55:45) (average degree of condensation: 3.4) and 2.0 g/m² of gelatin.

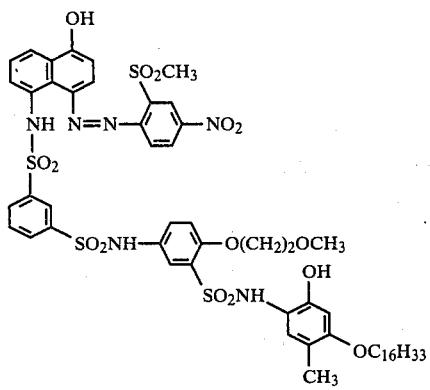

(2) A layer containing 0.40 g/m² (as silver) of a blue-sensitive silver iodobromide emulsion and 0.80 g/m² of gelatin.

(3) A layer containing 1.0 g/m² of gelatin.

The thus-obtained light-sensitive sheet was designated Sample (E). In the same manner as above except that the cyan DRR compound in Layer (1) was changed as indicated below, Samples (F), (G), (H) and (I) were produced.

Sample (F): 0.54 g/m² of Compound C-11 was contained.

Sample (G): 0.43 g/m² of the same compound as used in Sample ($A^m$) in Example 14 was contained.

Sample (H): 0.45 g/m² of Compound $M_1$-1 was contained.

Samples (E), (F), (G), (H) and (I) were processed according to Example 3 to obtain a reversal dye image (i.e., positive dye image).

The results are shown in Table 17. As can be seen from Table 17, in comparison with Comparitive Samples (E) and (G), Samples (F), (H) and (I) of this invention were very small in the minimum transmission density.

This means that the amount of the DRR compound remaining at the exposed areas (non-image areas) of Samples (F), (H) and (I) were very small. Or, in other words, this means that the DRR compound of this invention is markedly high in the dye-releasing efficiency.

TABLE 17

| Sample | Minimum Transmission Density | Remarks |
|---|---|---|
| (E) | 0.56 | Cyan color image (comparative) |
| (F) | 0.17 | Cyan color image (this invention) |
| (G) | 0.27 | Magenta color image (comparative) |
| (H) | 0.12 | Magenta color image (this invention) |
| (I) | 0.10 | Magenta color image (this invention) |

EXAMPLE 19

According to Examples 14 to 17, the employment of Compounds $M_1$-26 and C-20 also each provided good results such as high maximum reflective or transmission density, low minimum transmission or reflective density, good gradation in the foot area, great conversion ratio and great utilization ratio.

While the invention has been described in detail and with reference to specific embodiments thereof, it will be apparent to one skilled in the art that various changes and modifications can be made therein without departing from the spirit and scope thereof.

What is claimed is:

1. A color photographic light-sensitive material containing at least one light-sensitive silver halide emulsion layer combined with a dye-releasing redox compound represented by formula (I):

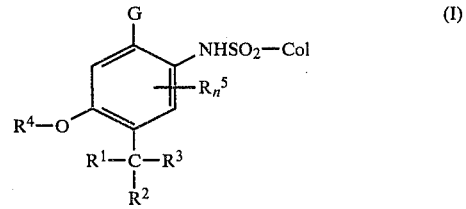

wherein G represents a hydroxy group or a group providing a hydroxy group by hydrolysis;

Col represents a dye or dye precursor;

$R^1$ and $R^2$, which may be the same or different, each represents an alkyl group or an aromatic group, and $R^1$ and $R^2$ together can form a ring;

$R^3$ represents hydrogen, an alkyl group or an aromatic group;

$R^4$ can represent an alkyl group or an aromatic group;

$R^5$ can represent an alkyl group, an alkoxy group, an alkylthio group, an arylthio group, a halogen atom or an acylamino group;

n is 0, 1 or 2, and when n is 2, the two $R^5$s can be different from each other; and $R^4$ and an $R^5$ together can form a heterocyclic ring, $R^1$ and $R^4$ together can form a heterocyclic ring, $R^1$ and $R^5$ together can form a ring, $R^1$, $R^2$ and $R^3$ together can form an adamantyl ring, and the total number of carbon atoms of $R^1$, $R^2$, $R^3$, $R^4$ and $R^5_n$ is more than 7.

2. A color photographic light-sensitive material as in claim 1 containing a dye-releasing redox compound represented by formula (I) wherein G represents a hydroxy group and n is 1.

3. A color photographic light-sensitive material as in claim 1 or 2 wherein the alkyls group represented by $R^1$, $R^2$, $R^3$, and $R^4$ contain from 1 to 40 carbon atoms.

4. A color photographic light-sensitive material as in claim 3, wherein the alkyls group represented by $R^1$, $R^2$, $R^3$, and $R^4$ contain from 1 to 24 carbon atoms.

5. A color photographic light-sensitive material as in claim 1 or 2 wherein the aromatic groups represented by $R^1$, $R^2$, $R^3$, and $R^4$ are selected from the group consisting of a phenyl group, a substituted phenyl group, a naphthyl group and a substituted naphthyl group.

6. A color photographic light-sensitive material as in claim 1 or 2 wherein the alkyl group, the alkoxy group, or the alkylthio group represented by $R^5$ contains from 1 to 40 carbon atoms.

7. A color photographic light-sensitive material as in claim 6 wherein the alkyl group, the alkoxy group, or the alkylthio group represented by $R^5$ contains from 1 to 24 carbon atoms.

8. A color photographic material as in claim 1 wherein the dye-releasing redox compound is a compound represented by the formula (II):

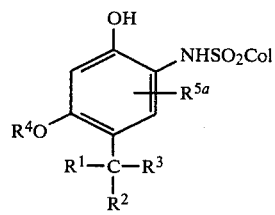 (II)

wherein Col represents a dye or a dye precursor; $R^1$ and $R^2$, which may be the same or different, each represents an alkyl group or an aromatic group, or $R^1$ and $R^2$ together can form a saturated hydrocarbon ring; $R^3$ represents a hydrogen atom, an alkyl group or an aromatic group or $R^1$, $R^2$ and $R^3$ together can form an adamantyl group; $R^4$ represents an aryloxyalkyl group or an unsubstituted alkyl group; and $R^{5a}$ represents a hydrogen atom, an alkyl group, or an alkoxy group.

9. A color photographic material as in claim 8, wherein $R^1$ and $R^2$, which may be the same or different, each represents an alkyl group or an aromatic group; and $R^3$ represents an alkyl group or an aryl group.

10. A color photographic material as in claim 8 wherein the

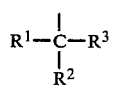

group is a t-butyl group, a cyclohexyl group, an adamantyl group, an t-amyl group, an 1-ethyl-1-methylpentyl group, a t-hexyl group, an t-octyl group or a

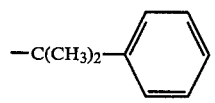

group.

11. A color photographic material as in claim 1, wherein Col is represented by the formula C-(I), $M_1$-(I), $M_2$-(I), Y-(I) or Y-(II).

12. A color photographic material as in claim 11, wherein Col is represented by the formula C-(II), $M_1$-(II), $M_1$-(III), Y-(III) or Y-(IV).

13. A color photographic material as in claim 11 containing a combination of (a) the dye-releasing redox compound represented by the formula (I) and having a group represented by the formula $M_1$-(I) as "Col" and (b) the dye-releasing redox compound represented by the formula (I) and having a group represented by the formula $M_2$-(I) as "Col".

14. A color photographic material as in claim 1 further comprising a 1-aryl-3-pyrazolidone series developing agent.

15. A color photographic material as in claim 14 wherein the developing agent is represented by the formula:

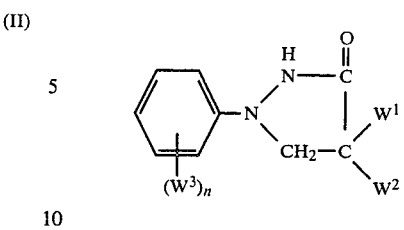

wherein $W^1$ and $W^2$, which may be the same or different, each represents hydrogen, an alkyl group or an aryl group, or $W^1$ and $W^2$ together can form a 4- to 8-membered carbon ring; $W^3$ represents hydrogen, or a substituent with which Hammett's $\sigma$ is negative; and n represents an integer of 1 to 5.

16. A color photographic material as in claim 14, wherein the developing agent has the half wave potential of polarography in the range of from about $-80$ mV to about $-200$ mV.

17. A color photographic material as in claim 16 wherein the half wave potential is in the range of from about $-100$ mV to about $-150$ mV.

18. A color photographic material as in claim 14 wherein the 1-aryl-3-pyrazolidinone series developing agent is contained in combination with a hydroquinone series compound.

19. A color photographic light-sensitive material as in claim 1 wherein the ring formed by $R^1$ and $R^2$ is a carbocyclic ring or a heterocyclic ring.

20. A color photographic light-sensitive material as in claim 1 wherein the ring formed by $R^1$ and $R^5$ is a carbocyclic ring or a heterocyclic ring.

21. A color photographic light-sensitive material as in claim 1 containing a compound selected from the group consisting of compounds of the formula:

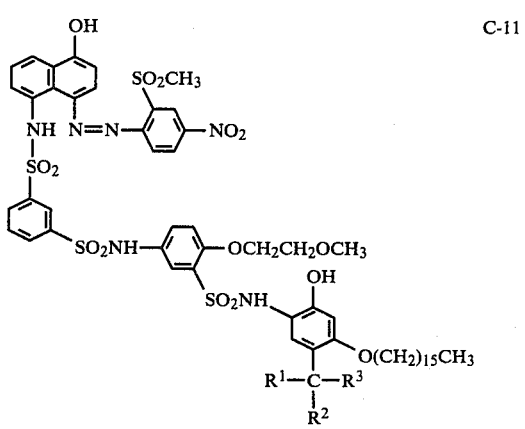

C-11 wherein $R^1 = R^2 = R^3 = CH_3$;

C-22
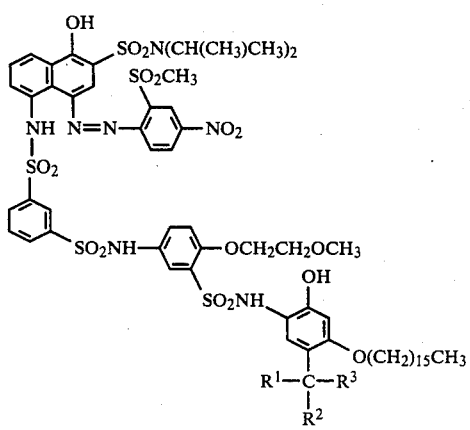
wherein $R^1 = R^2 = R^3 = CH_3$;
M₁-1
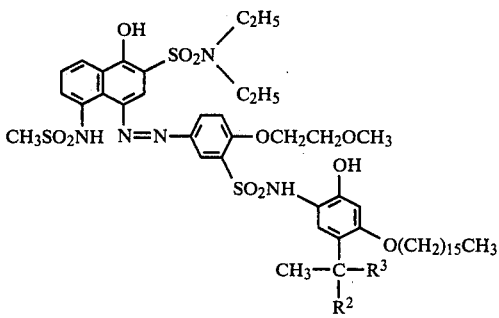
wherein $Y^3 = Y^4 = C_2H_5$;
M₁-15
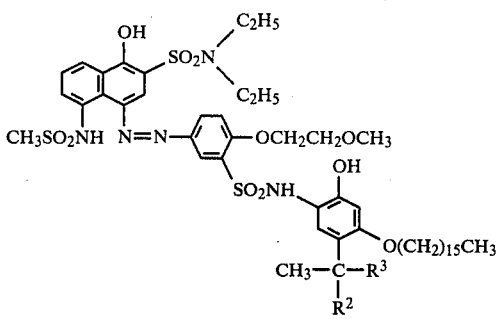
wherein $R^2 = CH_3$ and $R^3 = C_2H_5$;
M₁-16
wherein $R^2 = CH_3$ and $R^3 = CH_2-C(CH_3)_3$
M-1
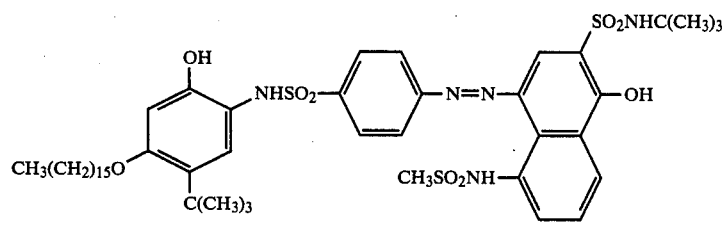
M₂-1
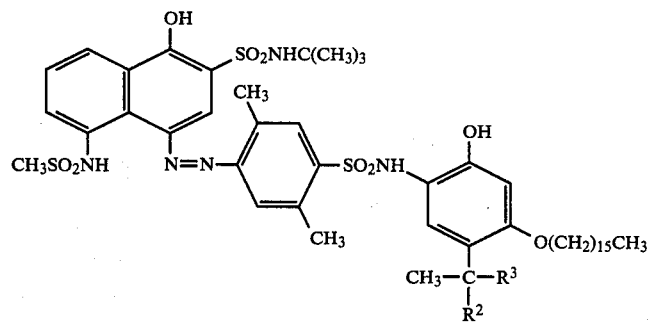
$R^2 = R^3 = CH_3$
wherein $R^2 = R^3 = CH_3$;

Y-4

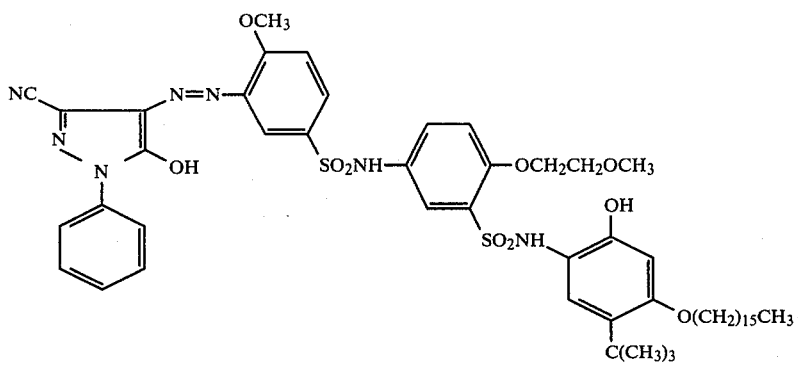

and

Y-14

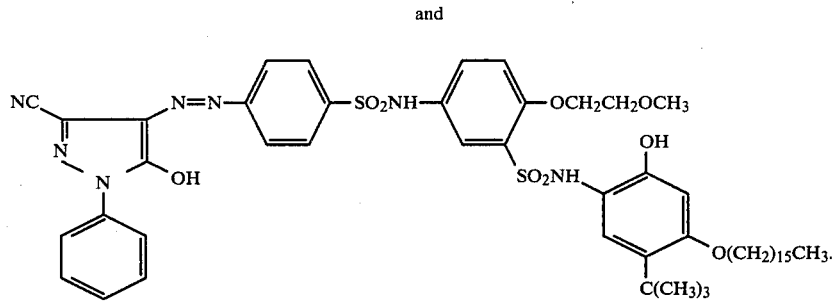

22. A method of producing a color image which comprises processing an exposed photographic light-sensitive material containing a dye-releasing redox compound in the presence of a 1-aryl-3-pyrazolidinone series developing wherein said dye-releasing redox compound has the formula

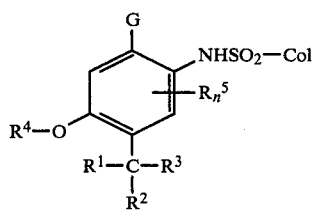

(I)

wherein G represents a hydroxy group or a group providing a hydroxy group by hydrolysis;

Col represents a dye or dye precursor;

$R^1$ and $R^2$, which may be the same or different, each represents an alkyl group or an aromatic group, and $R^1$ and $R^2$ together can form a ring;

$R^3$ represents hydrogen, an alkyl group or an aromatic group;

$R^4$ can represent an alkyl group or an aromatic group;

$R^5$ can represent an alkyl group, an alkoxy group, an alkylthio group, an arylthio group, a halogen atom or an acylamino group;

n is 0, 1 or 2, and when n is 2, the two $R^5$s can be different from each other; and $R^4$ and an $R^5$ together can form a heterocyclic ring, $R^1$ and $R^4$ together can form a heterocyclic ring, $R^1$ and $R^5$ together can form a ring, $R^1$, $R^2$ and $R^3$ together can form an adamantyl ring, and the total number of carbon atoms of $R^1$, $R^2$, $R_3$, $R^4$ and $R_n^5$ is more than 7.

23. A method of producing a color image as in claim 22 wherein the method is a color diffusion transfer process.

* * * * *